(12) United States Patent
Bradley et al.

(10) Patent No.: US 10,520,504 B2
(45) Date of Patent: Dec. 31, 2019

(54) FLUORESCENT POLYBRANCHED PROBES FOR DETECTING BACTERIA AND/OR FUNGI IN VITRO AND IN VIVO

(71) Applicant: The University Court of the University of Edinburgh, Edinburgh (GB)

(72) Inventors: Mark Bradley, Edinburgh (GB); Annamaria Helena Lilienkampf, Edinburgh (GB); Nikolaos Avlonitis, Korydallos (GR); Marc Vendrell Escobar, Edinburgh (GB); Neil Alexander McDonald, Edinburgh (GB); Christopher Haslett, Edinburgh (GB); Kanwaldeep Dhaliwal, Edinburgh (GB); Timothy Simon Walsh, North Berwick (GB)

(73) Assignee: The University Court of the University of Edinburgh (GB)

( * ) Notice: Subject to any disclaimer, the term of this patent is extended or adjusted under 35 U.S.C. 154(b) by 0 days.

(21) Appl. No.: 15/526,117

(22) PCT Filed: Nov. 13, 2015

(86) PCT No.: PCT/GB2015/053455
§ 371 (c)(1),
(2) Date: May 11, 2017

(87) PCT Pub. No.: WO2016/075484
PCT Pub. Date: May 19, 2016

(65) Prior Publication Data
US 2018/0120314 A1    May 3, 2018

(30) Foreign Application Priority Data

Nov. 13, 2014 (GB) .................................. 1420221.2

(51) Int. Cl.
| C07K 7/08 | (2006.01) |
| C12Q 1/04 | (2006.01) |
| G01N 33/569 | (2006.01) |
| A61K 49/00 | (2006.01) |
| G01N 33/58 | (2006.01) |

(52) U.S. Cl.
CPC .... *G01N 33/56911* (2013.01); *A61K 49/0021* (2013.01); *A61K 49/0054* (2013.01); *A61K 49/0056* (2013.01); *C12Q 1/04* (2013.01); *G01N 33/56961* (2013.01); *G01N 33/582* (2013.01); *C07K 7/08* (2013.01); *C12Q 2304/00* (2013.01); *G01N 2333/195* (2013.01); *G01N 2333/37* (2013.01)

(58) Field of Classification Search
CPC ........ C07K 7/08; C07K 14/435; C07K 14/47; C12Q 1/04; C12Q 1/06; C12Q 2304/00; G01N 33/52; G01N 33/582; G01N 2333/195–365; G01N 2333/37–40
See application file for complete search history.

(56) References Cited

U.S. PATENT DOCUMENTS

| 6,051,395 A | 4/2000 | Rocco | |
| 6,884,776 B1 * | 4/2005 | Nibbering | .............. C07K 14/00 514/2.3 |
| 2004/0265295 A1 * | 12/2004 | Anderson | .............. A61K 38/45 424/94.5 |
| 2005/0214221 A1 | 9/2005 | Poss | |
| 2007/0026433 A1 * | 2/2007 | Hildebrand | ...... G01N 33/56977 435/6.14 |
| 2007/0065840 A1 * | 3/2007 | Naguibneva | .......... C12N 15/111 435/6.11 |
| 2010/0233743 A1 * | 9/2010 | Uri | ..................... A61K 49/0041 435/15 |
| 2011/0171136 A1 | 7/2011 | Poss | |
| 2012/0252137 A1 | 10/2012 | Novitsky | |
| 2016/0002619 A1 * | 1/2016 | Stalnecker | ..... C12Y 305/01002 435/7.72 |

FOREIGN PATENT DOCUMENTS

| WO | 2003/014743 A2 | 2/2003 |
| WO | 2003/079015 | 9/2003 |
| WO | 2007008080 A2 | 1/2007 |
| WO | 2007008080 A3 | 1/2007 |
| WO | 2012136958 A2 | 10/2012 |
| WO | 2012136958 A3 | 10/2012 |
| WO | 2012136958 A8 | 10/2012 |

(Continued)

OTHER PUBLICATIONS

McDonald et al. Acoustic fingerprints of dye-labeled protein submicrosphere photoacoustic contrast agents. Journal of Biomedical Optics. May/Jun. 2009, vol. 14, No. 3, 034032. (Year: 2009).*
Nicolaos Avlonitis,et al; Highly specific, multi-branched fluorescent reporters reporters for analysis of human neutrophil elastase; Organic & Biomolecular Chemistry; 2013; vol. 11, No. 26; July pp. 4414-4418.
Roger D. Pechous, et al; Early Host Cell Targets of Yersinia pestis during Primary Pneumonic Plague; PLOS Pthogens—www.plospathogens.org; Oct. 2013—vol. 9; Issue 10; e1003679.

(Continued)

*Primary Examiner* — Jeffrey E. Russel
(74) *Attorney, Agent, or Firm* — Dickinson Wright PLLC

(57) ABSTRACT

A probe for detecting bacteria and/or fungi in vitro and in vivo is provided, the probe having a core and a plurality of probe elements; each probe element within the plurality of probe elements extending from the core and having a fluorophore and a binding moiety, wherein the binding moiety is a bacteria binding moiety and selectively binds to bacteria and/or to fungi and not to animal cells. Methods of use of the probe and kits comprising the probe are also provided.

15 Claims, 36 Drawing Sheets
Specification includes a Sequence Listing.

(56) References Cited

FOREIGN PATENT DOCUMENTS

| WO | 2013033436 A1 | 3/2013 |
|---|---|---|
| WO | 2014093031 A1 | 6/2014 |

OTHER PUBLICATIONS

Cuicui Liu, et al.; Noninvasive Optical Imaging of *Staphylococcus aureus* Infection in Vivo using an Antimicrobial Peptide Fragment Based Near-Infrared Fluorescent Probes; Jul. 25, 2013; Journal of Innovative Optical Health Sciences vol. 6. No. 3 (2013) 1350026 (9 pages); XP2753983A.

Ahsan R. Akram, et al.; A labelled-ubiquicidin antimicrobial peptide for immediate in situ optical detection of live bacteria in human alveolar lung tissue; Jan. 1, 2015; Chemical Science; vol. 6 pp. 6971-6979;XP055247541.

Wong P T et al., "A lipopolysaccharide binding heteromultivalent dendrimer nanoplatform for Gram negative Cell targeting"; Feb. 14, 2015; Journal of Materials Chemistry; vol. 3. No. 6 pp. 1149-1156.

Wong P T et al.; "Supporting information to a lipopolysaccharide binding heteromultivalent dendrimer naoplatform for Gram negative cell targeting"; Feb. 14, 2015; Journal of Materials Chemistry B; pp. S1-S22, XP002754621.

AR Akram et al. "T4: Optically detectable antimicrobial petitdes enable the immediate detection of bacteria and fungi in the lung" THROAX, vol. 70 No. Suppl. 3 Dec. 1, 2015, pp. A2-A3 XP008178907.

Xiao Shuzhang et al. "Multivalent Dendritic Molecules as Broad Spectrum Bacteria Agglutination Agents" Aug. 10, 2013; Theranostics; vol. 3 No. 9 pp. 658-666, XP0002754164.

International Search Report, dated Feb. 11, 2016, PCT/GB2015/053454.

Deris Zakuan et al. "Probing the Penetration of Antimicrobial Polymyxin Lipopeptides into Gram-Negative Bacteria" Apr. 2014; Bioconjugate Chemistry; vol. 25, No. 4, pp. 750-760, XP002754088.

Warsen A E et al. "Simultaneous discrimination between 15 fish pathogens by using 16S ribosomal DNA PCR and DNA microarrays" Jul. 2004; Applied and Environmental Microbiology Jul. 2004 American Society for Microbiology US; vol. 70, No. 7, pp. 4261-4221, XP002754089.

M. Ternon, J. Jose Diaz-Mochon, A. Belsom and M. Bradley, Tetrahedron, Science Direct, 2004, 60, 8721-8728, School of Chemistry, University of Southampton, Highfield, Southampton SO17 1BJ, UK.

H. J. Knölker, T. Braxmeier, G. Schlechtingen, A Novel Method for the Synthesis of Isocyanates Under Mild Conditions, Angew. Chem. Int. Ed., 1995, 34, 2497-2500, England.

E. Kaiser, R. L. Colescott, C. D. Bossinger and P. I. Cook, Color Test for Detection of Free Terminal Amino Groups in the Solid-Phase Synthesis of Peptides, Analytical Biochemistry, 1970, 34, 595-598, Armour Pharmaceutical Company, Kankakee, Illinois.

\* cited by examiner

A

FM-464     FAM-Ubi     MERGE (FAM-Ubi)

FM-464     NBD-Ubi     MERGE (NBD-Ubi)

B

FM 464     NBD-Ubi     MERGE

A

B

A

B

A

B

A

Gram-positive | Gram-negative

A

MR-AAPV-NBD-UBI    (SEQ ID NO:9)

elastase

MR-AA        PV-NBD-UBI

Bacterial labelling

Fig 16A

FM 464    NEBac    MERGE

No Elastase Inhibitor

+100µM Elastase Inhibitor

Fig 16B

SEQUENCE LISTING

<160> NUMBER OF SEQ ID NOS: 20

<210> SEQ ID NO 1
<211> LENGTH: 59
<212> TYPE: PRT
<213> ORGANISM: Homo sapiens

<400> SEQUENCE: 1

```
Lys Val His Gly Ser Leu Ala Arg Ala Gly Lys Val Arg Gly Gln Thr
1               5                   10                  15

Pro Lys Val Ala Lys Gln Glu Lys Lys Lys Lys Thr Gly Arg Ala
            20                  25                  30

Lys Arg Arg Met Gln Tyr Asn Arg Arg Phe Val Asn Val Pro Thr
        35                  40                  45

Phe Gly Lys Lys Lys Gly Pro Asn Ala Asn Ser
    50                  55

<210> SEQ ID NO 2
<211> LENGTH: 13
<212> TYPE: PRT
<213> ORGANISM: artificial
<220> FEATURE:
<223> OTHER INFORMATION: Ubiquicidin fragmant

<400> SEQUENCE: 2

Thr Gly Arg Ala Lys Arg Arg Met Gln Tyr Asn Arg Arg
1               5                   10

<210> SEQ ID NO 3
<211> LENGTH: 13
<212> TYPE: PRT
<213> ORGANISM: artificial
<220> FEATURE:
<223> OTHER INFORMATION: Ubiquicidin fragment with a methionine to
      norleucine substitution
<220> FEATURE:
<221> NAME/KEY: MISC_FEATURE
<222> LOCATION: (8)..(8)
<223> OTHER INFORMATION: X is norleucine

<400> SEQUENCE: 3

Thr Gly Arg Ala Lys Arg Arg Xaa Gln Tyr Asn Arg Arg
1               5                   10

<210> SEQ ID NO 4
<211> LENGTH: 10
<212> TYPE: PRT
<213> ORGANISM: Bacillus polymyxa
<220> FEATURE:
<221> NAME/KEY: MISC_FEATURE
<222> LOCATION: (1)..(1)
<223> OTHER INFORMATION: X is Dbu
<220> FEATURE:
<221> NAME/KEY: MISC_FEATURE
<222> LOCATION: (3)..(5)
<223> OTHER INFORMATION: X is Dbu
<220> FEATURE:
<221> NAME/KEY: MISC_FEATURE
<222> LOCATION: (6)..(6)
<223> OTHER INFORMATION: Phe undergoes post-translational isomerization
      to D-Phe
<220> FEATURE:
<221> NAME/KEY: MISC_FEATURE
<222> LOCATION: (8)..(9)
<223> OTHER INFORMATION: X is Dbu
<220> FEATURE:
<221> NAME/KEY: MISC_FEATURE
<222> LOCATION: (10)..(10)

<400> SEQUENCE: 4

Xaa Thr Xaa Xaa Xaa Phe Leu Xaa Xaa Thr
1               5                   10

<210> SEQ ID NO 5
<211> LENGTH: 10
<212> TYPE: PRT
```

```
<213> ORGANISM: Bacillus polymyxa
<220> FEATURE:
<221> NAME/KEY: MISC_FEATURE
<222> LOCATION: (1)..(1)
<223> OTHER INFORMATION: X is Dbu
<220> FEATURE:
<221> NAME/KEY: MISC_FEATURE
<222> LOCATION: (1)..(1)
<223> OTHER INFORMATION: Bound to 6-methyloctanoic acid
<220> FEATURE:
<221> NAME/KEY: MISC_FEATURE
<222> LOCATION: (3)..(5)
<223> OTHER INFORMATION: X is Dbu
<220> FEATURE:
<221> NAME/KEY: MISC_FEATURE
<222> LOCATION: (6)..(6)
<223> OTHER INFORMATION: Phe undergoes post-translational isomerization
      to D-Phe
<220> FEATURE:
<221> NAME/KEY: MISC_FEATURE
<222> LOCATION: (8)..(9)
<223> OTHER INFORMATION: X is Dbu
<220> FEATURE:
<221> NAME/KEY: MISC_FEATURE
<222> LOCATION: (10)..(10)
<223> OTHER INFORMATION: Loop formed by the binding of Thr to the 4th
      amino acid residue (Dbu)

<400> SEQUENCE: 5

Xaa Thr Xaa Xaa Xaa Phe Leu Xaa Xaa Thr
1               5                   10

<210> SEQ ID NO 6
<211> LENGTH: 10
<212> TYPE: PRT
<213> ORGANISM: bacillus polymyxa
<220> FEATURE:
<221> NAME/KEY: MISC_FEATURE
<222> LOCATION: (1)..(1)
<223> OTHER INFORMATION: X is Dbu
<220> FEATURE:
<221> NAME/KEY: MISC_FEATURE
<222> LOCATION: (1)..(1)
<223> OTHER INFORMATION: Bound to 6-methylheptanoic acid
<220> FEATURE:
<221> NAME/KEY: MISC_FEATURE
<222> LOCATION: (3)..(5)
<223> OTHER INFORMATION: X is Dbu
<220> FEATURE:
<221> NAME/KEY: MISC_FEATURE
<222> LOCATION: (6)..(6)
<223> OTHER INFORMATION: Phe undergoes post-translational isomerization
      to D-Phe
<220> FEATURE:
<221> NAME/KEY: MISC_FEATURE
<222> LOCATION: (8)..(9)
<223> OTHER INFORMATION: X is Dbu
<220> FEATURE:
<221> NAME/KEY: MISC_FEATURE
<222> LOCATION: (10)..(10)
<223> OTHER INFORMATION: Loop formed by the binding of Thr to the 4th
      amino acid residue (Dbu)

<400> SEQUENCE: 6

Xaa Thr Xaa Xaa Xaa Phe Leu Xaa Xaa Thr
1               5                   10

<210> SEQ ID NO 7
<211> LENGTH: 4
<212> TYPE: PRT
<213> ORGANISM: artificial
<220> FEATURE:
<223> OTHER INFORMATION: Mass spectrometry fragment of SEQ ID NO 3

<400> SEQUENCE: 7
```

Tyr Asn Arg Arg
1

<210> SEQ ID NO 8
<211> LENGTH: 6
<212> TYPE: PRT
<213> ORGANISM: artificial
<220> FEATURE:
<223> OTHER INFORMATION: Mass spectrometry fragment of SEQ ID NO 3,
      Ubiquicidin fragment with a  methionine to norleucine substitution
<220> FEATURE:
<221> NAME/KEY: misc_feature
<222> LOCATION: (1)..(1)
<223> OTHER INFORMATION: X is norleucine

<400> SEQUENCE: 8

Xaa Gln Tyr Asn Arg Arg
1               5

<210> SEQ ID NO 9
<211> LENGTH: 4
<212> TYPE: PRT
<213> ORGANISM: Artificial Sequence
<220> FEATURE:
<223> OTHER INFORMATION: enzyme cleavable peptide sequence

<400> SEQUENCE: 9

Ala Ala Pro Val
1

<210> SEQ ID NO 10
<211> LENGTH: 6
<212> TYPE: PRT
<213> ORGANISM: Artificial Sequence
<220> FEATURE:
<223> OTHER INFORMATION: enzyme cleavable peptide sequence
<220> FEATURE:
<221> NAME/KEY: MOD_RES
<222> LOCATION: (4)..(4)
<223> OTHER INFORMATION: Nle

<400> SEQUENCE: 10

Glu Glu Ile Xaa Arg Arg
1               5

<210> SEQ ID NO 11
<211> LENGTH: 6
<212> TYPE: PRT
<213> ORGANISM: Artificial Sequence
<220> FEATURE:
<223> OTHER INFORMATION: enzyme cleavable peptide sequence
<220> FEATURE:
<221> NAME/KEY: MISC_FEATURE
<222> LOCATION: (1)..(1)
<223> OTHER INFORMATION: X is one or more additional amino acids
<220> FEATURE:
<221> NAME/KEY: MISC_FEATURE
<222> LOCATION: (6)..(6)
<223> OTHER INFORMATION: X is one or more additional amino acids

<400> SEQUENCE: 11

Xaa Ala Ala Pro Val Xaa
1               5

<210> SEQ ID NO 12
<211> LENGTH: 5
<212> TYPE: PRT
<213> ORGANISM: Artificial Sequence
<220> FEATURE:

```
<223> OTHER INFORMATION: enzyme cleavable peptide sequence
<220> FEATURE:
<221> NAME/KEY: MISC_FEATURE
<222> LOCATION: (1)..(1)
<223> OTHER INFORMATION: x is one or more additional amino acids

<400> SEQUENCE: 12

Xaa Ala Ala Pro Val
1               5

<210> SEQ ID NO 13
<211> LENGTH: 5
<212> TYPE: PRT
<213> ORGANISM: Artificial Sequence
<220> FEATURE:
<223> OTHER INFORMATION: enzyme cleavable peptide sequence
<220> FEATURE:
<221> NAME/KEY: MISC_FEATURE
<222> LOCATION: (5)..(5)
<223> OTHER INFORMATION: x is one or more additional amino acids

<400> SEQUENCE: 13

Ala Ala Pro Val Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: enzyme cleavable peptide sequence

<400> SEQUENCE: 14

Gly Pro Lys Gly Leu Lys Gly
1               5

<210> SEQ ID NO 15
<211> LENGTH: 7
<212> TYPE: PRT
<213> ORGANISM: Artificial Sequence
<220> FEATURE:
<223> OTHER INFORMATION: enzyme cleavable peptide sequence

<400> SEQUENCE: 15

Val Ala Asp Cys Ala Asp Tyr
1               5

<210> SEQ ID NO 16
<211> LENGTH: 4
<212> TYPE: PRT
<213> ORGANISM: Artificial Sequence
<220> FEATURE:
<223> OTHER INFORMATION: enzyme cleavable peptide sequence

<400> SEQUENCE: 16

Ala Ala Pro Phe
1

<210> SEQ ID NO 17
<211> LENGTH: 6
<212> TYPE: PRT
<213> ORGANISM: Artificial Sequence
<220> FEATURE:
<223> OTHER INFORMATION: enzyme cleavable peptide sequence
<220> FEATURE:
<221> NAME/KEY: MISC_FEATURE
<222> LOCATION: (4)..(4)
<223> OTHER INFORMATION: x is 4-guanidine-L- phenylalanine
```

```
<400> SEQUENCE: 17

Phe Val Thr Xaa Ser Trp
1               5

<210> SEQ ID NO 18
<211> LENGTH: 4
<212> TYPE: PRT
<213> ORGANISM: Artificial Sequence
<220> FEATURE:
<223> OTHER INFORMATION: enzyme cleavable peptide sequence

<400> SEQUENCE: 18

Asp Glu Val Asp
1

<210> SEQ ID NO 19
<211> LENGTH: 15
<212> TYPE: PRT
<213> ORGANISM: Artificial Sequence
<220> FEATURE:
<223> OTHER INFORMATION: peptide sequence in Cyclic variant of
      NBD-UBINle
<220> FEATURE:
<221> NAME/KEY: MOD_RES
<222> LOCATION: (9)..(9)
<223> OTHER INFORMATION: Nle

<400> SEQUENCE: 19

Lys Thr Gly Arg Ala Lys Arg Arg Xaa Gln Tyr Asn Arg Arg Gly
1               5                   10                  15

<210> SEQ ID NO 20
<211> LENGTH: 5
<212> TYPE: PRT
<213> ORGANISM: Artificial Sequence
<220> FEATURE:
<223> OTHER INFORMATION: peptide in MR-AAPV-K(NBD)-PEG-OH

<400> SEQUENCE: 20

Ala Ala Pro Val Lys
1               5
```

FLUORESCENT POLYBRANCHED PROBES FOR DETECTING BACTERIA AND/OR FUNGI IN VITRO AND IN VIVO

CROSS-REFERENCE TO RELATED APPLICATIONS

The present application is a 35 U.S.C. Section 371 national stage filing of International Patent Application No. PCT/GB2015/053455, filed 13 Nov. 2015, and through which priority is claimed to United Kingdom Patent Application 1420221.2, filed 13 Nov. 2014.

SEQUENCE LISTING

This disclosure incorporates by reference in its entirety the material in the accompanying ASCII text file designated pctgb2015053455-seql, created 6 Mar. 2019 and having a file size of 7,000 bytes.

FIELD OF THE INVENTION

The invention relates to the field of molecular probes, more specifically to molecular probes for the detection of micro-organisms such as bacteria and fungi.

BACKGROUND OF THE INVENTION

There is a growing burden of bacterial infections worldwide and accurate diagnosis remains a cornerstone to providing accurate treatment.

Patients within hospitals and in healthcare generally, are at risk of bacterial infections. Hospital acquired infections (HAI) are becoming more common, and the ability to respond to such infections rapidly and accurately, is increasingly important. Where the patients have an active and healthy immune system, the dangers posed by HAI are reduced. However, the immune system of patients that are seriously ill are often at least partially compromised, making the patient especially vulnerable to HAIs.

Ventilated patients in critical care, and indeed all immunocompromised patients, are especially vulnerable to HAI, and one of the most devastating HAI remains ventilator associated pneumonia (VAP). VAP remains notoriously difficult to accurately diagnose and inappropriate treatment has been shown to be harmful to patients. Accordingly, VAP has a high mortality rate, significant morbidity and remains a burden on healthcare resources. In terms of diagnosis, the gold standard remains pulmonary biopsy, which is an invasive and rarely utilised investigation owing to the intrinsic invasive nature of the test. Other methods such as bronchoalveolar lavage remain controversial, while non-culture methods have not had any significant impact or robust validation. Clinical signs of fever, increased oxygen dependence and tachycardia remain as non-specific means of detecting inflammation or acute lung injury and therefore, alternative approaches are required that will allow the accurate and timely diagnosis of VAP, which will allow immediate healthcare decisions to be made and, with appropriate therapy, improve patient outcomes.

Currently clinicians are faced with significant uncertainty in relation to when and if to commence antibiotic treatment, the choice of agents to use, and if treatment begins, when to de-escalate therapy. These issues are barriers to effective antibiotic stewardship because of the proven association between delayed and inadequate antibiotic therapy and adverse clinical outcomes.

Molecular imaging technologies can allow the use of bacterial specific tracers and when combined with imaging modalities such as positron emission tomography (PET), have the ability to delineate infective from sterile sites. This approach, however is not be applicable for some patient groups, such as intensive care cohorts where a point of care diagnostic test would be required, and the administration of radioactive agents can be problematic and restrictive. These also involve radiation and are not readily applicable to imaging outside hospital settings.

An alternative approach in the art is the application of optical probes to allow direct visualisation of a target area of a patient, through the use of an endoscope. WO 2003/079015 in the name of Visen Medical, Inc., discloses optical imaging probes for identifying and characterising normal and diseased tissues with regards to altered metabolic activity.

WO 2012/136958 in the name of the present applicant discloses branched dyes to allow visualisation of cells in vivo by an increase in fluorescence when the dye is internalised by specific cell types.

However, there remains a need for improved optical probes and imaging methods that will allow in situ, point of care determination of whether a patient's condition is due to an infection, and if so, what is the causative agent of the infection.

Furthermore, there remains a need for improved optical probes that are retained at the target cell membrane, for example, during challenging conditions, such as in the presence of surfactants.

Therefore, an object of the present invention is to provide improved probes and imaging methods suitable for rapid and accurate point of care diagnosis, and to provide optical probes that are better retained by their target.

STATEMENTS OF THE INVENTION

According to a first aspect of the invention, there is provided a probe comprising a core and a plurality of probe elements; each probe element within the plurality of probe elements extending from the core and comprising a fluorophore and a binding moiety.

During use, the probes of the invention are typically delivered to a target area and bind to any bacteria within the target area. Preferably, the binding moiety of each of the plurality of probe elements is available to bind to bacteria, and therefore, if bacteria is present in the target area, the probe is bound to the bacteria by each, or at least the majority, of the binding moieties of the plurality of probe elements.

Optical probes known in the art are typically retained poorly in a target area in vivo where challenging conditions can lead to degradation or oxidation of the probes, and/or protease breakdown, and as a result, the probes are unable to remain bound to their target to allow reliable detection of the target. For example, optical probes used for imaging within the lung where there are high surfactant concentrations, typically do not allow their targets to be detected. Further challenges within the lung include "washing off" of probes by the circulating fluid therein.

Surprisingly, the inventors have found that the probes of the invention are more stable to oxidation, degradation and protease activity than probes known in the art, and that such probes allow reliable detection of bacteria in vivo, even in challenging conditions such as those found in the lung.

By the term "core" we refer to a common moiety that joins the plurality of probe elements to form a single unit.

Accordingly, the core could be a single atom, or comprise a functional group, a saturated or unsaturated hydrocarbon chain or a polyglygol (linear, branched, or cyclical), a peptide sequence, or a polymer.

Preferably, the plurality of probe elements comprises at least two probe elements, at least three probe elements, at least four probe elements or at least five probe elements. For example, the plurality of probe elements may comprise three probe elements.

The binding moiety may selectively bind to at least some bacteria, and not bind to animal cells, such as mammalian cells, for example, or does so weakly. Accordingly, the binding moiety may be a bacteria binding moiety. The bacteria binding moiety may bind to substantially all bacteria but not to animal cells, or does so weakly. The bacteria binding moiety may selectively bind to substantially gram-negative bacteria, but not bind to gram-positive bacteria, or animal cells such as mammalian cells, or does so weakly.

The binding moiety may selectively bind to fungi, and not bind to animal cells, such as mammalian cells, for example. Accordingly, the binding moiety may be a fungi binding moiety and may bind to fungi hyphae.

The binding moiety may selectively bind to at least some bacteria and to at least some fungi, and not bind to animal cells such as mammalian cells. Accordingly, the probe may allow the detection of fungi and/or bacteria in a target area. For example, the binding moiety may be adapted to bind to fungal hyphae of A. fumigatus.

The binding moiety of one or more of the probe elements may be a ubiquicidin moiety, such as the full length ubiquicidin (SEQ ID NO.1) or a fragment or variant thereof. The binding moiety may be a fragment of ubiquicidin comprising at least 10 consecutive amino acids, or at least 12 consecutive amino acids of ubiquicidin. For example, the binding moiety may be the ubiquicidin fragment of amino acids 29 to 41 ($UBI_{29-41}$, SEQ ID NO.2). The binding moiety may be a ubiquicidin moiety comprising one or more substitutions. The or each substitution may be a conservative substitution, and have little or preferably, no effect on the bacteria binding properties of the ubiquicidin. The or each substitution may provide stability to the ubiquicidin moiety against degration or oxidation. For example, the binding moiety may be $UBI_{29-41}$ comprising a substitution of a norleucine amino acid for the original methionine amino acid ($UBI_{29-41Nle}$, SEQ ID NO.3).

Ubiquicidin is a mammalian anti-microbial peptide present in airway epithelial cells, gut mucosa and in macrophages. Ubiquicidin binds specifically to the cell membrane of prokaryotes such as bacteria and does not bind to mammalian cells.

The binding moiety of one or more of the probe elements may selectively bind to gram positive bacteria and may not substantially bind to gram-negative bacteria. Preferably, the binding moiety of one or more of the probe elements selectively binds to gram-negative bacteria and does not substantially bind to gram-positive bacteria. Accordingly, in embodiments where the binding moiety of one or more of the probe elements selectively binds to gram-negative bacteria, the probe of the invention may be randomly distributed in a target area that does not comprise gram-negative bacteria, and be localised to the cell membranes of any gram-negative bacteria present in the target area. Therefore, the probe of the invention may be adapted to selectively indicate the presence, or absence, of gram-negative bacteria in a target area.

For example, the binding moiety of one or more of the probe elements may be a polymyxin moiety, such as full length polymyxin (SEQ ID NO.4), or a fragment or variant thereof. Polymyxin binds selectively to gram negative bacteria, and therefore, a bacterial binding moiety comprising a polymyxin moiety will selectively bind the respective probe element to gram negative bacteria only, and thereby allow detection of any gram negative bacteria within the target area. The binding moiety may be a fragment of polymyxin comprising at least 6 consecutive amino acids, or at least 8 consecutive amino acids of polymyxin. The binding moiety may be a polymyxin moiety comprising one or more substitutions. The or each substitution may be a conservative substitution, and have little or preferably, no effect on the gram-negative bacteria binding properties of the polymyxin moiety. The or each substitution may provide increased stability to the polymyxin moiety against degradation or oxidation.

The binding moiety may be adapted to bind to at least some fungi. The binding moiety may be adapted to bind to fungal hyphae. For example, the binding moiety may be adapted to bind to fungal hyphae of A. fumigatus.

Accordingly, the probe of the invention may be used to label fungi. For example, the probe of the invention may be delivered to a target area and the probe may bind to any bacteria or fungi hyphae in the target area. Upon illumination of the target area with an appropriate wavelength of light to excite the or each fluorophore of the plurality of bacteria binding probes, any bacteria and/or fungi within the target area will be labelled. The bacteria may be differentiated from the fungal hyphae visually, for example.

Therefore, the probe of the invention, may be used to determine bacterial or fungal infections, for example.

Preferably, each probe element within the plurality of probe elements comprises the same fluorophore.

However, alternative embodiments of the invention may comprise probe elements having different fluorophores. For example, a probe of the invention may comprise three probe elements, and the first probe element may comprise a first fluorophore, the second probe element may comprise a second fluorophore and the third probe element may comprise a third fluorophore.

Preferably, the fluorophore of each probe element within the plurality of probe elements is an environmentally sensitive fluorophore, such that the intensity or quantum yield of fluorescence of the fluorophore depends on the surroundings of the fluorophore. For example, the quantum yield or intensity of the fluorophore may be different in a free aqueous environment than when the fluorophore is in a hydrophobic environment, such as within a cell membrane. Preferably, the quantum yield or intensity of the fluorophore is higher in a hydrophobic environment, such as within a cell membrane. Accordingly, the intensity of light emitted by the fluorophore increases when the fluorophore is at least partially within a cell membrane, such as when the probe element is bound within a cell membrane of bacteria, for example. Therefore, the fluorophore may be used to fluorescently label cells via their cell membranes.

The fluorophore of one or more of the probe elements within the plurality of probe elements may be 7-nitrobenz-2-oxa-1,3-diazole (NBD), malachite green, a styryl-based dye, Cascade Yellow, prodan (aka 1-Propanone, 1-(6-(dimethylamino)-2-naphthalenyl), Dansyl (aka. 5-(dimethylamino)naphthalene-1-sulfonyl), Dapoxyl, PyMPO (aka. 1-(3-(Succinimidyloxycarbonyl)Benzyl)-4-(5-(4-Methoxyphenyl)Oxazol-2-yl)Pyridinium, pyrene and diethylaminocumarin, or derivatives or variants thereof.

Preferably, the fluorophore of at least one probe element within the plurality of probe elements is a NBD moiety.

More preferably, the fluorophore of each probe element within the plurality of probe elements is a NBD moiety. NBD has been found by the inventors to be a particularly suitable fluorophore for the probe of the invention, providing strong fluorescence when the probe is bound to bacteria, and a low background fluorescence, allowing clear and reliable labelling of bacteria compared to other fluorophores tested.

The fluorophore of one or more of the probe elements within the plurality of probe elements may have a long fluorescent lifetime and the long fluorescent lifetime of the fluorophore allows the detection of the probe over background autofluorescence. For example, during use, the fluorescence of the fluorophore may have a lifetime significantly longer than the autofluorescence of the background of a target area such that the fluorescence from the fluorophore is readily distinguishable from the fluorescence of the background.

For example, the fluorophore is azadioxatriangulene (ADOTA) dye or diazaoxatriangulene (DAOTA), or derivatives thereof.

Suitably, one or more fluorophores of adjacent probe elements within the plurality of probe elements may quench the fluorescence of one or more of the other fluorophores of the probe. Therefore, the fluorophores of the probe may self-quench.

Preferably, in embodiments where the one or more fluorophore of adjacent probe elements within the plurality of probe elements self-quench, the self-quenching is prevented or reduced when the environment of the probe is changed. For example, the inventors have surprisingly found that in embodiments where the fluorophore of each probe element of the plurality of probe elements is NBD, the probe emits low or no significant fluorescence in an aqueous environment due to the NBD moieties self-quenching, but surprisingly, when the probe is in a hydrophobic environment, such as within a cell membrane, the NBD moieties are no longer able to self-quench and the probe fluorescence is high. Accordingly, the probe of the invention may selectively fluoresce only when it is bound to bacteria, and therefore, provides a relatively low background fluorescence. Advantageously, this selective self-quenching of the fluorophores within the probe improves the signal to noise ratio within the target area and provides clearer and more reliable detection of bacteria. Furthermore, due to the higher concentration of fluorophores on the probe (a plurality of fluorophores compared to a single fluorophore), the fluorescent signal produced by probe when bound is higher, further improving the signal to noise ratio.

The binding moiety may be at the distal end of the probe element furthest from the core.

The binding moiety may be at the proximal end of the probe element and adjacent to the core, and the fluorophore of the probe element may connect to the core via the binding moiety. Alternatively, the binding moiety and the fluorophore of a probe element may be connected to the core by a common connector and each of the binding moiety and the fluorophore may extend away from the connector.

The fluorophore may be connected to the binding moiety directly. Alternatively, the fluorophore may be connected to the binding moiety by a spacer. The spacer may be a saturated or unsaturated hydrocarbon chain, an ether, a polymer, a polyethylglycol (PEG), a poly glycol, a poly ether or similar. The spacer may be a peptide. In embodiments where the spacer is a peptide, the peptide may be 1-10 amino acids in length, 1-20 amino acids in length, or 1-30 amino acids in length.

The probe may comprise a quencher connected to the core by a cleavable linker; the fluorophore of one or more of the probe elements within the plurality of probe elements may be substantially fluorescently quenched by the quencher when the core is connected to the quencher by the cleavable linker; wherein the core, and thereby the plurality of probe elements, is separated from the quencher when the cleavable linker is cleaved.

In embodiments where the fluorophores of the probe do not self-quench, the provision of a quencher that may be separated from the fluorophores by cleavage of the linker allows the fluorophores to be quenched unless a cleaving agent is present, which cleaves the linker. Accordingly, the probe may allow detection of the presence of the cleaving agent by significant fluorescence of the fluorophores of the probe.

Preferably, the linker is dimensioned such that the quencher is sufficiently close to the fluorophore of at least one of the plurality of probe elements to quench the fluorophore. Typically, the quencher is less than 10 nm away from the fluorophore of at least one of the probe elements. Preferably, the quencher is less than 5 nm away from the fluorophore of at least one of the probe elements.

Preferably, the cleavable linker comprises an enzyme cleavable peptide sequence, and the linker is cleaved when a cleaving enzyme cleaves the enzyme cleavable peptide sequence.

Accordingly, cleavage of the enzyme cleavable peptide sequence typically corresponds to cleavage of the linker, and thereby cleavage of the quencher from the probe element. Accordingly, in embodiments where the cleavable linker comprises an enzyme cleavable peptide sequence, the term "cleavage of the linker" refers to cleavage of the enzyme cleavable peptide sequence unless stated otherwise.

The cleaving enzyme may be produced or expressed by the indigenous cells within the target area. The cleaving enzyme may be produced or expressed by additional cells produced by the patient that have migrated to the target area, such as leukocytes, for example neutrophils. The cleaving enzyme may be produced or expressed by an infective agent in the target area, such as a bacterial or fungal cell, for example.

Preferably, the cleaving enzyme is elastase and cleavage of the enzyme cleavable peptide sequence is indicative of the presence of elastase. Typically, the elastase is neutrophil elastase and the elastase is produced or expressed by neutrophils. Typically, the elastase is the active form of the enzyme capable of proteolytic cleavage. Neutrophils typically target sites within the body that are undergoing an inflammatory response, either pathophysiologically or part of normal function. Therefore, the presence of neutrophils in a target area within a patient is indicative that the tissue or a portion of the tissue within the target area is inflamed.

Therefore, an increase in fluorescence, or fluorescence of the fluorophore of at least one of the probe elements resulting from the separation of the quencher and fluorophore by cleavage of the linker, is indicative of the presence of neutrophil elastase. Neutrophil elastase is produced by neutrophils, and therefore the presence of neutrophil elastase is indicative of the presence of neutrophils and therefore, inflammation of the tissue within the target area. Accordingly, the probe of the invention may be adapted to indicate inflammation of tissue within a target area.

Human elastase, such as human neutrophil elastase (HNE), and other elastases or other enzymes such as proteases, typically have one or more target sequences to which they bind and cleave. Accordingly, the enzyme cleavable peptide sequence will typically comprise the or a target peptide sequences of the cleaving enzyme to be detected, and the person skilled in the art would be able to select an appropriate peptide sequence for a given cleaving enzyme.

Typically, the enzyme cleavable peptide linker is a peptide sequence that is a or the cleavage site of the cleaving enzyme. Preferably, the or each cleavage site of the cleaving enzyme comprises multiple amino acids. In embodiments where the cleaving enzyme is elastase, preferably, the enzyme cleavable peptide sequence comprises the amino add sequence AAPV (SEQ ID NO: 9) (i.e. alanine-alanine-proline-valine, or Ala-Ala-Pro-Val) or EEINleRR (SEQ ID NO: 10). The enzyme cleavable peptide sequence may comprise one or more additional amino adds either side of the sequence AAPV (SEQ ID NO: 9) in positions x and/or y, such as xAAPVy (SEQ ID NO: 11), xAAPV (SEQ ID NO: 12), or AAPVy (SEQ ID NO: 13), for example.

Alternatively, the cleaving enzyme may be e matrix metalloproteinase (MMP), such as MMP-9, and the enzyme cleavable peptide sequence may comprise G-P-K-G-L-K-G (SEQ ID NO: 14). The cleaving enzyme may be proteinase 3 and the enzyme cleavable peptide sequence may comprise V-A-D-C-A-D-Y (SEQ ID NO: 15). The cleaving enzyme may be cathepsin G and the enzyme cleavable peptide sequence may comprise A-A-P F (SEQ ID NO: 16), or F-V-T-Gnf-S-W (SEQ ID NO: 17 (where Gnf=4-guanidine-L-phenylalanine). The cleaving enzyme may be a caspase and the enzyme cleavable peptide sequence may comprise D-E-V-D (SEQ ID NO: 18).

In alternative embodiments, the cleavable linker may be cleaved by a reactive oxygen species, such as superoxide ($O_2^-$) or hydrogen peroxide ($H_2O_2$), generated by the presence of bacteria, or inflammation processes such as activated neutrophils. Accordingly, a reactive oxygen species may be a cleaving agent. For example, the linker may be a modified boronic acid based linker, such as that described in J. Am. Chem. Soc, 2014, 874, Roger Y. Tsien.

Optical probes known in the art typically are either fluorescent at all times (so-called "always on" fluorophores), and it is the location of these probes that is determined, or the probes change their fluorescence when their environment is changed, be that the removal or separation of a quencher (for fluorescence resonance energy transfer, or FRET, based probes, for example), or being internalised by a cell.

However, in embodiments where the plurality of fluorophores of the plurality of probe elements do not self-quench, and the probe comprises a cleavable linker, the probe of the invention advantageously changes its fluorescence due to whether the cleavable linker has been cleaved by the cleaving agent, and the location of the probes when observed can indicate the presence of bacteria. Accordingly, the probes of the invention are able to provide specific and more detailed information than optical probes known in the art. For example, the probes are adapted to indicate whether the cleaving agent is present (if the probe fluoresces, or the colour of fluorescence changes the cleavable linker has been cleaved by the cleaving agent) and, if the cleaving agent is present, whether bacteria and/or fungi is present, indicated by the localisation of the probe to the bacteria and/or fungi hyphae and an increase in fluorescence of the probe, for example.

The quencher may be a dark quencher. A dark quencher is a moiety that is able to accept energy from an excited fluorophore and dissipate that energy non-radiatively, typically as heat or acoustic energy, for example. Therefore, when the fluorophore/quencher pair are sufficiently close together and are irradiated with a wavelength of light that is within the excitation spectra of the fluorophore, the quencher dissipates the energy absorbed from the light by the fluorophore in a non-radiative manner and no fluorescence is observed. In this way, the dark quencher suppresses the fluorescence of the fluorophore.

In embodiments where the quencher is a dark quencher, the quencher may be methyl red, dimethylaminoazobenzenesulfonic acid (DABSYL), Iowa black FQ or Iowa black RQ (Integrated DNA Technologies, Inc. Iowa, USA), BHQ1, BHQ2 or BHQ3, for example.

The quencher may be a fluorescent quencher. A fluorescent quencher is a moiety that is able to accept energy from an excited fluorophore and to radiate that energy. Accordingly, fluorescent quenchers are typically fluorophores, and emit light at a different wavelength to that emitted by the fluorophore from which they have accepted energy. In this way, the change in colour of fluorescence is indicative of the relative proximity of the quencher to the fluorophore.

In embodiments where the quencher is a fluorescent quencher, the quencher may be rhodamine, tetramethylrhodamine or a derivative thereof, such as carboxytetramethylrhodamine (TAMRA) for example, fluorescein, or a derivative thereof, cyanine fluorophores or boron-dipyrromethene (BODIPY) fluorophores.

In embodiments where the quencher is a fluorescent quencher, the quencher may be adapted to label neutrophils. Accordingly, in embodiments where the cleavable linker comprises an enzyme cleavable peptide sequence, the probe of the invention may be adapted to indicate the presence of a cleaving enzyme, such as elastase, to label the neutrophils that are producing the enzyme, and to label any bacteria that may be present.

For example, in embodiments where the cleaving enzyme is neutrophil elastase, the fluorescent quencher may be taken up by neutrophils that are activated by the presence of bacteria or by stimuli such as calcium ionophore, for example. Accordingly, the fluorescent quencher may selectively label neutrophils within the target area. The inventors have observed that fluorescent quenchers, such as TAMRA, are selectively taken up by neutrophils and are not taken up, or are taken up to a much lesser extent, by bacteria and by other inflammatory cells, such as monocytes, and the inventors speculate that this observed difference in uptake of the fluorescent quencher may be due to the higher endocytic and pinocytic activity in highly phagocytic cells such as neutrophils.

The fluorophore of the probe element may form a FRET pair with the quencher. Typically, the fluorophore and the quencher are chosen as a pair to ensure that they have appropriate excitation and emission spectra for the transfer of energy from the fluorophore to the quencher (i.e. they form a FRET pair). For example, typical fluorophore/quencher pairs include Cy3/Cy5, Cy3/QSY21, fluorescein/tetramethylrhodamine, fluorescein/methyl red, cyan fluorescent protein (CFP)/yellow fluorescent protein (YFP), etc. Further examples of FRET pairs may be readily identified by the skilled person.

In embodiments where the fluorophore of at least one of the probe elements within the plurality of probe elements is NBD, the quencher is preferably a moiety that is able to accept energy from NBD to form a FRET pair with the NBD. Preferably, the quencher is methyl red or tetramethylrhodamine or a derivative thereof. For example, the quencher may be carboxytetramethylrhodamine (TAMRA).

In embodiments comprising a cleavable linker, the binding moiety may bind to bacteria and/or fungi prior to cleavage of the cleavable linker. Alternatively, the binding moiety may bind to bacteria and/or fungi after cleavage of the cleavable linker.

For example, the probe of the invention may be delivered to a target area and the probe may bind to any bacteria or fungal hyphae in the target area. Upon illumination of the target area with an appropriate wavelength of light to excite the fluorophore of the probe element, any bacteria and/or fungi within the target area will be labelled. The bacteria may be differentiated from the fungal hyphae visually, for example.

Typically, the probes of the invention are operable to be used to detect bacteria and/or inflammation in the target area. The target area may be a portion of tissue within a patient, and the method may be carried out in vivo. For example, the target area may be a portion of the lung of a patient, and the method may be carried out using a bronchoscope to both deliver the probe to the target area, to deliver light to the target area, and to detect fluorescence from the target area. Alternatively, individual instruments may be used to deliver the probe to the target area, to deliver light to the target area and to detect fluorescence from the target area.

For example, fluorescence may be detected from the tissue of a patient using optical emission microscopy (OEM), such as fibered confocal fluorescence microscopy (FCFM).

The target area could be on the skin of a patient, in joints, in the circulatory system, the digestive system or the reproductive system, and the probes may be delivered and/or observed via an endoscope, for example.

Alternatively, the target area may be a portion of a cell culture, a tissue sample such as a biopsy sample, or a liquid sample such as a bodily fluid sample, and the method may be carried out in vitro.

Preferably, the patient is a human patient. However, the patient may be a non-human animal such as equine, ovine, bovine, or rodents, for example.

The probe may comprise a secondary label. For example, the core of the probe may comprise a secondary label, or one or more of the plurality of probe elements may comprise a secondary label. The secondary label may be a fluorophore. The fluorophore of the secondary label may be different to the fluorophore of the or each probe element. The secondary label may be a radioactive label. The radioactive label may comprise a radionucleotide. The radioactive label may comprise one or more of $^{18}F$, $^{64}Cu$, $^{68}Ga$, $^{99}Tc$, $^{111}In$, $^{123}I$, $^{124}I$, $^{90}Y$, $^{177}Lu$, $^{11}C$, $^{14}C$, $^{3}H$, $^{32}P$, $^{33}P$, $^{186}Re$, $^{188}Re$, or $^{86}Zr$. The secondary label may be a magnetic resonance label or core. The magnetic resonance label or core may be Fe, Mn, or Gd, for example.

Accordingly, the probe may have dual- or multi-modality, and may be used in optical imaging, radioactive imaging, or in magnetic resonance imaging.

In further embodiments, the probe may comprise a targeting element that is adapted to be internalised by a target species. The targeting element may comprise a fluorophore. The fluorophore of the targeting element may be adapted to be internalised by the target species. For example, a probe may comprise Cy5 and the probe, or a portion of the probe comprising the Cy5 once the linker has been cleaved, may be internalised by any neutrophils in the target area to label them. Typically, the probe comprises a quencher for the targeting element, and the targeting element is separated from the quencher by the linker. In some embodiments, the probe may comprise a first portion and a second portion connected by the linker. The first portion may comprise the probe element and the quencher of the targeting element, and the second portion may comprise the targeting element and the quencher for the probe element. Accordingly, when the linker is cleaved, the probe element and the targeting element are both separated from their respective quenchers.

For example, the probe element may comprise NBD (fluorophore) and QSY21, BHQ3 or BBQ650 (quenchers), and the targeting element may comprise Cy5, or sulfonated Cy5 (fluorophore) and methyl red or BHQ1 (quenchers).

Each probe element of the plurality of probe elements may extend from the core such that the probe is a branched, or multivalent probe, with each probe element forming a separate branch of the probe. For example, the probe may have one of the following structures:

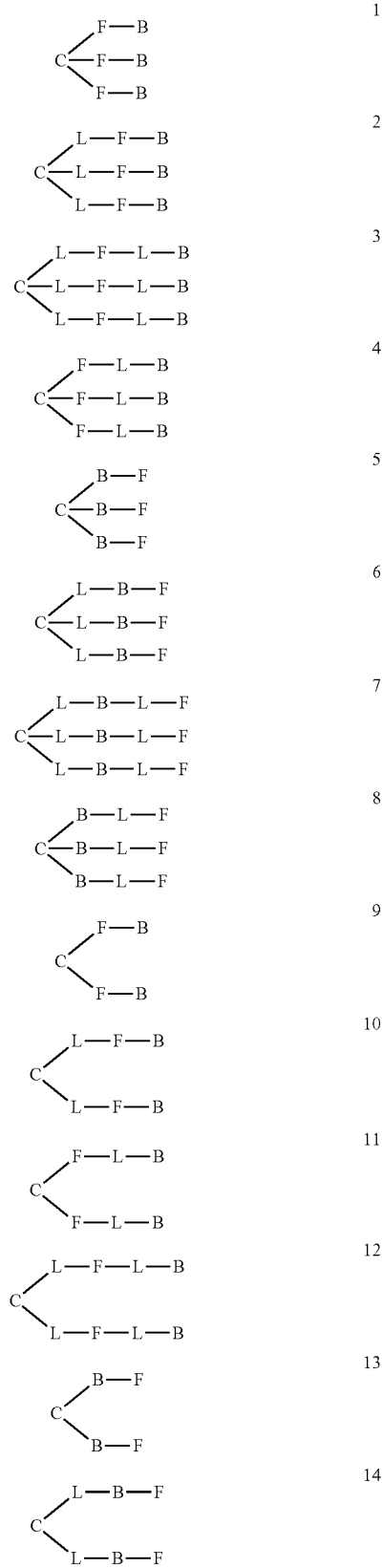

-continued

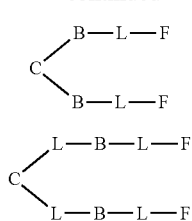

where
L=spacer group (e.g. $C_3$-$C_{10}$ alkyl, $((CH_2)_2O)_x$ where x=1-6)
F=fluorophore (e.g. NBD, fluorescein)
B=binding moiety (e.g. ubiquicidin moiety, polymyxin moiety)
C=core (e.g. carbon, —$C(CH_2O(CH_2)_3)_3$, $NH_2CONHC(CH_2O(CH_2)_3)_3$)

For example, in a preferred embodiment, the probe comprises three probe elements connected to a core, and has the general formula $NH_2CONHC(CH_2O(CH_2)_3$-NBD-$(CH_2)_5$-$UBI_{Nle})_3$ where the core is $NH_2CONHC(CH_2O(CH_2)_3)_3$ and each probe element is:

NBD-$(CH_2)_5$CO-$UBI_{Nle}$;

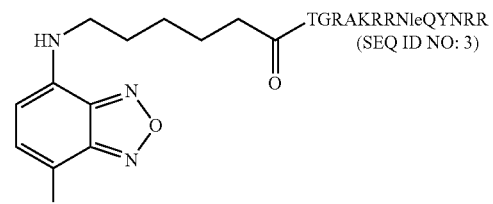

In an alternative embodiment, each of the three probe elements is NBD-$(CH_2)_2O(CH_2)_2OCH_2$-PMX;

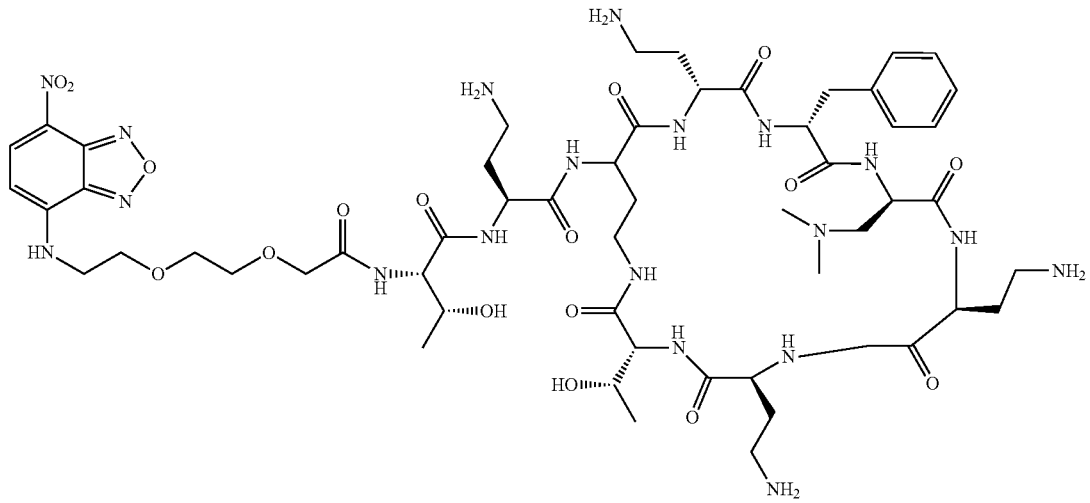

The probe may have the structure (SEQ ID NO: 3):

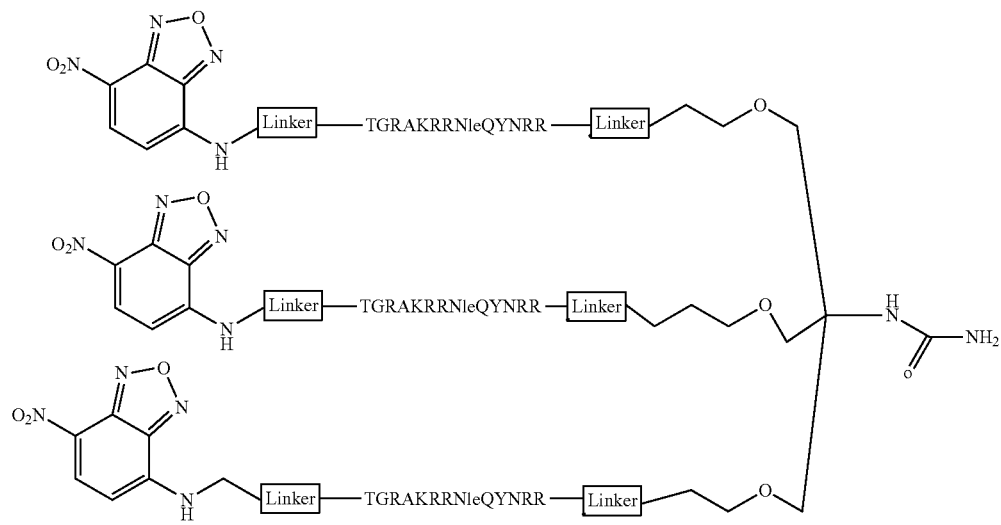

A preferred embodiment of the probe has the structure:

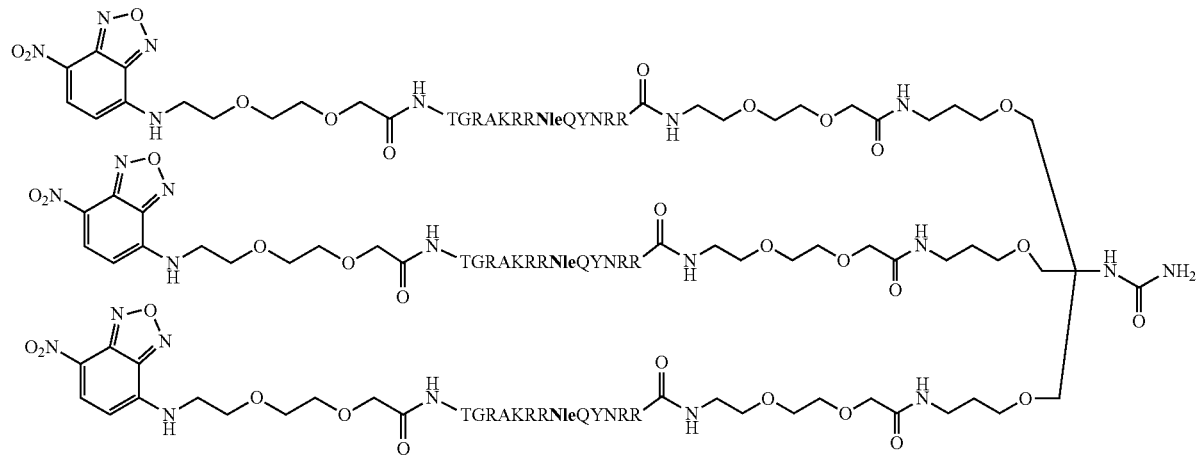

According to a second aspect of the invention there is provided a method of detecting bacteria and/or fungi in a target area, the method comprising the steps:
(1) providing a first probe according to the first aspect of the invention;
(2) delivering the first probe to the target area;
(3) illuminating the target area with an appropriate wavelength of light to excite the fluorophores of the first probe; and
(4) determining whether the first probe has labelled bacteria and/or fungi within the target area.

Labelling of bacteria and/or fungi by the first probe within the target area is indicative of the presence of bacteria and/or fungi in the target area.

The target area may be tissue within a patient, and the method may be carried out in vivo. For example, the target area may be lung tissue of a patient, and the method may be carried out using a bronchoscope to both deliver the probe to the target area, to deliver light to the target area, and to detect fluorescence from the target area. Alternatively, individual instruments may be used to deliver the first probe to the target area, to deliver light to the target area and to detect fluorescent from the target area.

The target area may be a cell culture, a tissue sample such as a biopsy sample, or a liquid sample such as a bodily fluid sample, and the method may be carried out in vitro.

Preferably, the patient is a human patient. However, the patient may be a non-human animal such as equine, ovine, bovine, or rodent, for example.

In embodiments of the invention where the probe according to the first aspect comprises a cleavable linker, the cleaving agent may be a cleaving enzyme. The cleaving enzyme may be elastase, and significant fluorescence of the fluorophore of the probe element of the first probe may be indicative of the presence of the cleaving enzyme that cleaves the linker. In embodiments where the patient is a human patient, the cleaving enzyme is preferably human neutrophil elastase (HNE). HNE is typically produced or expressed by neutrophils at the site of tissue inflammation. Accordingly, the presence of HNE is indicative of inflammation of the surrounding tissue. Therefore, in embodiments where the cleaving enzyme is HNE, significant fluorescence of the fluorophores of the plurality of probe elements of the first probe is indicative of inflammation within the target area. For example, where the target area is within lung tissue of a patient, significant fluorescence of the fluorophores is indicative of inflammation of the lung tissue.

The method may allow detection of both sterile inflammation (i.e. inflammation that is not caused by infection) and infective inflammation (i.e. inflammation that is caused by a foreign body such as bacteria, or fungi, for example). Typically, significant fluorescence of the first probe without labelling of bacteria or fungi is indicative of sterile inflammation, and significant fluorescence of the probe with labelling of bacteria is indicative of bacterial inflammation. Significant fluorescence of the probe with labelling of fungi hyphae is indicative of fungal inflammation.

By the term "significant fluorescence" we refer to the fluorescence of the fluorophore that may result from sufficient separation of that fluorophore from the quencher of the first probe to prevent the quencher quenching the fluorescence of the fluorophore, that is above the background or, where present, autofluorescence in the target area. The autofluorescence of the indigenous cells or tissue within the target area may have a shorter fluorescent lifetime than the fluorophore of the first probe. The autofluorescence of the indigenous cells or tissue within the target area may reduce over time at a faster rate than that of the fluorophore of the probe. Accordingly, fluorescence observed in the target area that reduces more slowly over time may be indicative of the first probe, and fluorescence observed in the target area that reduces more quickly over time may be indicative of autofluorescence.

In many areas of healthcare, such as critical or intensive care, it is not typically possible to use standard methods such as PET scans to identify whether inflammation of the lungs, for example, is sterile or infective, as the patients cannot be safely moved, especially when those patients are being ventilated. Accordingly, clinicians do not have sufficient information to confidently diagnose the inflammation and prescribe a suitable corrective course of action. For example, if the inflammation is sterile, giving the patient antibiotics will not help, and may have adverse side effects.

The method of the invention may be carried out by a clinician in situ at the point of care, and determines whether bacteria and/or fungi is present in a target area, such as within the lungs, or a portion of the lungs of the patient. Accordingly, the method of the invention provides the clinician with the information they need to confidently determine the cause of any inflammation, and to determine the best course of action, such as giving an antibiotic to the patient, for example.

If bacteria is detected in the target area, and an appropriate antibiotic is given to the patient, the method may be carried out to determine the efficacy of the antibiotic. For example, a reduction in the number of bacteria, or the absence of bacteria in the target area typically indicates that the course of treatment is effectively clearing the bacterial infection. Similarly, if fungi is detected in the target area and an appropriate antifungal agent is given to the patient, the method may be carried out to determine the efficacy of the antifungal.

The method may comprise the step of providing a second probe according to the first aspect comprising a binding moiety that specifically binds to a subpopulation of bacteria. For example, the binding moiety of the second probe may bind to gram-negative bacteria specifically or may bind to gram-positive bacteria specifically.

The method may comprise the step of (5) delivering the second probe to the target area. The method may further comprise the step of (6) illuminating the target area with an appropriate wavelength of light to excite the or each fluorophore of the second probe. Step (5) and step (6) may be carried out after step (4), and the first probes may be allowed to dissipate or otherwise be removed from the target area between step (4) and step (5). In this way, when the target are is illuminated in step (6), substantially only the second probe will be in the target area and therefore, any fluorescence observed may be attributed to the second probe. Therefore, the or each fluorophore of the second probe may the same or a different fluorophore to that of the first probe.

Alternatively, step (5) may be carried out between step (2) and step (3), and step (3) corresponds to step (6). Accordingly, both the first probe and the second probe are present in the target area when the target area is illuminated. Therefore, preferably a or each fluorophore of the second probe is different to that of the first probe such that the fluorescence from the first probe and the fluorescence of the second probe are of different wavelengths, and can therefore, be differentiated from one another. The provision of different fluorophores for each of the first probe and the second probe allows the presence of any bacteria and/or fungi in the target area (shown by the localisation of the first probe to the cell walls of the bacteria or fungal hyphae), and whether any bacteria are gram negative or gram positive (shown by whether the second probe has localised to the cell walls of the bacteria) to be determined. In embodiments where the probe comprises an enzyme cleavable peptide linker connecting a quencher to the core of the probe, the method of the invention allows the presence of inflammation to be determined (shown by the significant fluorescence of the first and/or second probes), the presence of any bacteria and/or fungi in the target area (shown by the localisation of the first probe to the bacteria or fungal hyphae), and the determination of whether the bacteria are gram-negative or gram-positive (shown by whether the second probe has labelled the bacteria).

Therefore, the method of the present aspect of the invention may advantageously allow the cause of inflammation in a single test to be identified, and in some embodiments, the determination of the presence of sterile inflammation, thereby providing healthcare professionals with the information they need in order to decide on the correct course of action for that patient.

The method may comprise the step of observing the target area under white or fluorescent light to determine the morphology of any infective agent (bacteria or fungi) identified in the target area. The method may comprise the step of observing the target area under white or fluorescent light to identify microbes within the target area, and the first and second probes may be used to determine the identity of those microbes.

Fluorescence from the first and/or second fluorophore may be imaged directly by the fluorescence emitted from the first and/or second fluorophore being directed onto a detecting device, such as a charge-coupled device (CCD) or a complementary metal-oxide-semiconductor (CMOS) device, for example. Fluorescence from the first and/or second fluorophore may be imaged indirectly. For example, the fluorescence may be converted into acoustic waves by using photoacoustic imaging. Photoacoustic imaging may allow high-resolution images of the target area to be generated. In embodiments where the first and/or second fluorophore emit light in the near-infrared or infrared range of wavelengths (~700 nm-1 mm), the whole or substantially the whole, of the body of the patient may be imaged. Alternatively, in embodiments where the first and/or second fluorophore emit light in the visible range of wavelengths (~390 nm-700 nm), a specific target area of the patient may be imaged, and the light may be delivered to and received from the target area via a fibre optic, for example.

The method may comprise the step of observing the target area using photoaccoustic ultrasound to determine the identity of the infective agent (bacteria or fungi) detected in the target area. The method may comprise the step of observing the target area using photoaccoustic instruments to identify microbes within the target area, and the first and second probes may be used to determine the identity of those microbes using direct fluorescent detection.

The first probe may comprise a ubiquicidin moiety, such as full length ubiquicidin, or a fragment or variant thereof as the binding moiety.

The second probe may comprise a polymyxin moiety, such as full length polymyxin or a fragment or variant thereof, as the binding moiety, and the second probe may selectively bind to gram negative bacteria.

Accordingly, the method may allow the identification of sterile inflammation, bacterial and/or fungal inflammation, and gram negative bacterial infection (and by inference, gram positive bacterial infection).

The invention extends in a third aspect to use of the probes of the first aspect to identify or label bacteria and/or fungi in a target area.

The probes may be used in vivo to identify or label bacteria and/or fungi in a target area. For example, the probes may be used in vivo in embodiments where the target area is a portion of tissue within a patient, such as lung tissue of a patient.

In embodiments where the probes are used in vivo, a bronchoscope or endoscope may be used to both deliver the probe to the target area, to deliver light to the target area, and to detect fluorescence of the probes within the target area. Alternatively, individual instruments may be used to deliver the first probe to the target area, to deliver light to the target area and to detect fluorescent from the target area.

The probes may be used in vitro to identify or label bacteria and/or fungi in a target area. For example, the probes may be used in vitro in embodiments where the target area is a portion of a cell culture, a tissue sample such as a biopsy sample, or a liquid sample such as a bodily fluid sample.

In embodiments where the probes are used in vitro, fluorescence from the probes may be detected using microscopy, such as confocal microscopy, for example.

A first probe of the first aspect may be used to identify or label bacteria and/or fungi in a target area, and a second probe according to the first aspect may be used to determine whether the identified or labelled bacteria are gram-negative or gram-positive bacteria, wherein at least one binding moiety of the first probe binds specifically to bacteria and/or fungi, and at least one binding moiety of the second probe binds specifically to gram-negative or gram-positive bacteria. For example, at least one binding moiety of the first probe may be a ubiquicidin moiety, and at least one binding moiety of the second probe may be a polymyxin moiety.

According to a fourth aspect of the invention, there is provided a kit of parts comprising one or more probes of the first aspect of the invention and a suitable buffer within which the probe may be dispersed.

The kit of parts may comprise a first probe according to the first aspect comprising at least one binding moiety that specifically binds to bacteria and/or fungi, and a second probe of the first aspect comprising at least one binding moiety that specifically binds to gram-negative or gram-positive bacteria.

For example, the kit of parts may comprise a first probe comprising at least one ubiquicidin moiety, and a second probe comprising at least one polymyxin moiety.

Optional and preferred features of the first aspect are optional and preferred features of the second, third and fourth aspects.

Embodiments of the present invention will now be described, by way of non-limiting example, with reference to the accompanying drawings.

*aureus* or GFP-expressing strain of *S. aureus*, generate a punctate pattern of fluorescence when segments are imaged using FCFM. Images used to generate positive control for subsequent in situ labelling experiments. Representative images shown, n=3 for all experiments. B) PKH dyes do not stain by-stander cells. Confocal images showing epithelial cells in co-culture with bacteria (*S. aureus*) that have been counterstained with Syto-82 (bottom left image red) as well as PKH660 (too left image). Bystander mammalian cells (arrows) are labelled with Syto-82 that has leached from the labelled bacteria but there is no transfer of PKH660.

Figure 8:
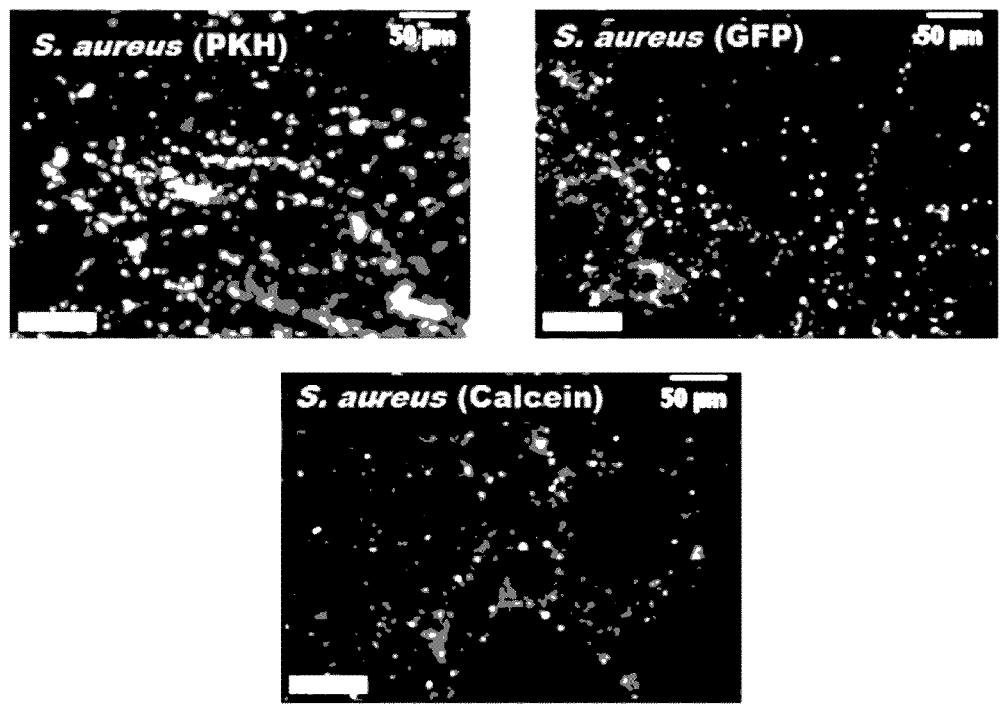
FIG. 8: Representative FCFM images of bacteria in the distal lung demonstrating a distinctive punctate pattern. A) Instillation of PKH labelled S. aureus, Calcein labelled S.
Figure 8:
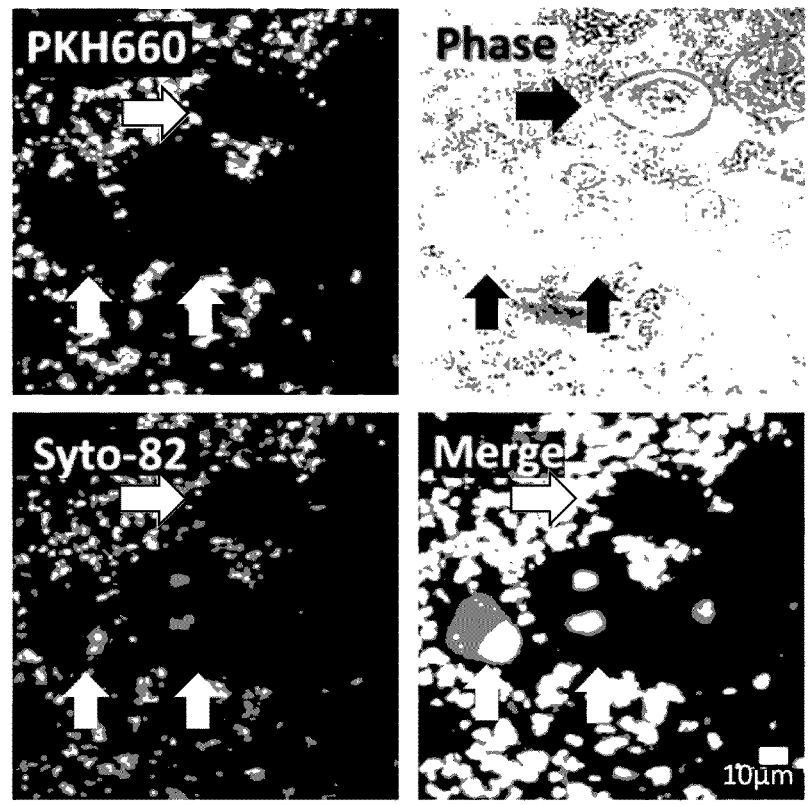
Figure 9:
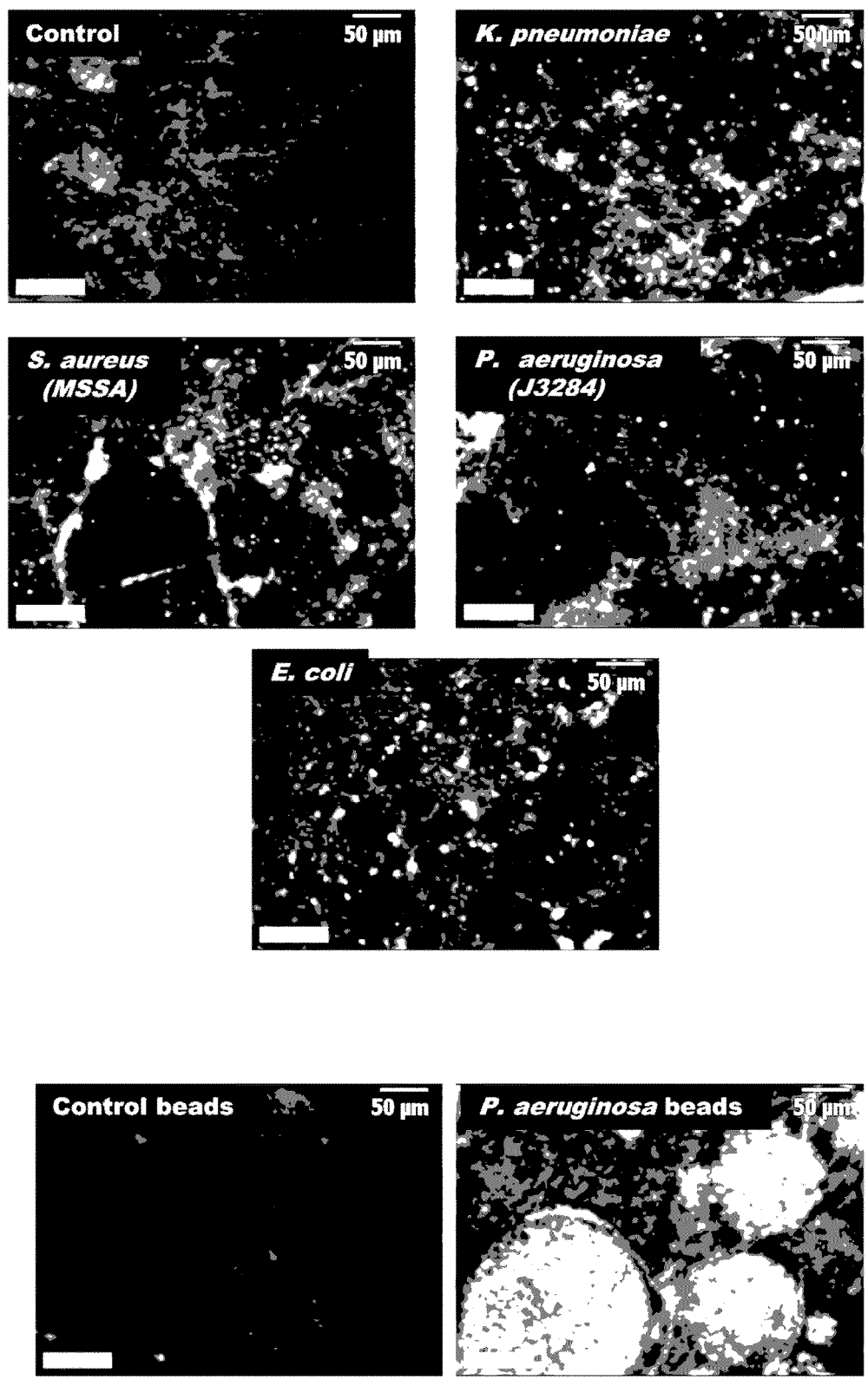

FIG. 9. NBD-UBI$_{dend}$ detects bacteria in situ in the distal ovine lung Representative FCFM images of NBD-UBI$_{dend}$ showing that no punctate signal is seen in control segments whereas the distinctive punctate signal described in FIG. 8 above is seen above background fluorescence in segments instilled with bacteria. Furthermore, agarose beads alone show no fluorescence (control beads) but when beads are coated with bacteria a signal is seen when labelled in situ in the ovine lung, Representative images shown, n≥3 for all experiments.

Figure 10:
Figure 10:
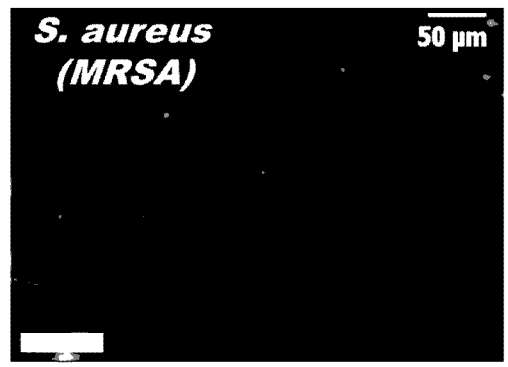
Figure 10:
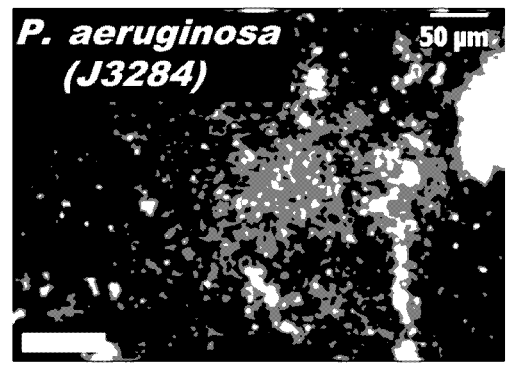
Figure 10:
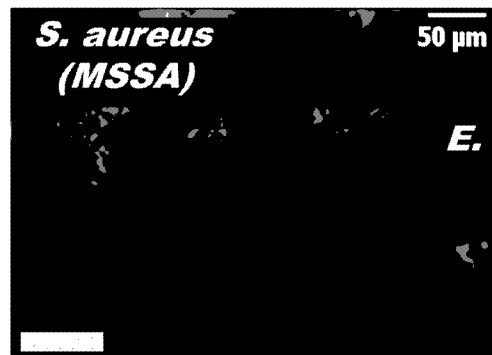
Figure 10:
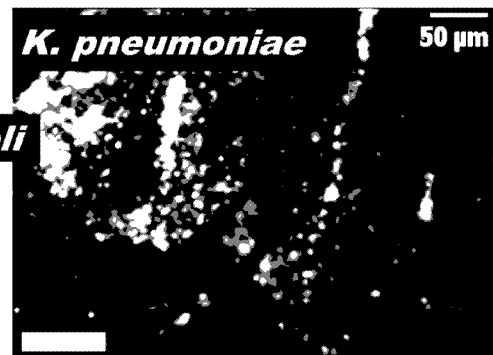
Figure 10:
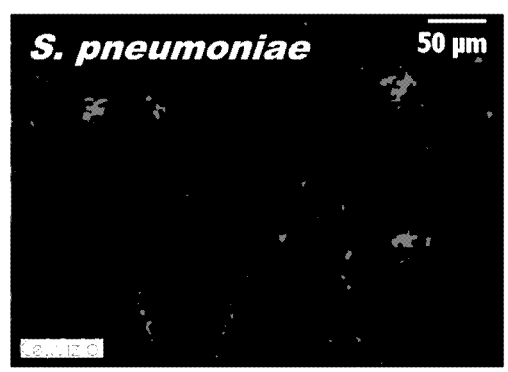
Figure 10:
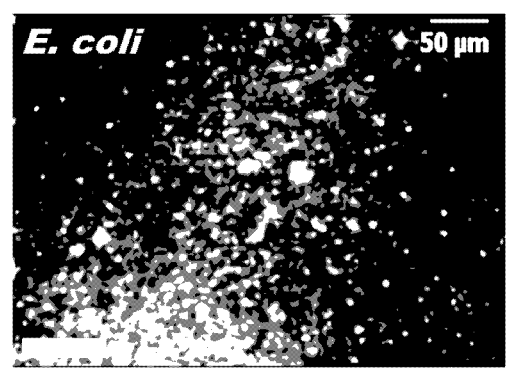
Figure 10:
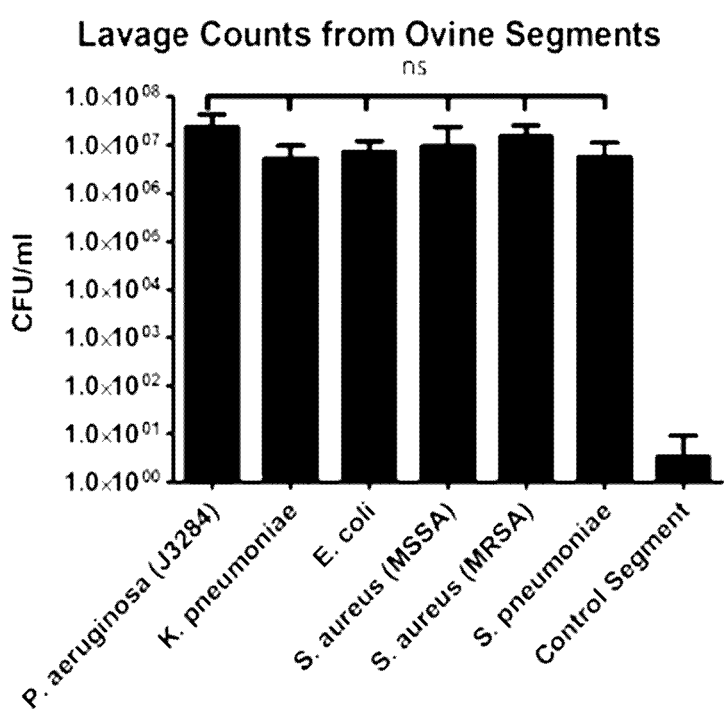
Figure 10:
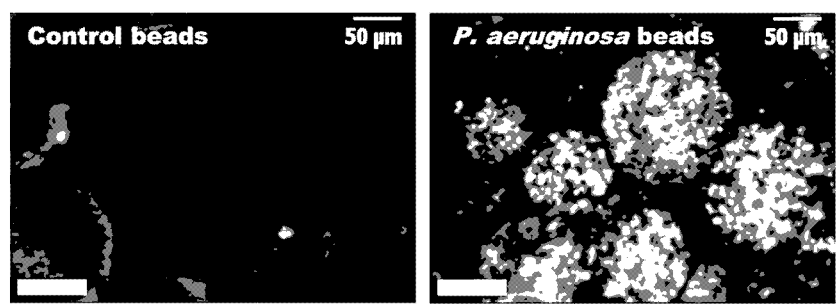

FIG. 10; NB D-PMX selectively labels Gram-negative bacteria in situ in the ovine lung. A) Control segments and Gram-positive segments show no punctate signal, whereas Gram-negative instilled segments show signal identical to positive control. B) Lavage counts from segments demonstrating no significant difference in counts between segments confirming the presence of bacteria. C) Agarose beads alone show no fluorescence but when beads are coated with bacteria a signal is seen when labelled in situ in the ovine lung. Representative images shown, n≥3 for all experiments.

Figure 11:
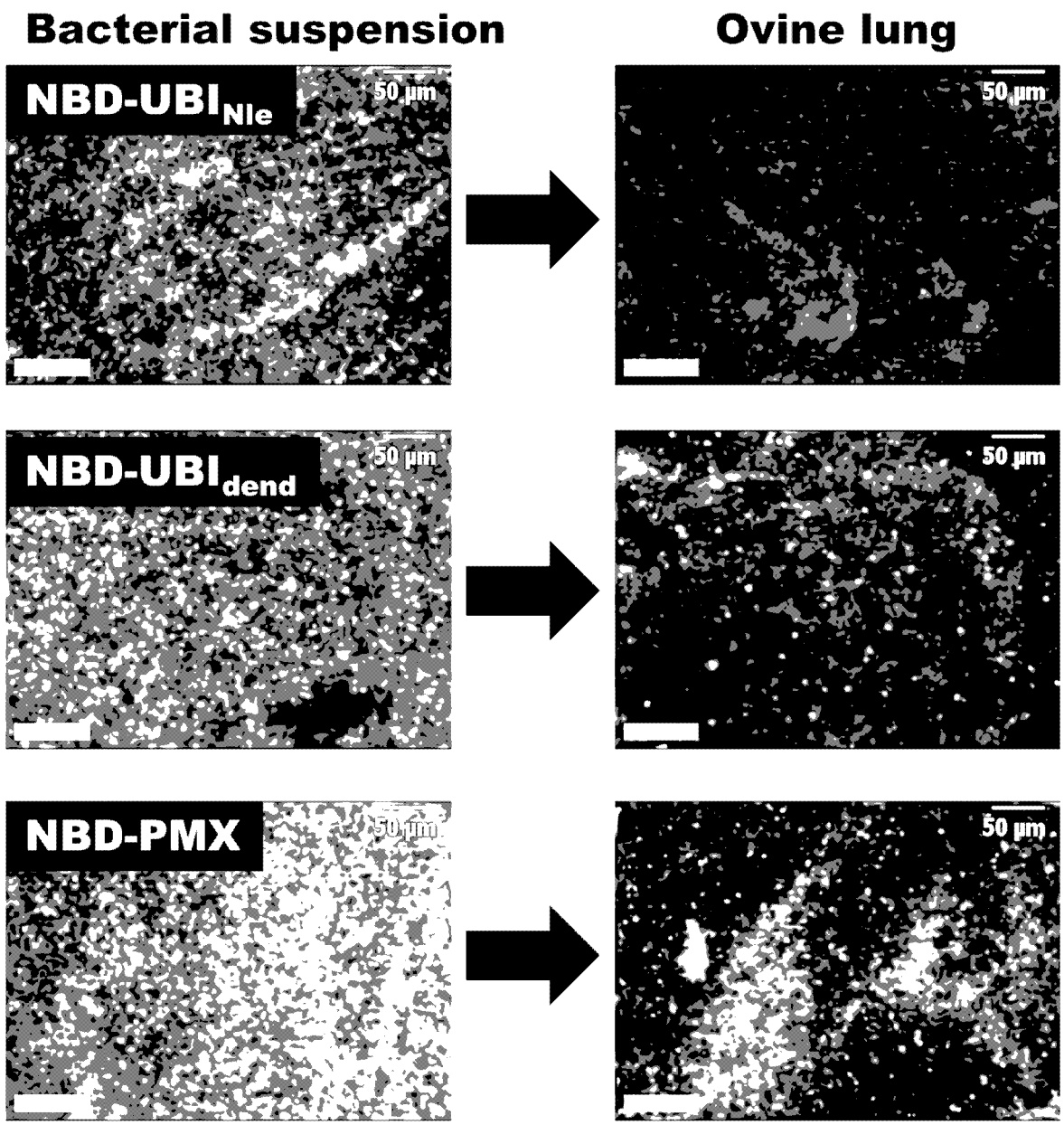

FIG. 11: NBD-UBI$_{dend}$ and NBD-PMX are resistant to 'wash off' allowing detection of bacteria in the ovine lung. Bacteria pre-labelled with either NBD-UBI$_{dend}$ or NBD-PMX were readily visualised by FCFM when instilled into the ovine lung. However, when bacteria pre-labelled with linear NBD-UBI$_{Nle}$ are instilled, no punctate signal is seen, Labelling was confirmed by imaging bacterial suspensions (left hand panels) before instillation into the lung and imaging by FCFM (right hand panels). Note the lower signal-to-noise ratio for NBD-UBI$_{Nle}$ labelled bacteria in suspension. Representative images shown, n=3 for each experiment.

Figure 12:
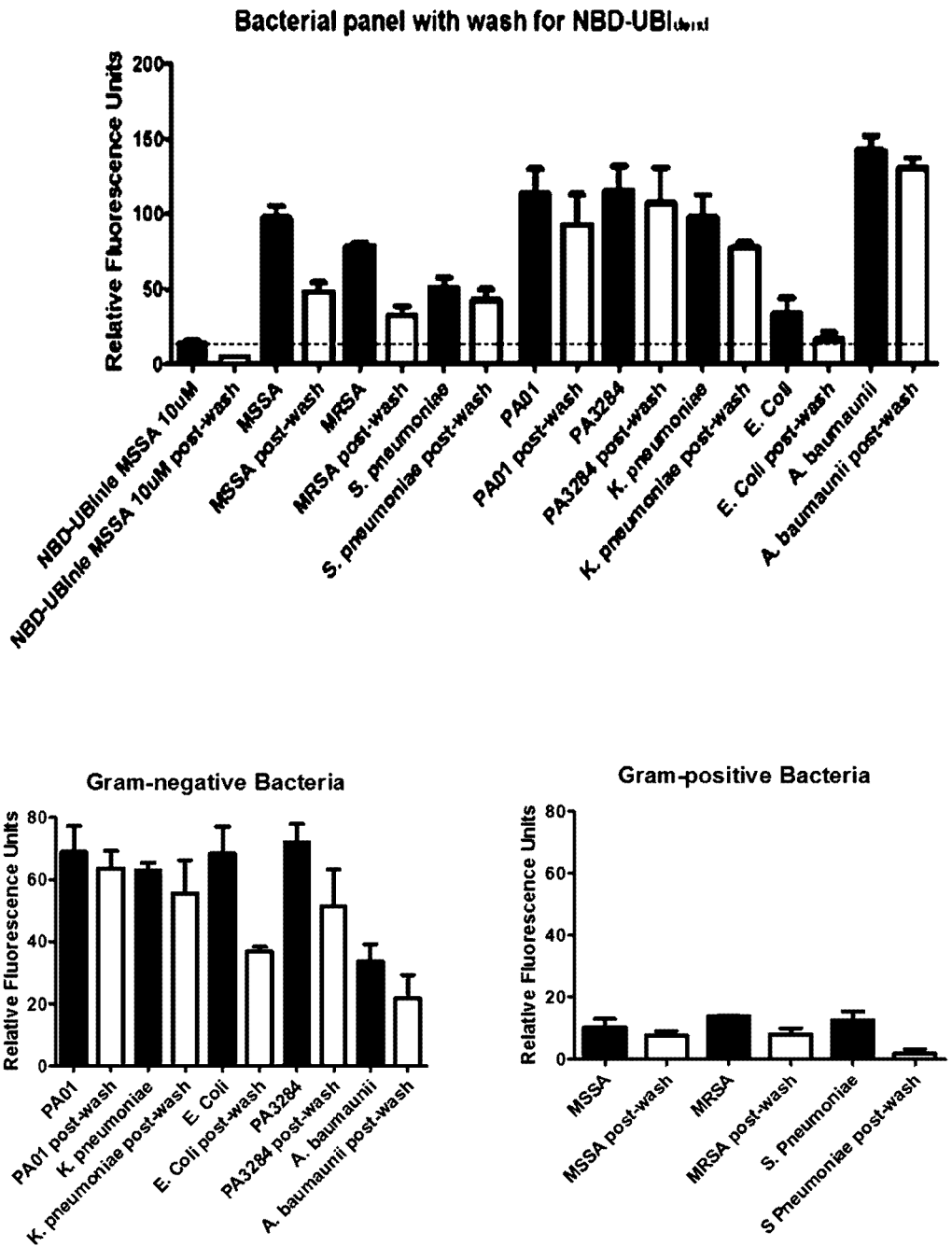

FIG. 12: NBD-UBI$_{dend}$ retains fluorescence when wash performed. A) The bacterial panel was imaged by laser scanning confocal microscopy in the continued presence of NBD-UBI$_{dend}$ (black) and following PBS wash (white). Quantification demonstrates fluorescence retention above linear NBD-UBI with MSSA in the continued presence of probe (dotted line). n≥3, with three random field-of-views assessed for each experiment. B) Bacterial panel imaged with NBD-PMX in the continued presence of probe (black) or following PBS wash (white) demonstrating higher fluorescence retention of all Gram-negative bacteria above NBD-PMX with Gram-positives in the continued presence of probe. n≥3, with three random field-of-views assessed for each experiment.

Figure 13:
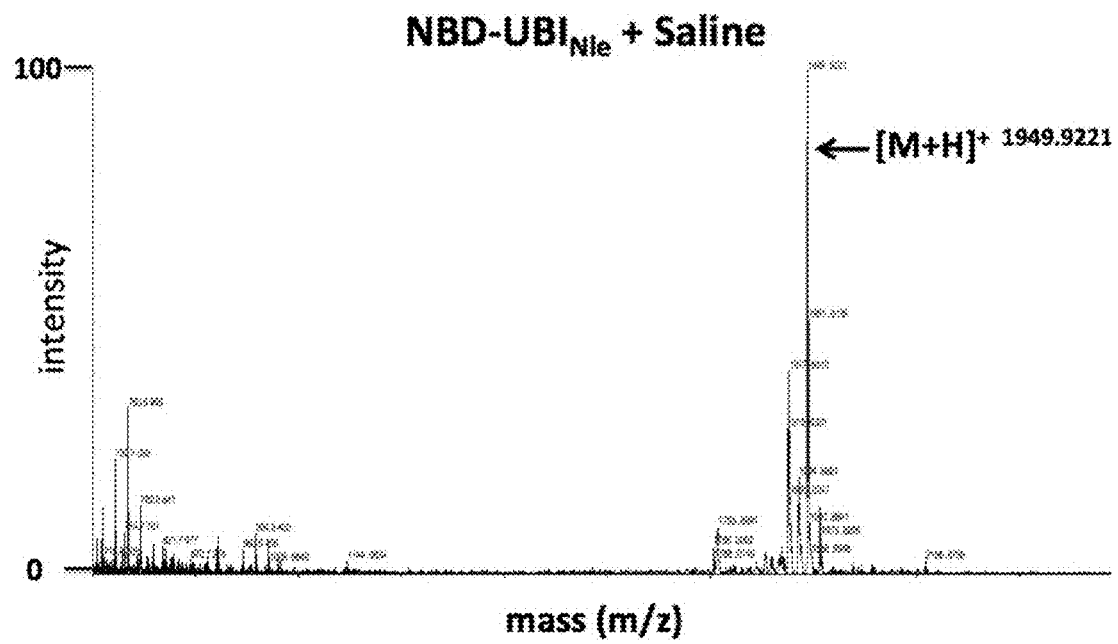
Figure 13:
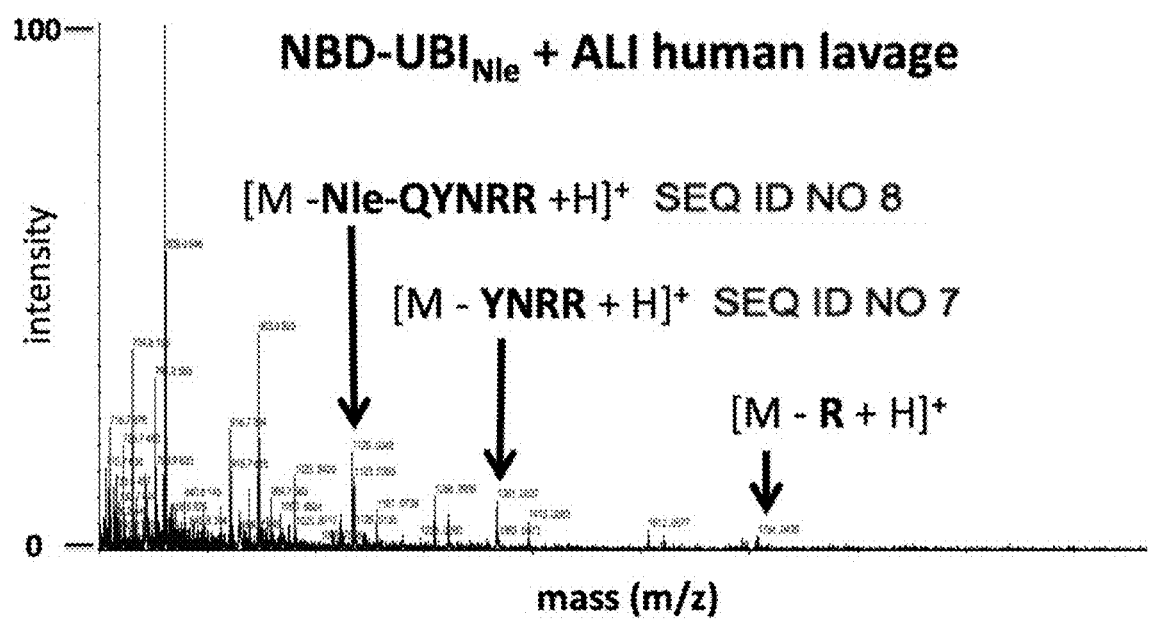
Figure 13:
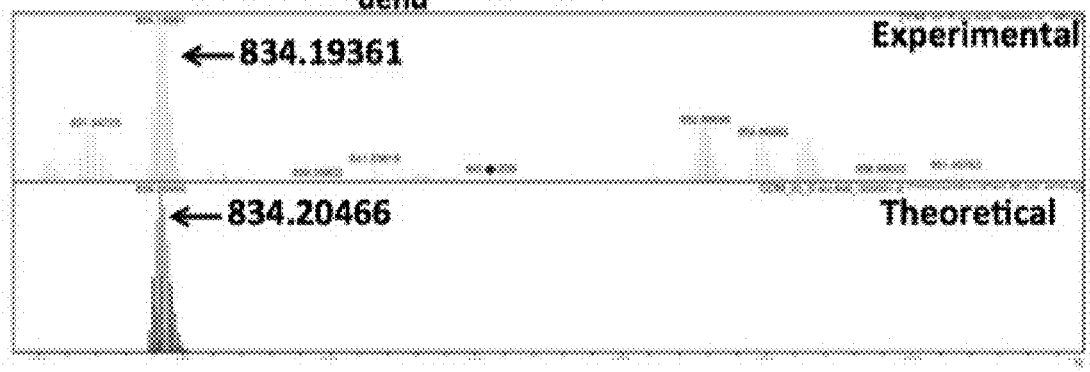
Figure 13:
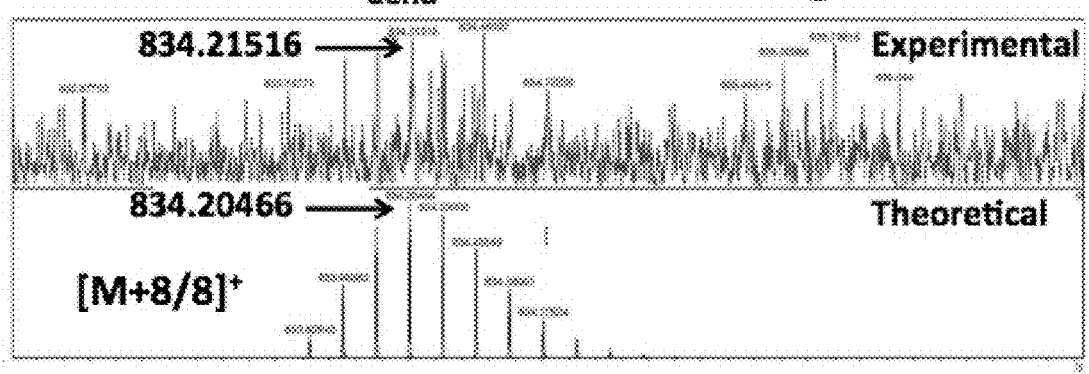
Figure 13:
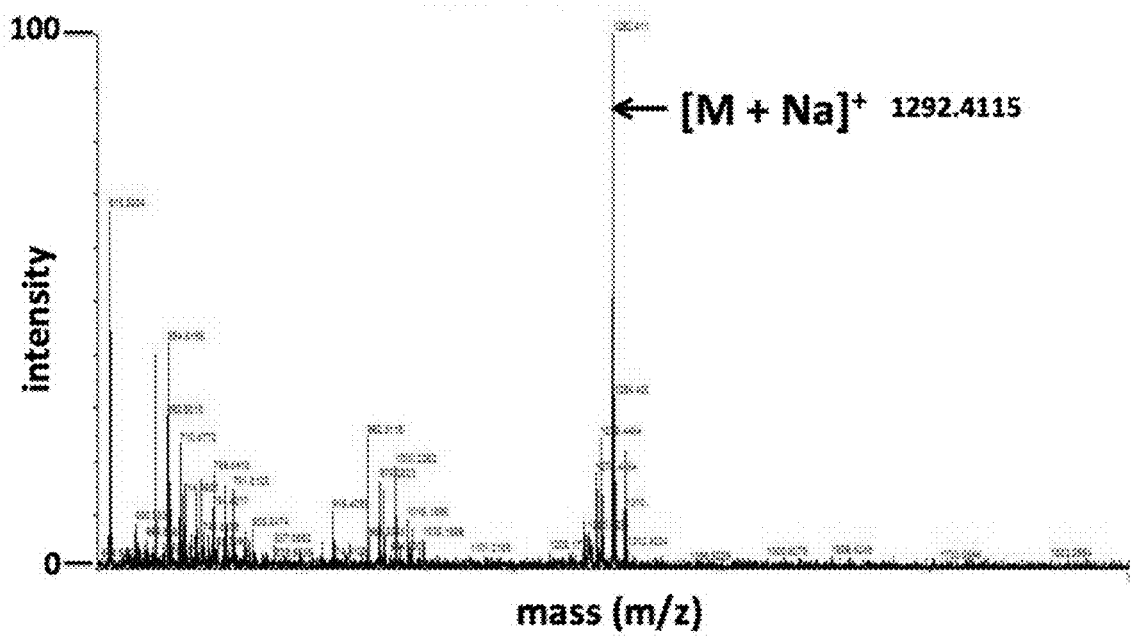
Figure 13:
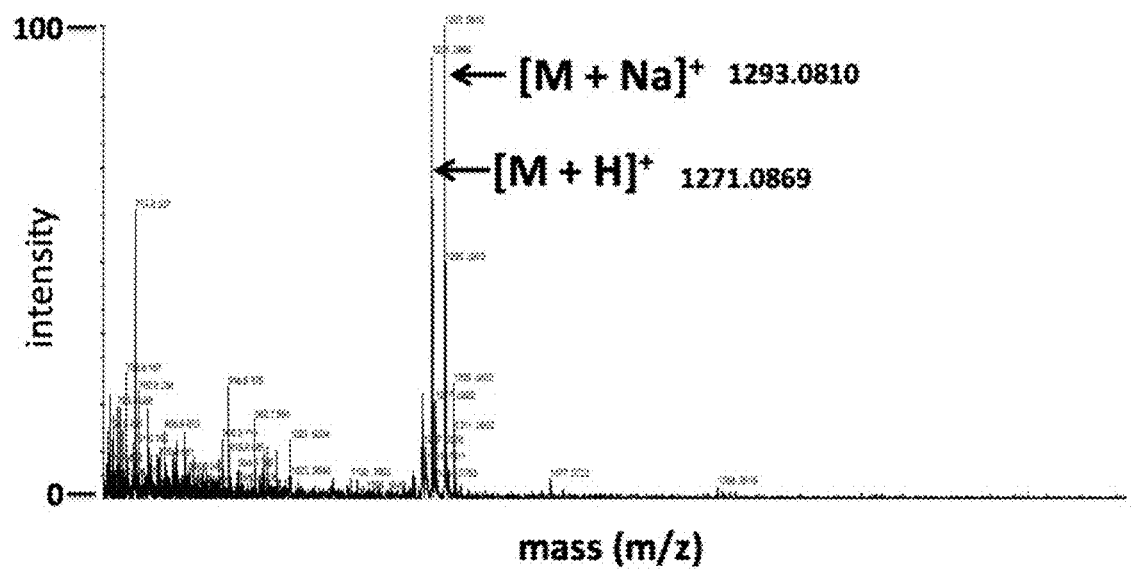

FIG. 13: NBD-UBI$_{dend}$ is stable in Acute Lung Injury Broncholalveolar Lavage Fluid (ALI HALF). Matrix-Assisted Laser Desorption/Ionization Time-of-Flight Mass Spectrometry (MALDI-TOF MS) analysis demonstrated stability of NBD-UBI$_{Nle}$, wherein UBI$_{Nle}$ is SEQ ID NO 3, in the presence of saline (arrow indicates correct peak seen at mass of 1949) but degradation in the presence of ALI lavage (no peak seen at mass 1949 but arrows show predictable degradation compounds, SEQ ID NO 7 and SEQ ID NO 8) when co-incubated for 30 minutes. By contrast NBD-UBI$_{dend}$ remains stable when assessed by Fourier Transform Mass Spectrometry (FTMS) (data shown represents a theoretical plot and an experimental plot demonstrating the peaks correspond indicating presence of compound). NBD-PMX is stable in ALI BALE MALDI-TOF analysis demonstrated stability of NBD-PMX in the presence of saline or ALI lavage (arrows indicates correct peaks seen at mass of 1291-1293) when co-incubated for 30 minutes.

Figure 14:
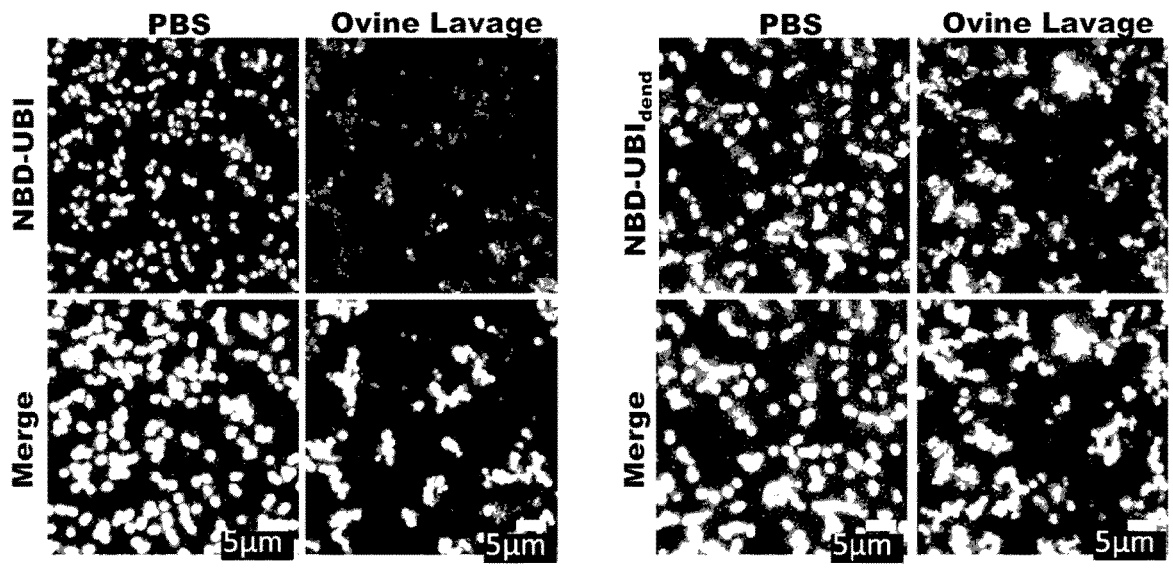
Figure 14:
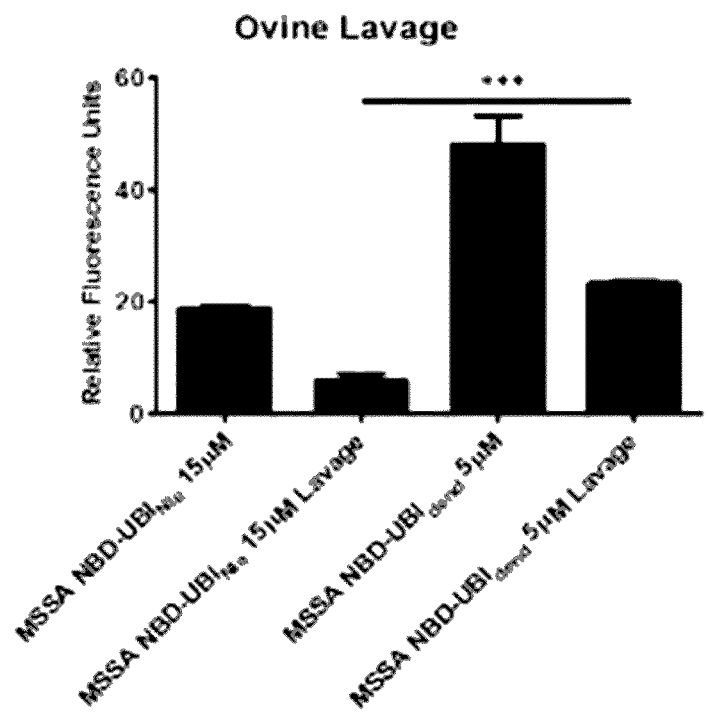
Figure 14:
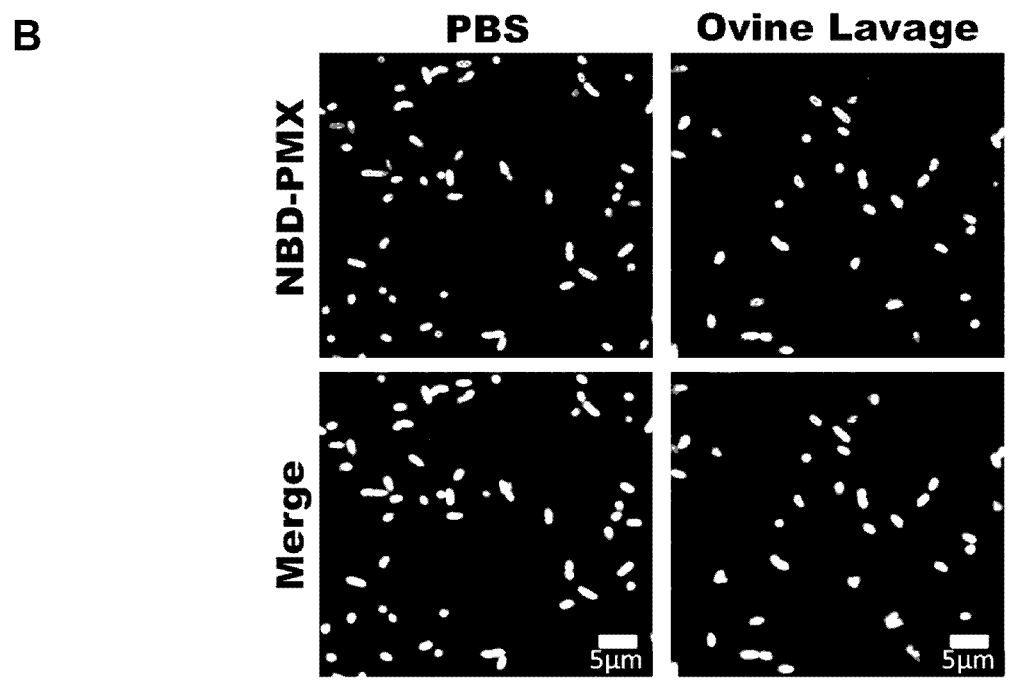
Figure 14:
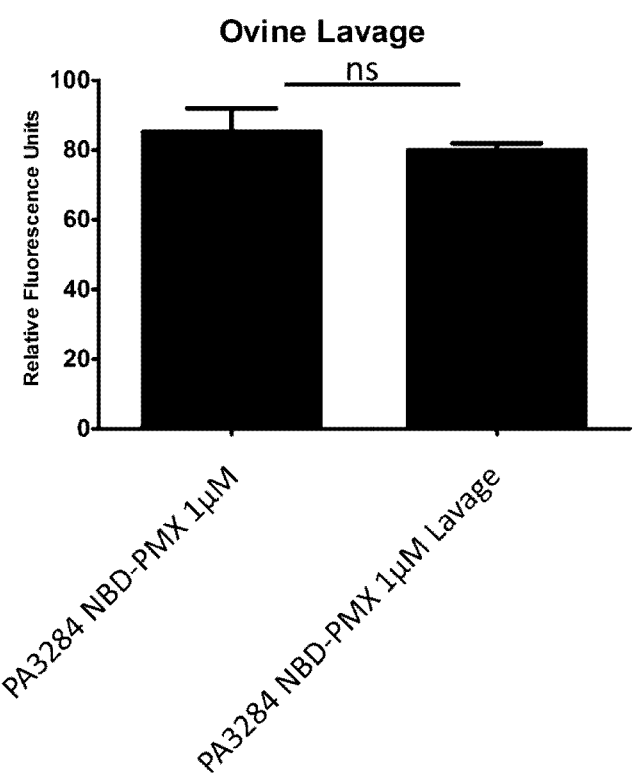

FIG. 14 NBD-UBI$_{dend}$ retains higher fluorescence on bacteria in ovine lavage than equimolar equivalent of linear. A) MSSA imaged by laser scanning confocal microscopy in the presence or absence of ovine lavage with NBD-UBI$_{Nle}$ (15 μM) and NBD-UBI$_{dend}$ (5 μM). Both NBD-UBI compounds have reduced fluorescence in ovine lavage but NBD-UBI$_{dend}$ retains higher fluorescence intensity. B) In contrast, PA3284 imaged in the presence or absence of ovine lavage with NBD-PMX (1 μM) demonstrates no significant reduction of fluorescence intensity. Representative images shown, n=3.

Figure 15:
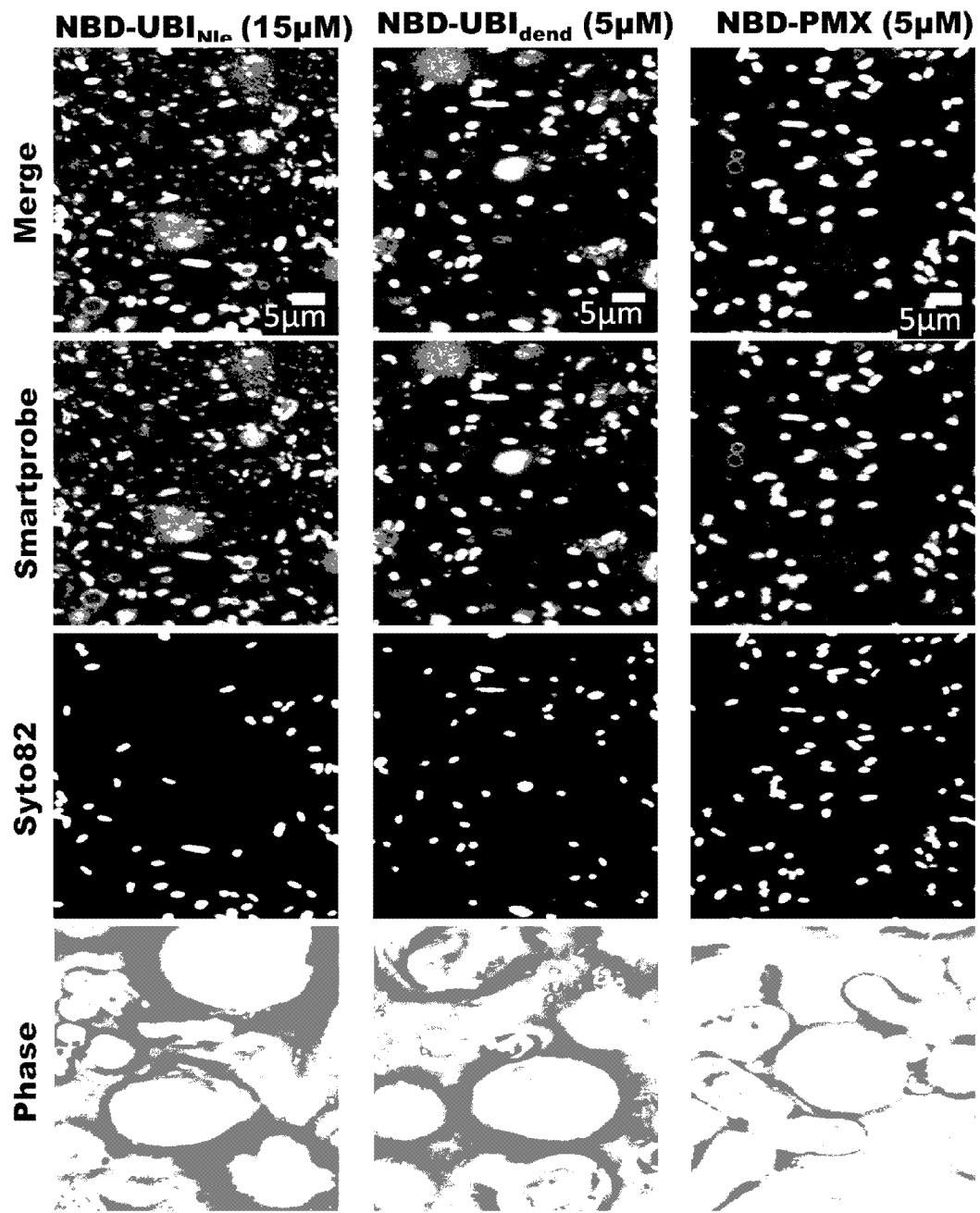
Figure 15:
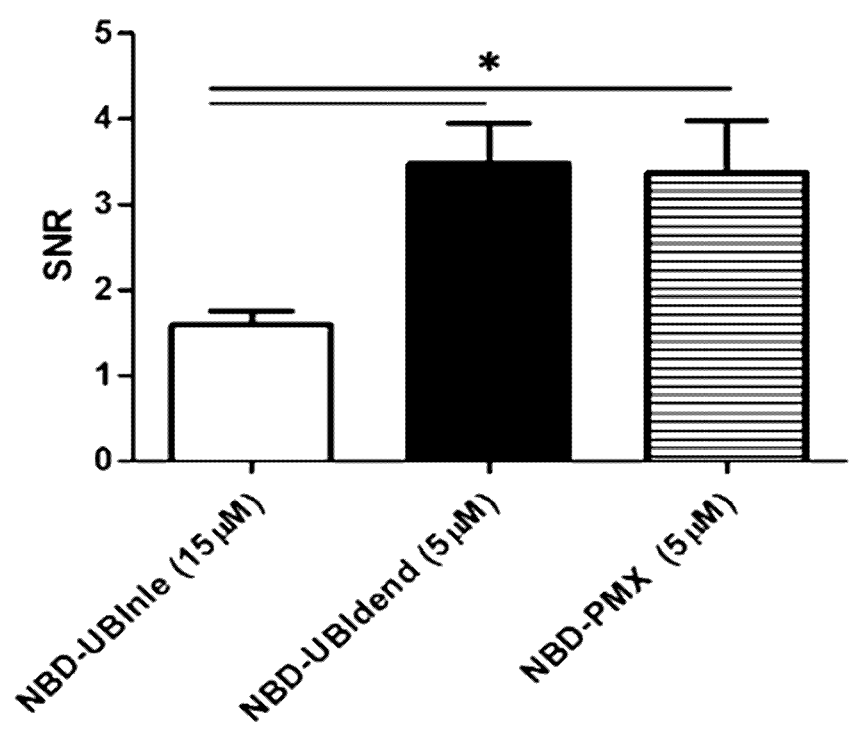

FIG. 15: NBD-UBI$_{dend}$ and NBD-PMX successfully image bacteria in a surfactant-rich environment. Ratio of bacterial fluorescence intensity:surfactant fluorescent intensity quantified from confocal microscopy images. For equimolar NBD concentrations NBD-UBI$_{dend}$ and NBD-PMX have significantly higher bacterial: surfactant intensity than NBD-UBI$_{Nle}$.

FIG. 16A: Elastase dependent bacterial labelling scheme. The fluorophore on the bacterial binding component is quenched by a dark quencher meaning that no fluorescence is seen upon binding to bacteria. Cleavage of the elastase specific sequence AAPV (SEQ ID NO: 9) liberates the bacterial binding component (PV-NBD-UBI) from the dark quencher methyl red (MR).

FIG. 16B: Elastase dependant bacterial labelling in vitro. MSSA, counterstained with FM-464 (left-hand image red), co-incubated with isolated human neutrophils demonstrating bacterial labelling in the presence of neutrophils (middle image), which is inhibited in the presence of an elastase inhibitor.

Figure 17A:
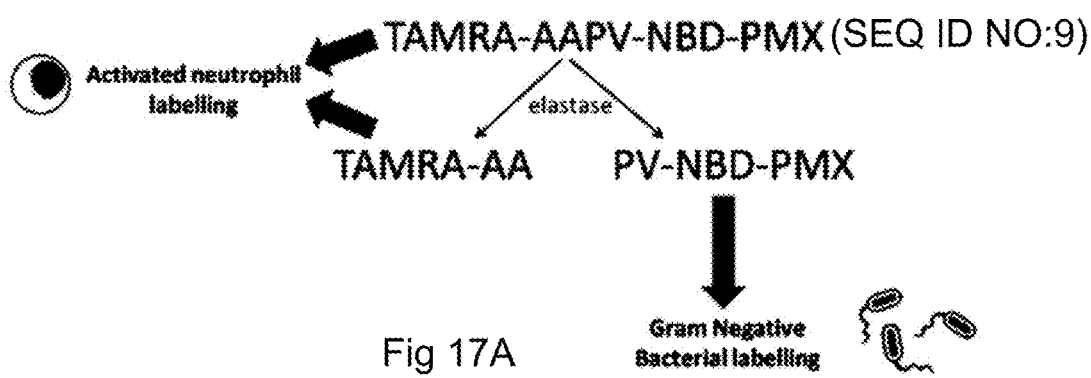

FIG. 17A: Elastase dependent bacterial labelling scheme. The fluorophore on the bacterial binding component is quenched by a different fluorophore of a longer wavelength meaning that no fluorescence is seen upon binding to bacteria. Cleavage of the elastase specific sequence AAPV (SEQ ID NO: 9) liberates the bacterial binding component (PV-NBD-UBI) from the quencher (TAMRA). TAMRA reports the presence of activated neutrophils by endocytic uptake.

Figure 17B:
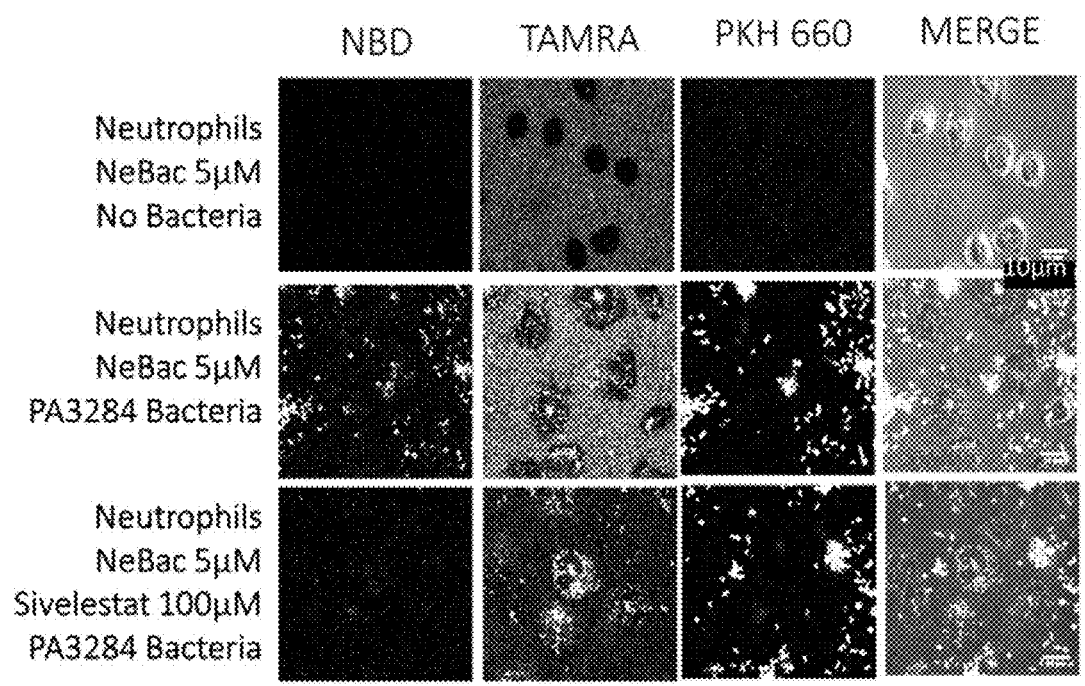

FIG. 17B Elastase dependent bacterial labelling in vitro. *Pseudomonas aeruiginosa* (PA) counterstained with PKH 660 (third images from left) was incubated with TAMRA-AAPV-NBD-PMX (SEQ ID NO: 9) and demonstrated no labelling in the presence of unactivated neutrophils (top panel), bacterial labelling in an elastase dependent manner and labelling of activated neutrophils in an elastase independent manner.

Figure 17C:
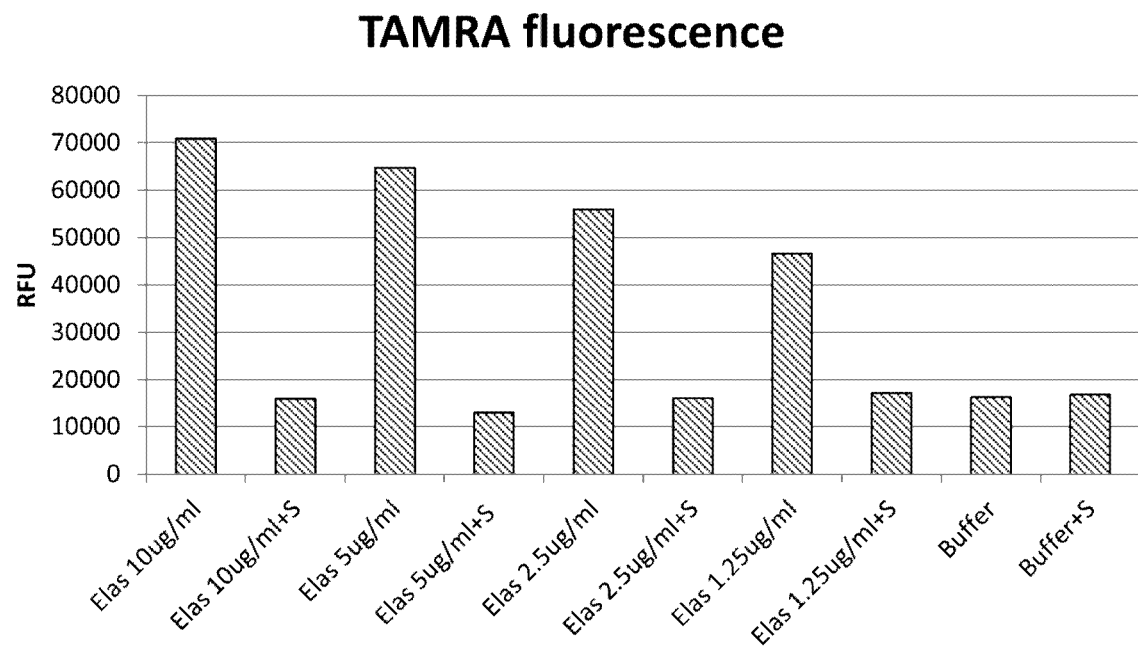

FIG. 17C: Elastase dependent fluorescence increase of TAMRA following cleavage. Spectrophotometer data to demonstrate the unexpected observation of an increase in fluorescence of TAMRA-AA (cleaved compound) compared to TAMRA-AAPV-NBD-PMX (SEQ ID NO: 9) in an elastase dependent manner, and inhibited with an elastase inhibitor (ex 525 nm, Em 580 nm), FIG. 18: Image Processing Algorithms delineate 'positive' and 'negative' frames from FCFM data (A) raw data for a frame that is deemed positive or negative. (B) Without pre-processing, spot-detection is ineffective. Following estimation of background noise (C), high-pass filtering (D) and appropriate thresholding (E), the current algorithm detect minimal punctate signal in negative frames (F).

Figure 19:
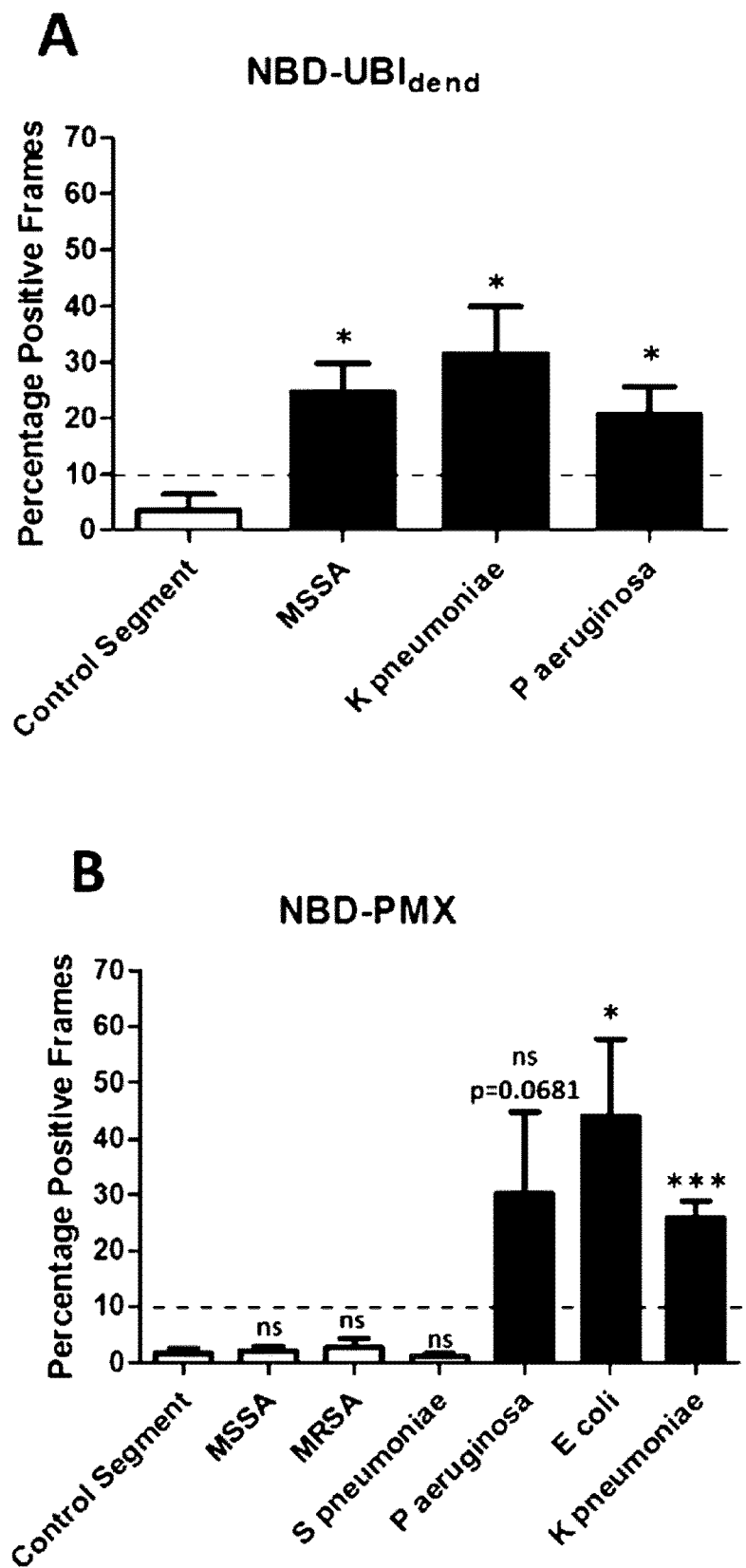

FIG. 19: Automated Image Processing of entire FCFM videos (up to 3500 frames) demonstrates detection of bacteria. A) Analysis of NBD-UBI$_{dend}$ videos with thresholding at 80 spots per frame and an arbitrary cut-off of 10% enables objective detection of bacteria using a combination of Laplacian of Gaussian (LoG) and Difference of Gaussians (DoG) positive frames. B) Analysis of NBD-PMX videos with thresholding at 80 spots per frame and an arbitrary cut-off of 10% enables objective detection of) Gram status using a combination of LoG and Do G positive frames. n=4 for all analyses, except S. pneumoniae where n=3, Statistical analysis when compared to control.

Figure 20:
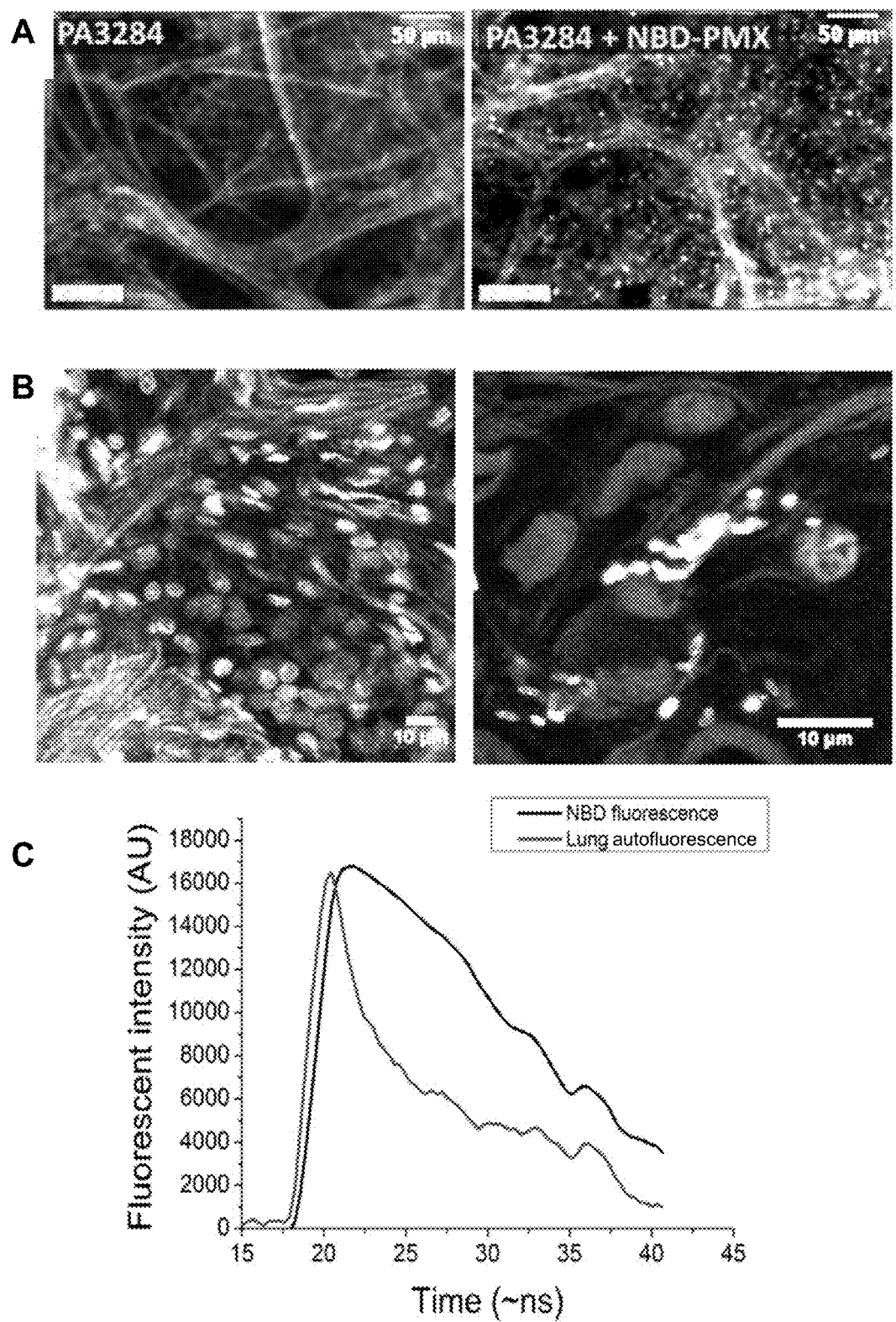

FIG. 20: Bacteria detected in the presence of human lung tissue autofluorescence. A) FCFM images of human lung tissue with PA3284 demonstrating elastin autofluorescence and no bacterial signal (left) and human lung tissue with PA3284 co-incubated with NBD-PMX (right) demonstrating bacterial signal. B) Live confocal microscopy images (merge) showing merge images of nucleic acid counterstain with no NBD-PMX labelling, Bacteria in right panel can be clearly seen, labelled with NBD PMX and above the background fluorescence. C) The fluorescent lifetime of NBD is significantly longer than that of the autofluorescence of the indigenous cells of the lung, measured by laser excitation at 488 nm and time resolved single photon counting spectrometer, and this can be used to identify the probes in vivo and increase signal-to-noise of sensing and imaging.

Figure 21:
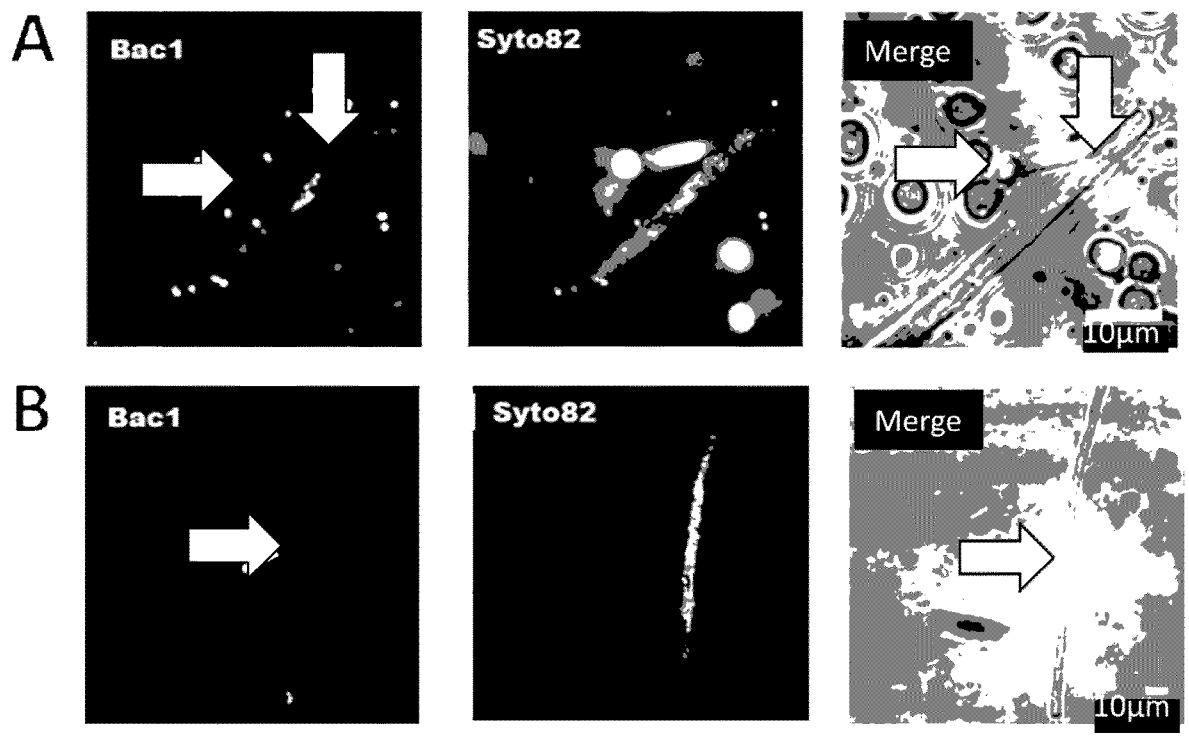

FIG. 21: NBD-UBI$_{dend}$ labels bacteria and variably labels A. fumigatus but not C. albicans imaged by confocal microscopy. Representative images of NBD-UBI$_{dend}$ 5 µM demonstrating A: labeling of bacteria (P aeruginosa) and fungal hyphae of A. fumigatus (white arrow) but not C. albicans (white arrow). Panel B demonstrates the variability of labeling on fungal hyphae.

Figure 22:
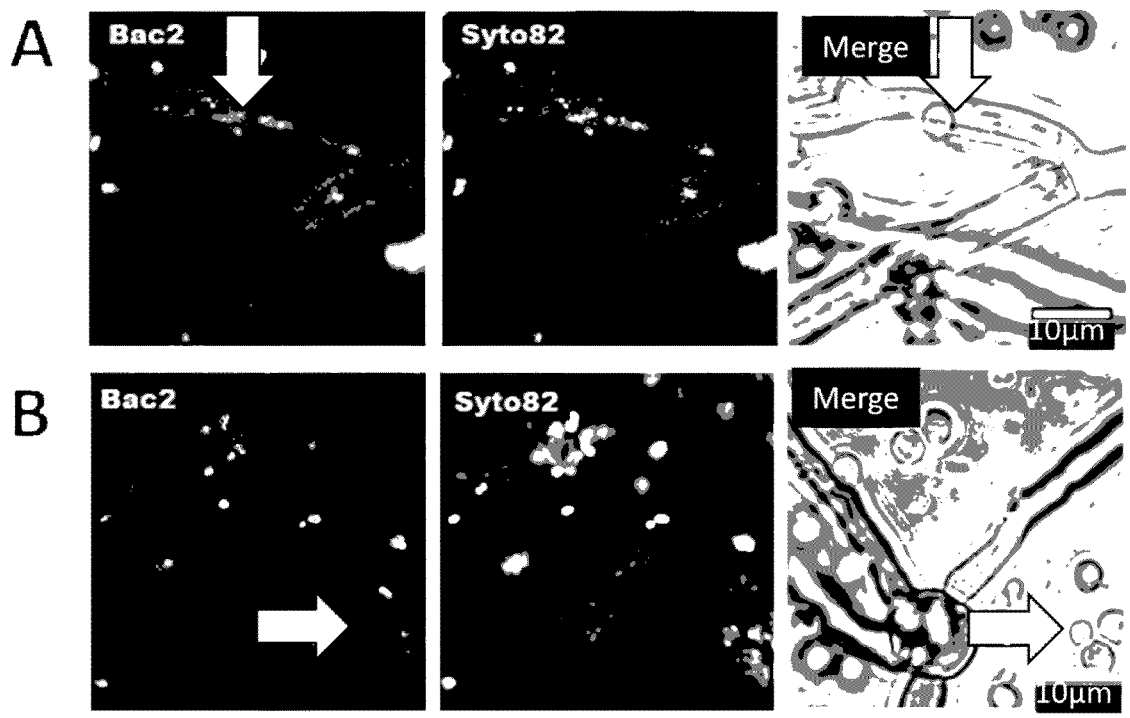

FIG. 22: NBD-PMX labels bacteria and variably labels A. fumigatus but not C. albicans imaged by confocal microscopy. Representative images of NBD-PMX 5 µM demonstrating A: labeling of bacteria (P aeruginosa) and fungal hyphae of A. fumigatus (white arrow) but not C. albicans (white arrow). Panel B demonstrates the variability of labeling on fungal hyphae. Data shown for 5 uM but similar results seen for 1 uM.

Figure 23:
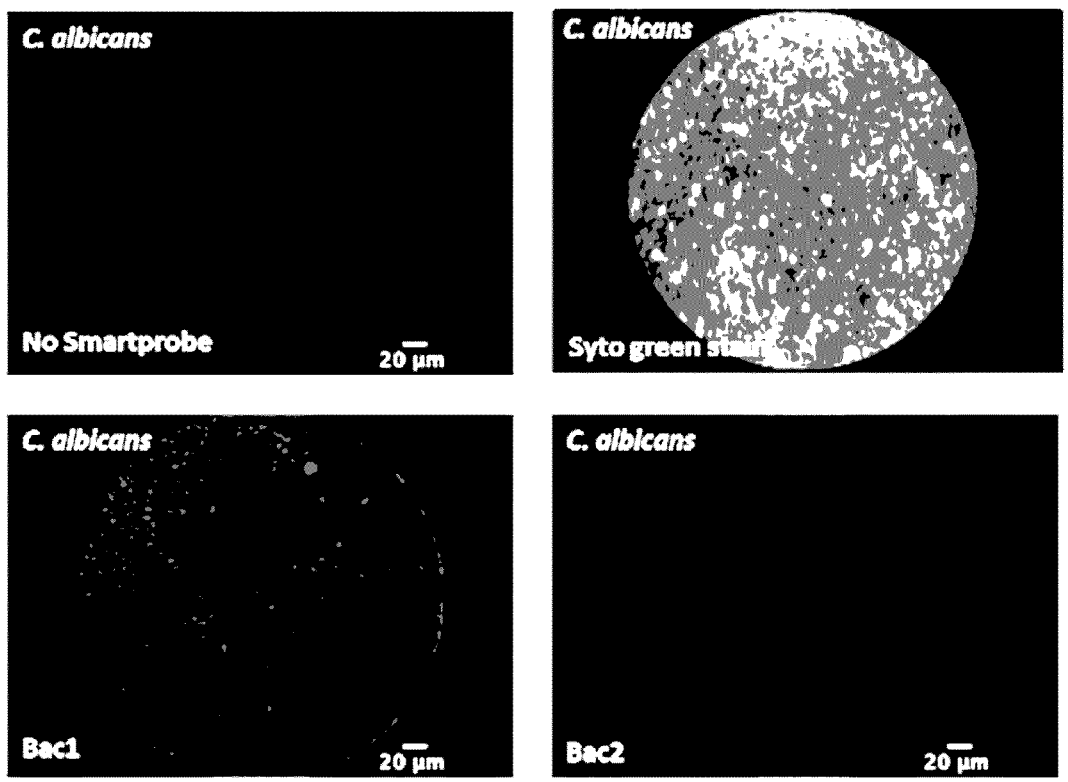

FIG. 23. Suspensions of C. albicans do not demonstrate increased fluorescence when imaged with FCFM. Figure shows positive control of C. albicans labeled with Syto green and imaged in suspension but no labeling without the probe, with NBD-UBIdend or NBD-PMX with FCFM.

Figure 24:
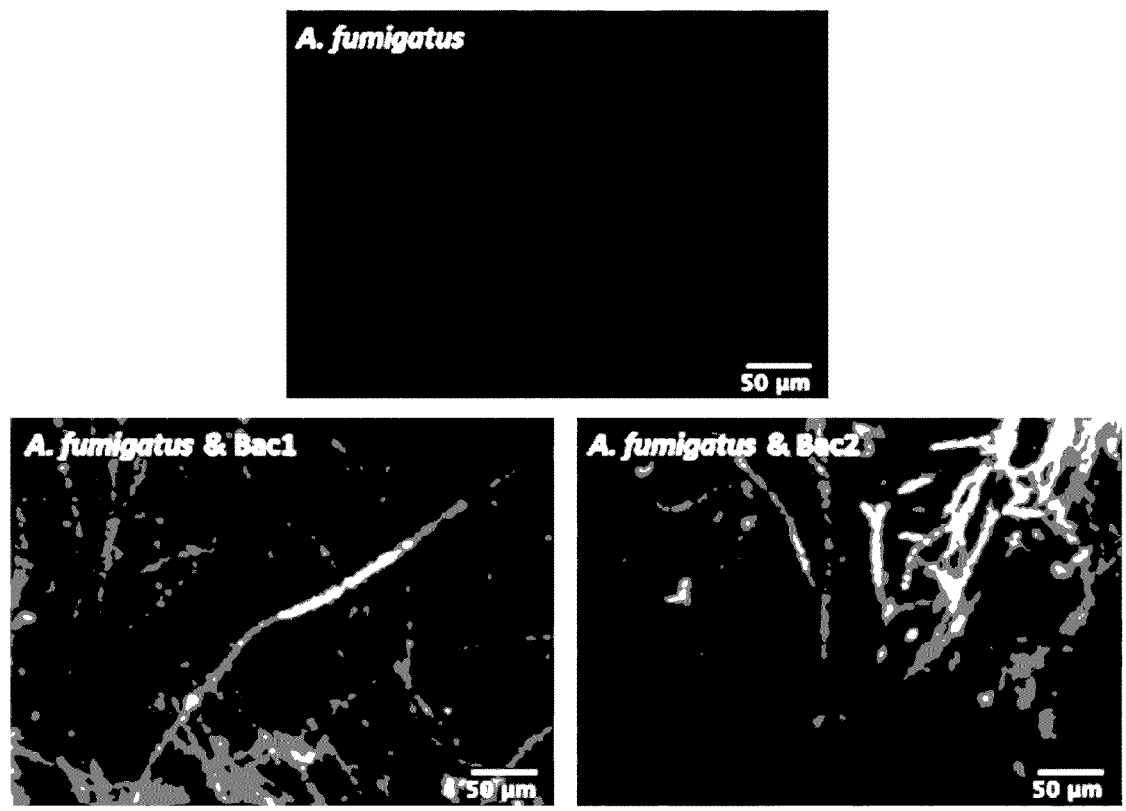

FIG. 24: A. fumigatus demonstrates fluorescence in a distinctive and characteristic manner when imaged with FCFM. Top panel is without the probe demonstrating no intrinsic autofluorescence and bottom panels show distinct pattern with NBD-UBI$_{dend}$ and NBD-PMX.

Figure 25:
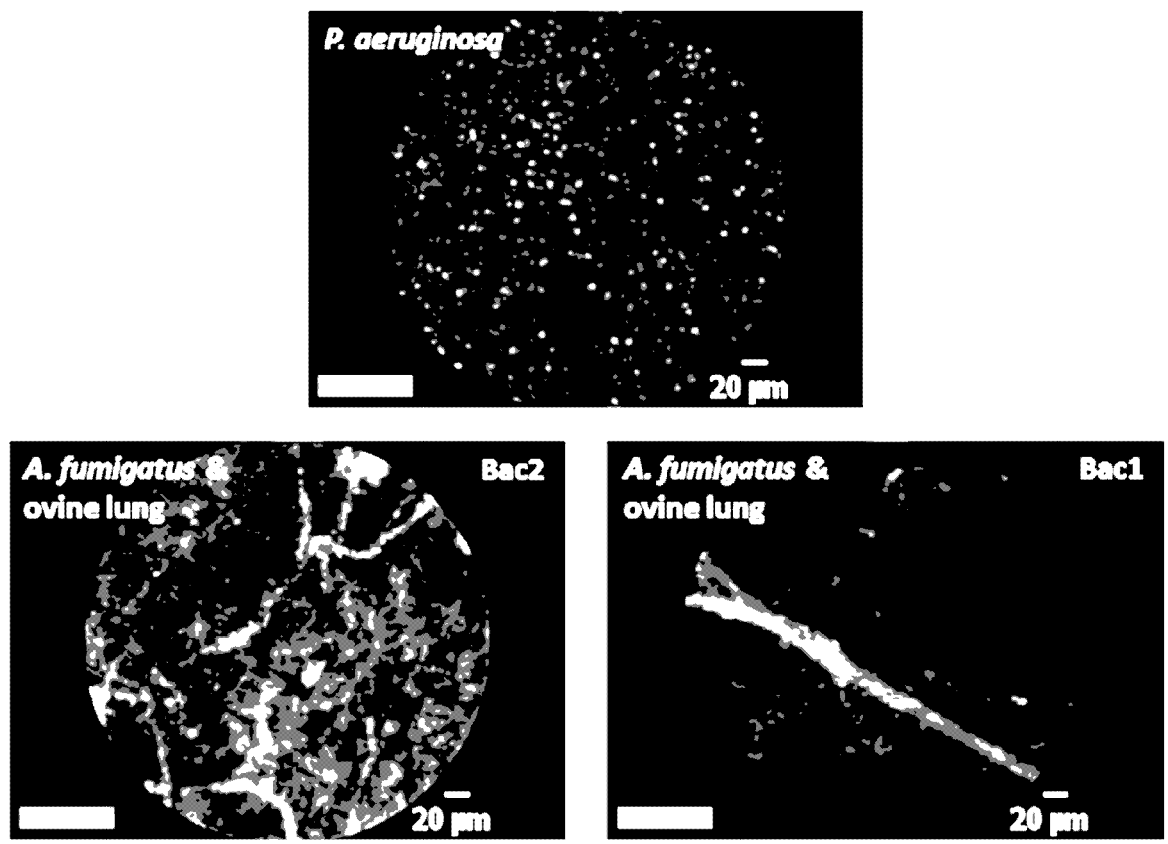

FIG. 25: A. fumigatus demonstrates linear pattern of fluorescence in the presence of ovine lung tissue, which is distinct from a bacterial signal. Top panel shows the pattern of fluorescence with a bacterial solution with the probe and bottom panels show A. fumigatus filaments with NBD-UBI$_{dend}$ and NBD-PMX on ovine lung.

Figure 26:
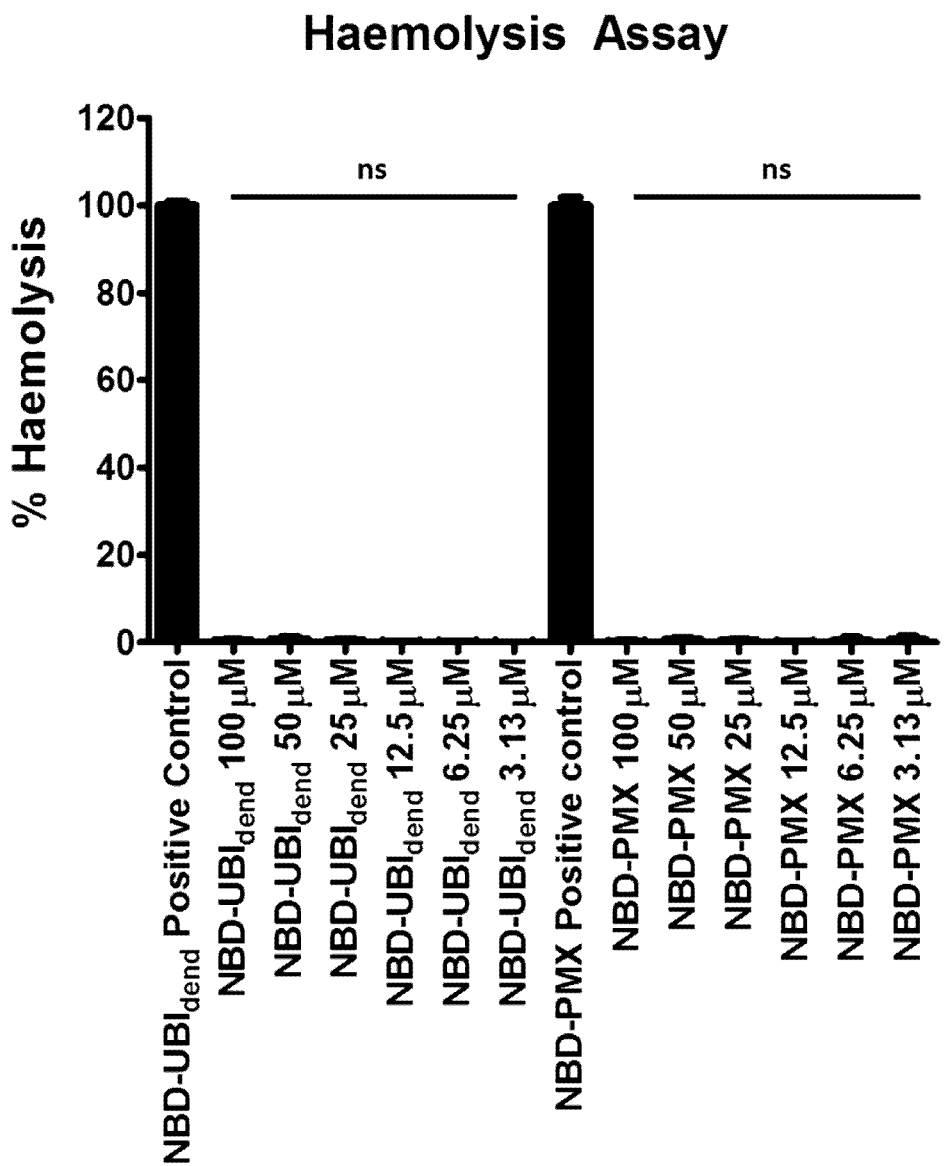

FIG. 26: No haemolysis seen with NBD-UBI$_{dend}$ or NED-PMX up to 100 µM. Haemolysis assay (n=3) demonstrating no haemolysis on concentrations up to 100 µM, Positive control was 0.2% Triton-X and values corrected to represent 100% haemolysis for Triton-X.

Figure 27:
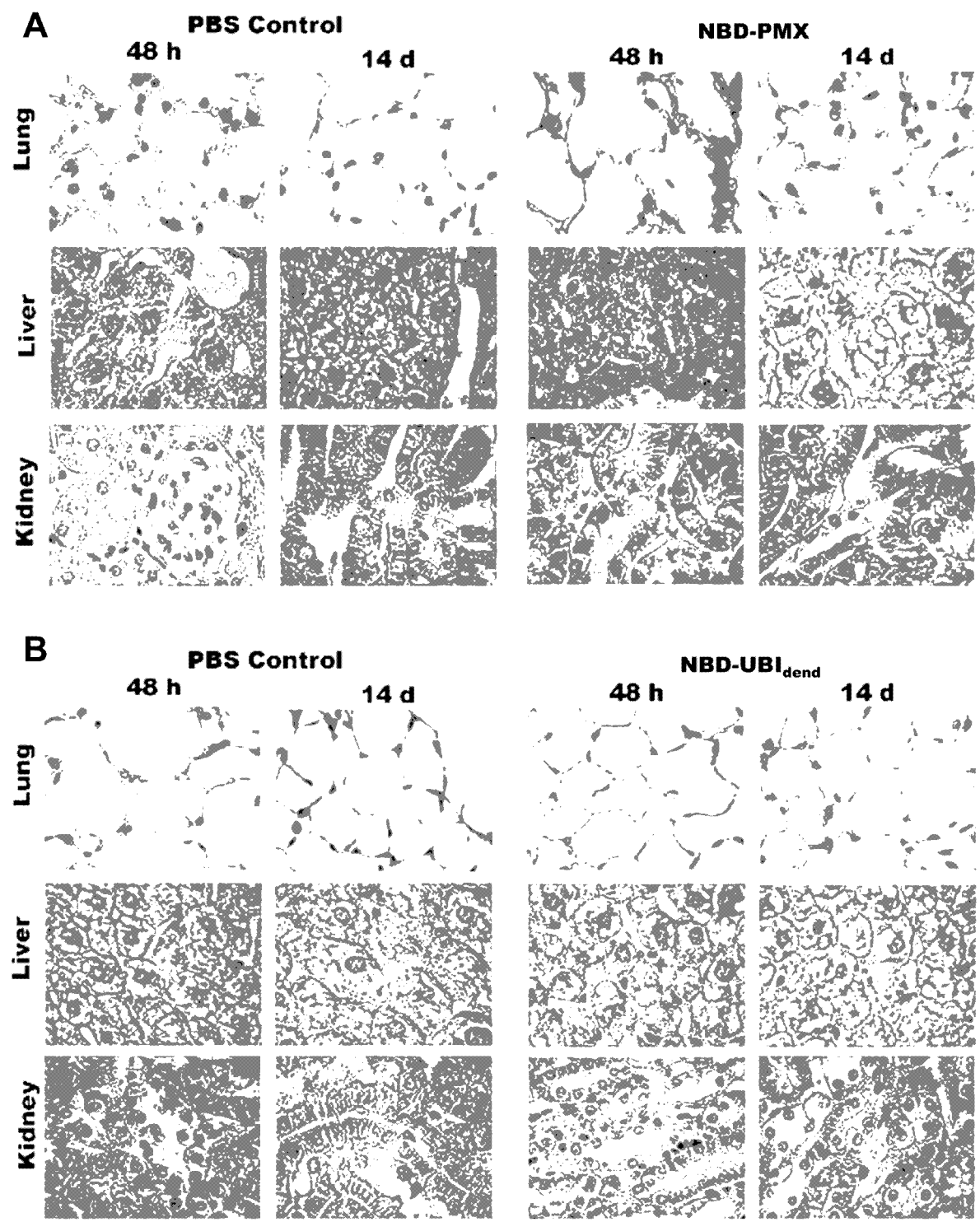

FIG. 27. A: NBD-PMX shows no organ toxicity in a 2 week single instillation model in mice. Representative histology images (×100) for NBD-PMX compared to PBS control animals at 48 hours and 14 days. No differences from control were seen in any group (blindly scored by a consultant histopathologist). B: NBD-UBI$_{dend}$ shows no organ toxicity in a 2 week single instillation model in mice. Representative histology images (×100) for NBD-UBI$_{dend}$ compared to PBS control animals at 48 hours and 14 days. No differences from control were seen in any group (blindly scored by a consultant histopathologist).

Figure 28:
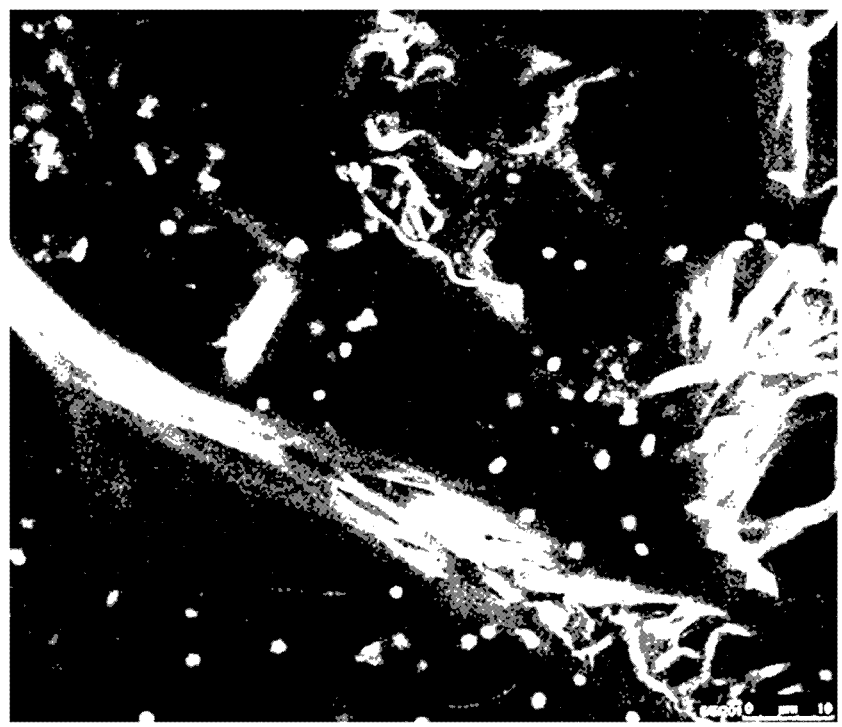
Figure 28:
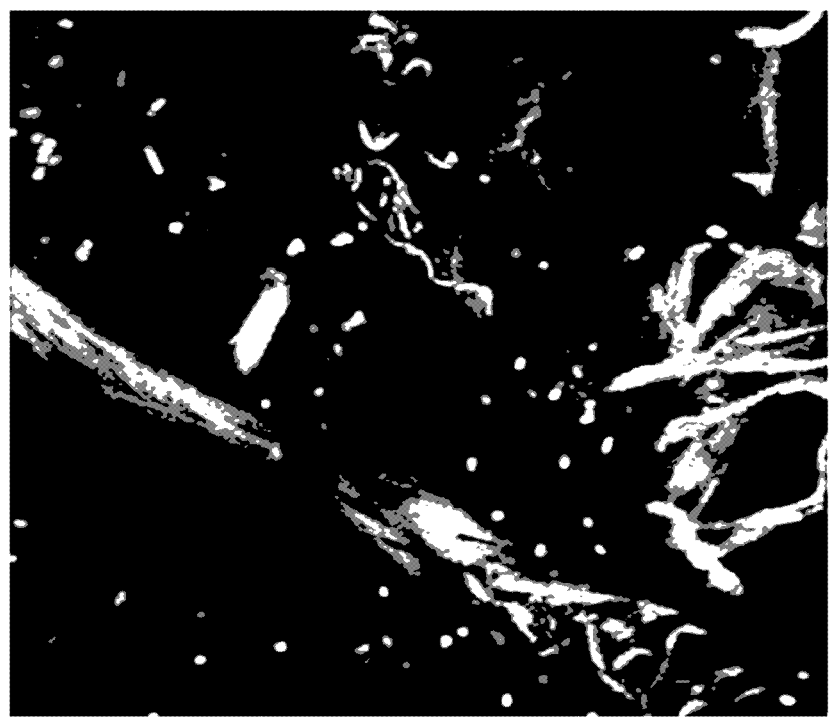

FIG. 28. Fluorescence Life Time imaging easily distinguishes lung tissue from bacteria. Left panel shows confocal at 488 nm excitation of lung and bacteria (dots) in lung tissue. FLIM (right panel) shows dear differences in imaging of lung tissue and bacteria. Imaging performed using NBD-UBI$_{dend}$ and S. aureus on human lung tissue

SPECIFIC DESCRIPTION OF EMBODIMENTS OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In the following description of example embodiments of the invention, binding moieties comprising a polymyxin moiety are given the code "PMX", and binding moieties comprising a ubiquicidin moiety are given the code "UBI". For example, embodiments of the invention that comprise a plurality of probe elements comprising the NBD and the modified ubiquicidin fragment UBI$_{Nle}$ ("Dendron Probes") is referred to as NBD-UBI$_{dend}$.

Choice of Probe Element Fluorophore

Figure 1:
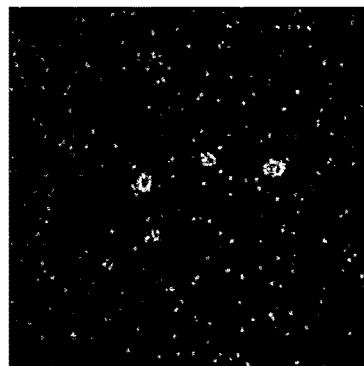
FIG. 1: Fluorophore choice impacts on ability to image labelled bacteria with improved signal to noise for NBD constructs over Fluorescein (FAM). A) Bacteria (Methicillin sensitive Staphylococcus aureus, MSSA), counterstained with FM-464 (shown hi left-hand column), and incubated with FAM-UBI or NBD-UBI demonstrating an improved signal to noise ratio with NBD which avowed the majority of bacteria to be detected (shown in middle column). This was compared with FAM-UBI which detected a minor subset of clumped bacteria. B) NBD-UBI also exhibits specificity for bacteria (Pseudomonas aeruginosa) over mammalian cells (white arrow).
Figure 1:
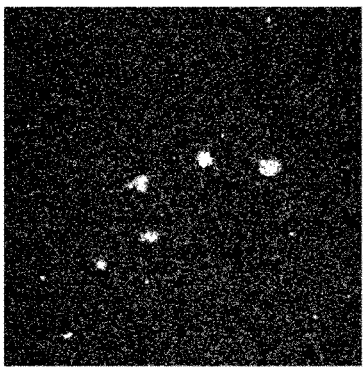
Figure 1:
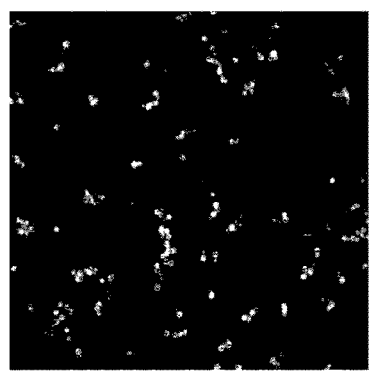
Figure 1:
Figure 1:
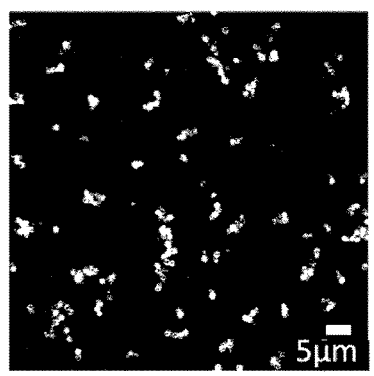
Figure 1:
Figure 1:
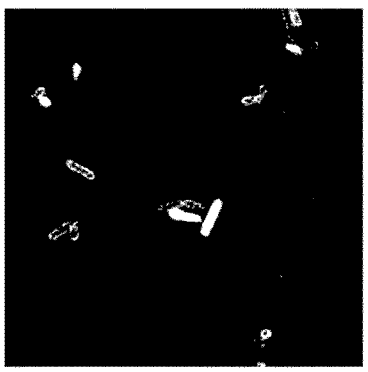
Figure 1:
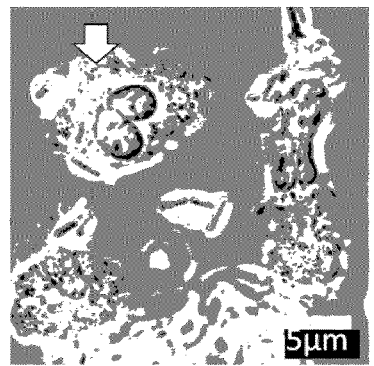

For the reporting of bacteria we synthesised a probe comprising the probe element only, and substituting the methionine of the ubiquicidin fragment UBI$_{29-41}$ for a norleucine, "NBD-UBI$_{Nle}$". This probe was compared to the same bacterial detecting moiety with another 'always on' fluorophore, fluorescein (FAM), "FAM-UBI$_{Nle}$", and showed an improved signal-to-noise on live benchtop confocal microscopy for the NBD reported (FIG. 1). Furthermore, it was confirmed that the labelling is specific to bacteria and not cell membranes in general. For example, FIG. 1 shows that isolated human neutrophils were not labelled by the NBD-UBI$_{Nle}$ probe, whilst the bacteria were labelled by the NBD-UBI$_{Nle}$ probe.

Figure 2:
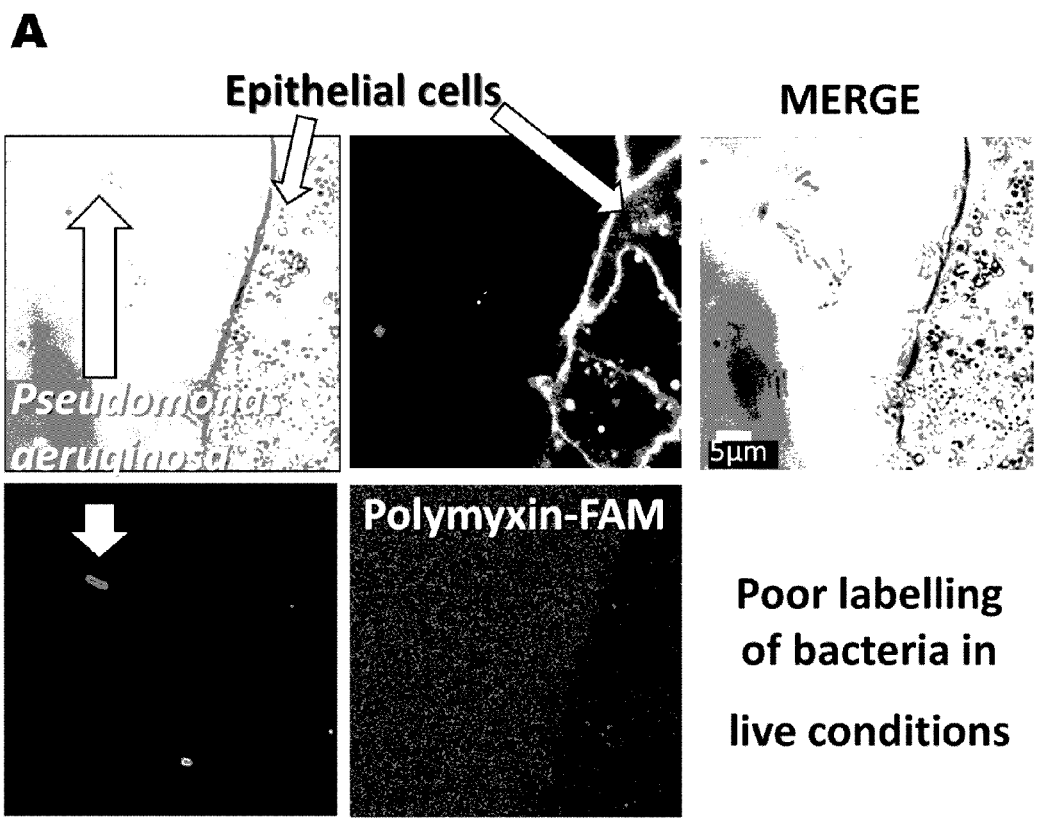
FIG. 2: FAM-PMX does not allow sufficient signal to noise to detect bacteria in vitro. A) Pseudomonas aeruginosa (PA), counterstained with FM-464 (left-hand images) and incubated with A549 cells (human lung epithelial cells highlighted in the middle image) demonstrate bacterial labeling is not seen above background but also there is no labeling of the epithelial calls. B) NBD-PMX (left-hand image) with a nuclear counterstain Syto 82 (middle image) allows bacterial labelling and retains selectivity of labeling over mammalian cells (right-hand image).
Figure 2:
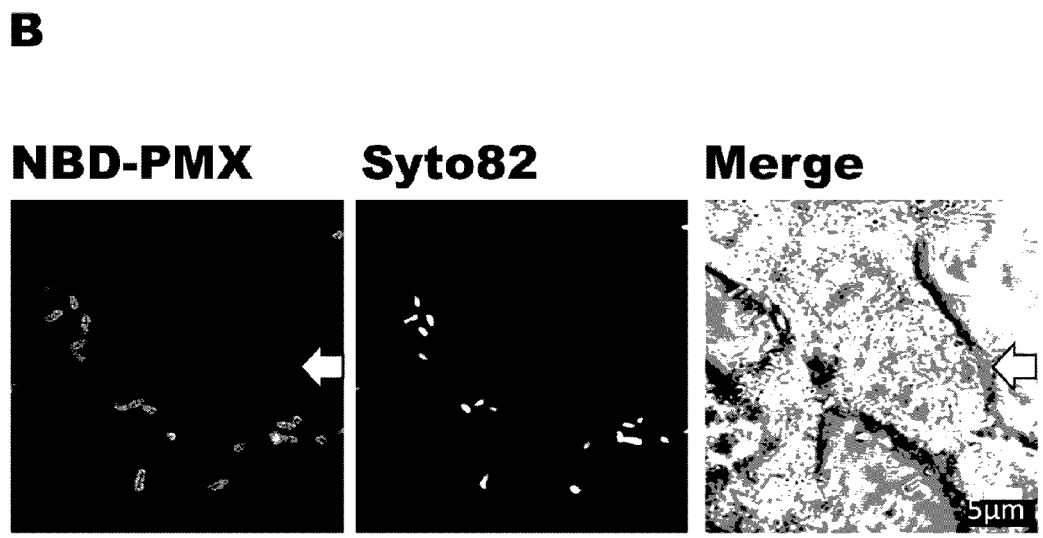

To confirm the same would be observed for the PMX bacterial detecting moiety we constructed NBD-PMX and FAM-PMX demonstrating an improved signal-to-noise with NBD-PMX over FAM-PMX and confirm this construct is also specific to mammalian cells (FIG. 2).

"Branched/Dendron" or "Multivalent" Probes

A probe comprising a core and three probe elements connected to the core (a "three branch" probe) was prepared (NBD-UBI$_{dend}$), each probe element comprising a NBD-UBI$_{Nle}$ moiety.

Figure 3:
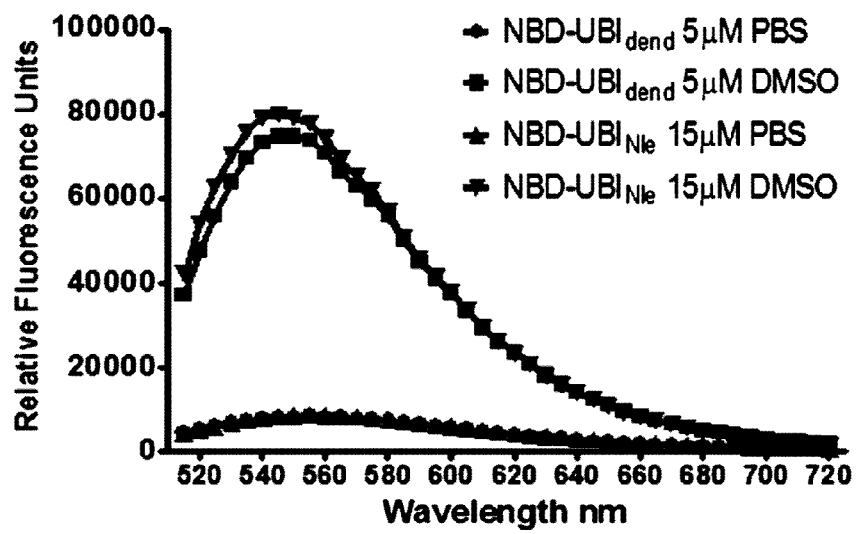
FIG. 3: Emission spectra of probes confirms increase in fluorescence in hydrophobic environments. A) Emission spectra shown for NBD-UBI$_{dend}$ (5 µM) and NBD-UBINle (15 µM) in the presence of PBS or DMSO (hydrophobic environment) when excited at 488 nm wavelength. B) Emission spectra shown for NBD-PMX (10 µM) in the presence of PBS or DMSO (hydrophobic environment) when excited at 488 nm wavelength. The fluorescence of both probes greatly increases under hydrophobic conditions as would be present upon binding to the target bacteria.
Figure 3:
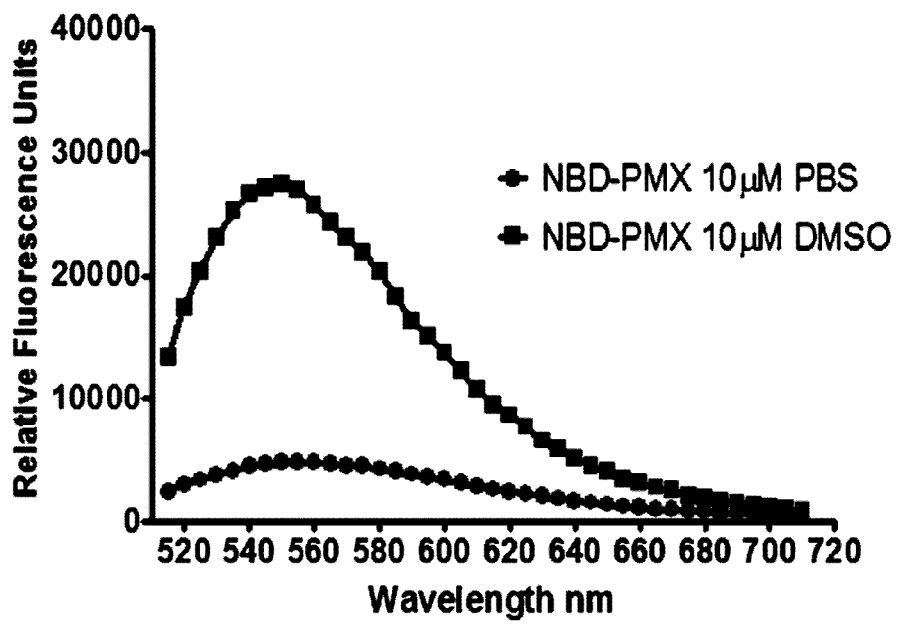

To confirm the fluorescent reporter NBD retains its characteristics when coupled with our peptide moieties we measured the fluorescence of the compounds in conditions to mimic a hydrophobic environment (DMSO). Linear NBD-UBI$_{Nle}$, NBD-UBI$_{dend}$ and NBD-PMX were excited at 488 nm (Biotek fluorescent plate reader) and demonstrated significant increase in fluorescence when the probes were in the presence of dimethyl sulfoxide (DMSO) (hydrophobic environment) when compared to phosphate buffered saline (PBS) (FIG. 3) confirming environmentally sensitive fluorescent reporting. NBD-UBI$_{dend}$ demonstrated the same fluorescence increase as linear when using eqimolar concentrations of NBD.

Figure 4:
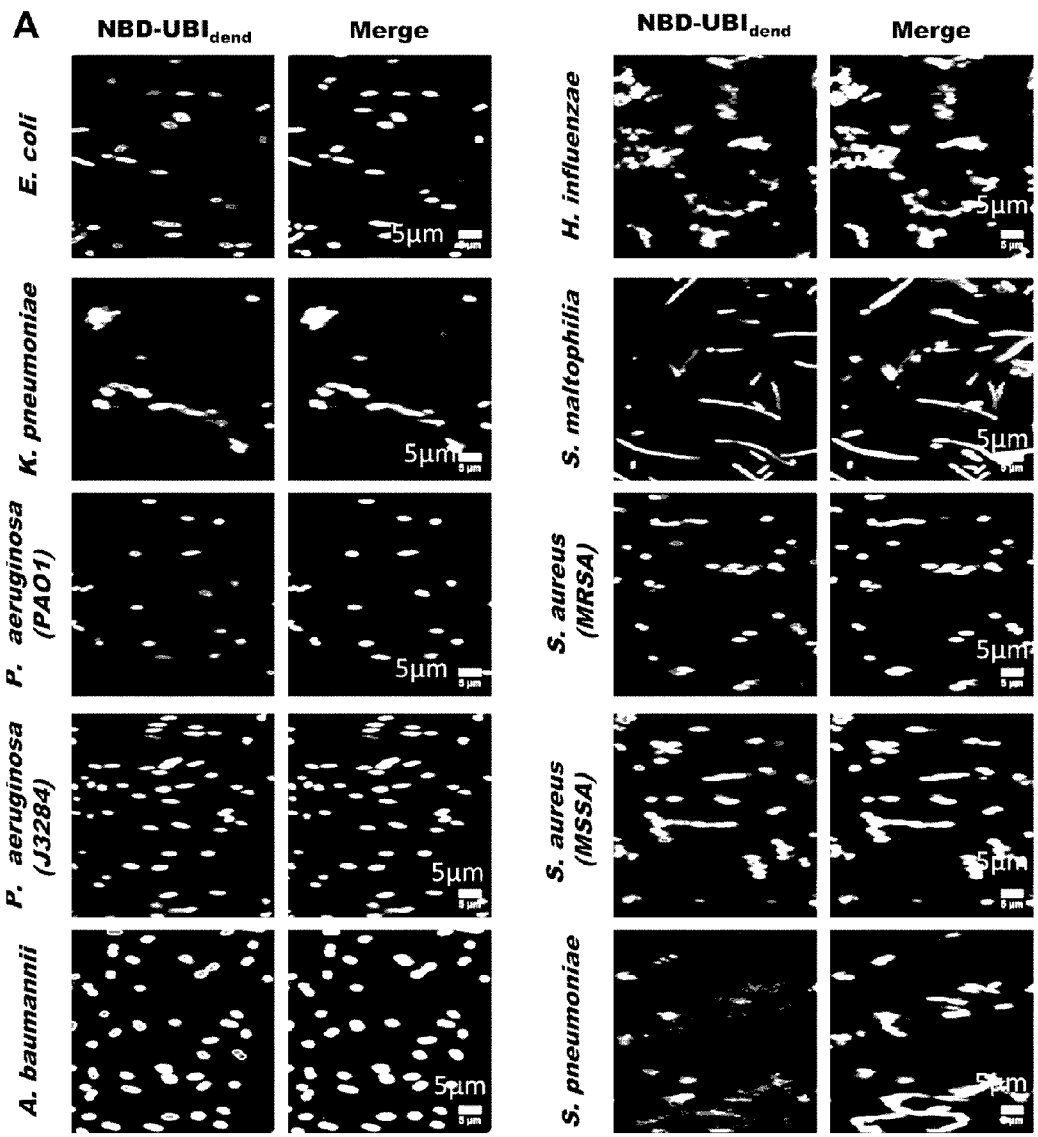
FIG. 4: NBD-UBI$_{dend}$ labels bacteria selectively over mammalian cells in vitro: A) Example images of a clinically relevant bacterial panel with NBD-UBI$_{dend}$ (5 µM; left-hand images) counterstained with the fluorescent generic cellular DNA dye Syto-82 imaged by laser scanning confocal microscopy. B) Quantification of bacterial panel labelling NBD-UBI$_{dend}$ 5 µM (optimal concentration) where every bacteria in the panel is brighter when compared with MSSA and NBD-UBI UBI$_{Nle}$ 105 µM (optimal concentration) C) Flow cytometry data with unstained bacteria (shaded), NBD-UBI$_{Nle}$ 155 µM (white) and NBD-UBI$_{dend}$ 55 µM labelled bacteria (white with grey outline orange). D) MSSA and NBD-UBI$_{dend}$ (5 µM; left-hand image), counterstained with Syto-82 and merge showing human neutrophils (white arrow) and E) A549 cells (white arrow) demonstrating no labelling of mammalian cells. Representative images shown, n≥3 for all experiments.
Figure 4:
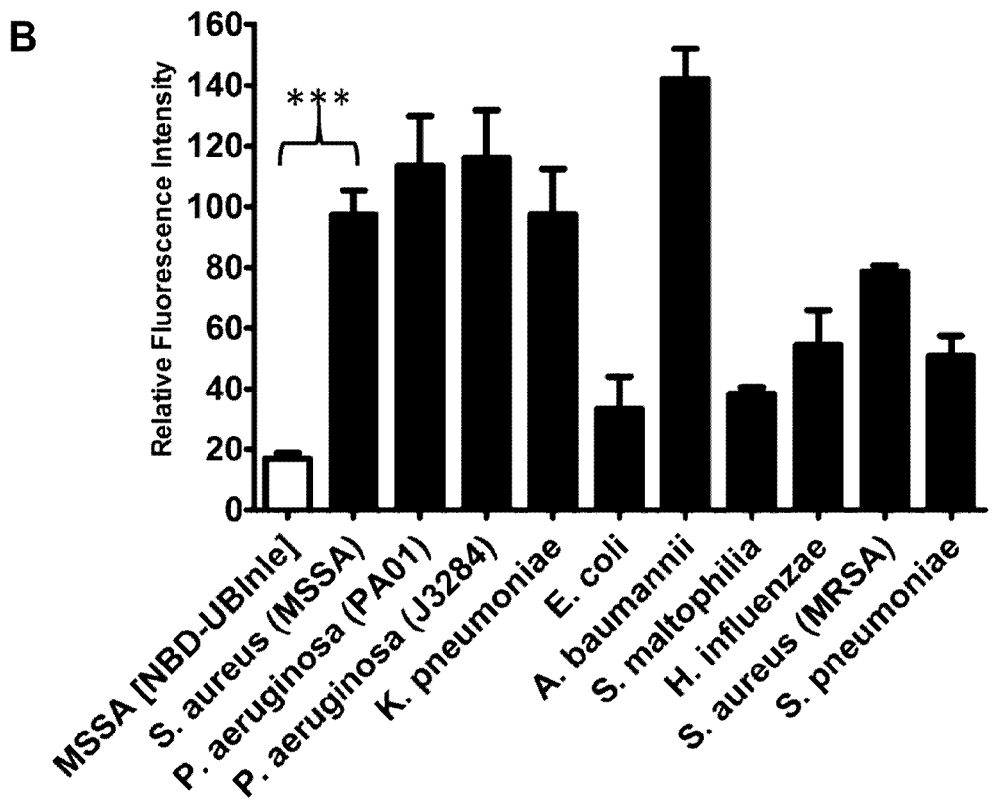
Figure 4:
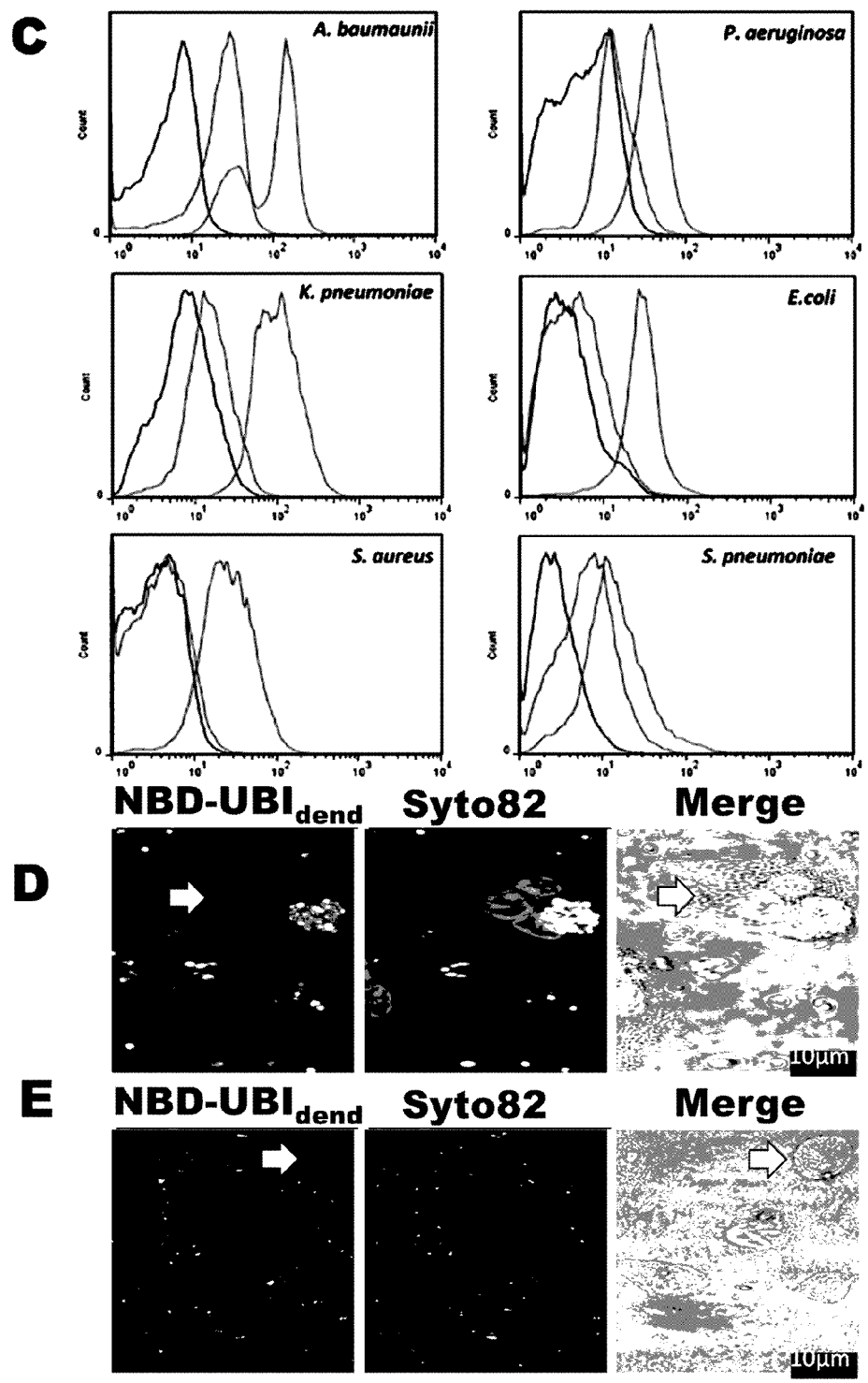

A panel of bacteria which represent >70% of VAP causing pathogens (Chastre J et al. Am J Respir Crit Care Med. 2002 Apr. 1; 165(7):867-903) (Gram-negative: *P. aeruginosa* (two strains), *A. baumannii, S. maltophilia, K. pneumoniae, E. coli* and *H. influenzae*. Gram-positive: Methicillin Resistant *S. aureus* (MRSA), Methicillin Sensitive *S. aureus* (MSSA) and *S. pneumoniae*) (strain list in Table 3 below) were labelled with NBD-UBI$_{dend}$. Labelling was observed with variable intensity (FIGS. 4A and B). Nevertheless all bacteria were brighter than MSSA labelled with linear NBD-UBI$_{Nle}$ (FIG. 4B) and on flow cytometry NBD-UBI$_{dend}$ demonstrated increased labelling over linear NBD-UBI$_{Nle}$ (FIG. 4C). Furthermore, NBD-UBI$_{dend}$ did not label human neutrophils or A549 cells supporting prokaryotic selectivity. (FIGS. 4D and E).

Figure 5:
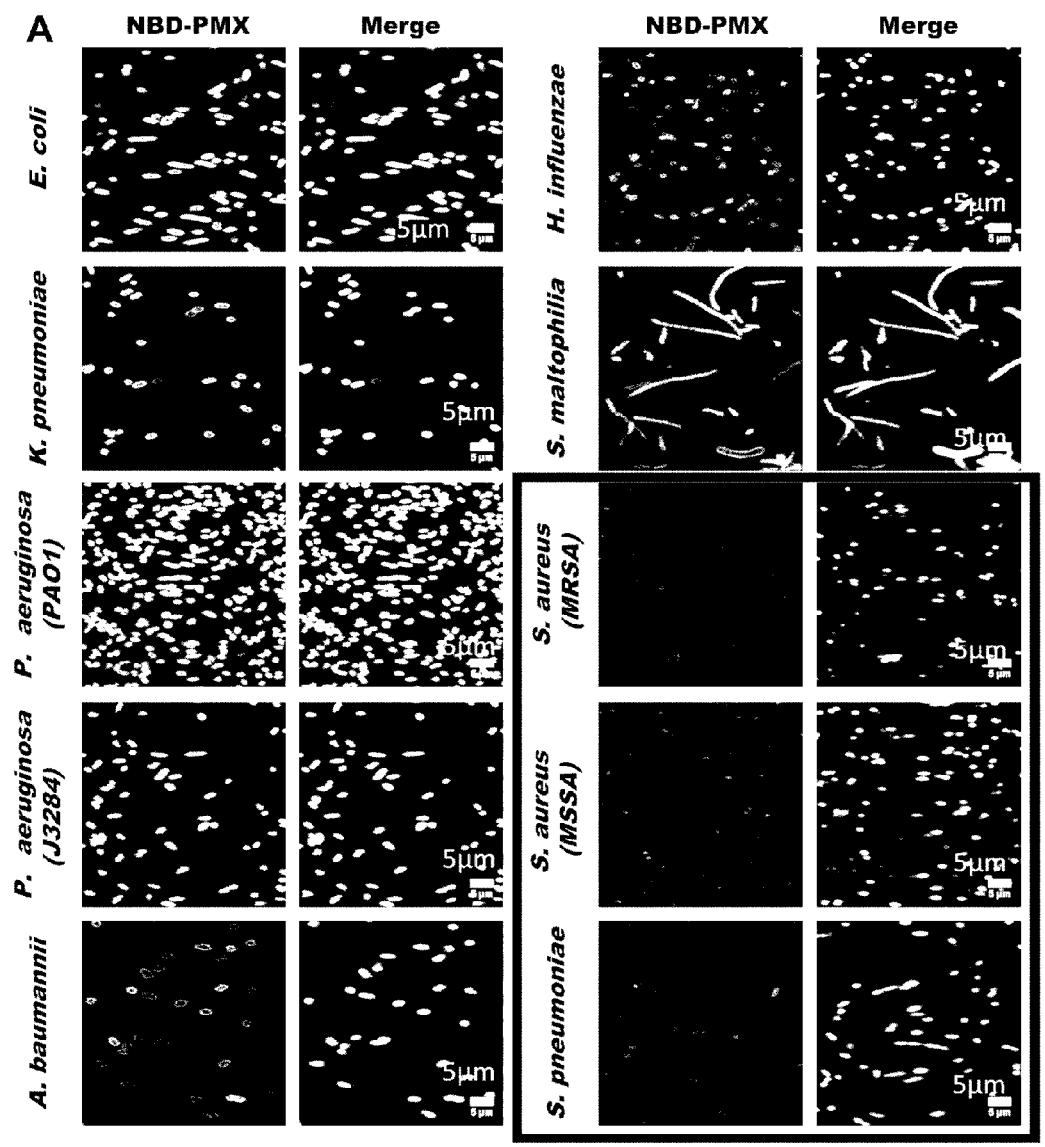
FIG. 5: NBD-PMX selectively labels Gram-negative bacteria in vitro, Example images of the bacterial panel with NBD-PMX imaged by laser scanning confocal microscopy. A) Bacterial panel with NBD-PMX 1 µM (left-hand column) and counterstain with syto-82. Gram-positive bacteria (bounded by black box) display minimal/no labelling compared with Gram-negative bacteria. B) Quantification of bacterial panel with NBD-PMX 1 µM with Gram-positive bacteria in white bars and Gram-negative in black bars, showing high intensity selective labelling of Gram-negative bacteria compared with Gram-positive bacteria. All Gram-negative bacteria showed a statistically significant increase over all Gram-positives. C) Flow cytometric evaluation of bacterial labelling with NBD-PMX showing unstained bacteria (shaded) and NBD-PMX (white) labelled bacteria. No significant labelling of Gram-positive bacteria (bounded by the box), D) MSSA and NBD-PMX 1 µM (left-hand images), counterstained with Syto-82 and merge showing human neutrophils (white arrow) and E) A549 cells (white arrow) demonstrating no labelling of mammalian cells (reproduced from FIG. 2), Representative images shown, n≥3 for all experiments.
Figure 5:
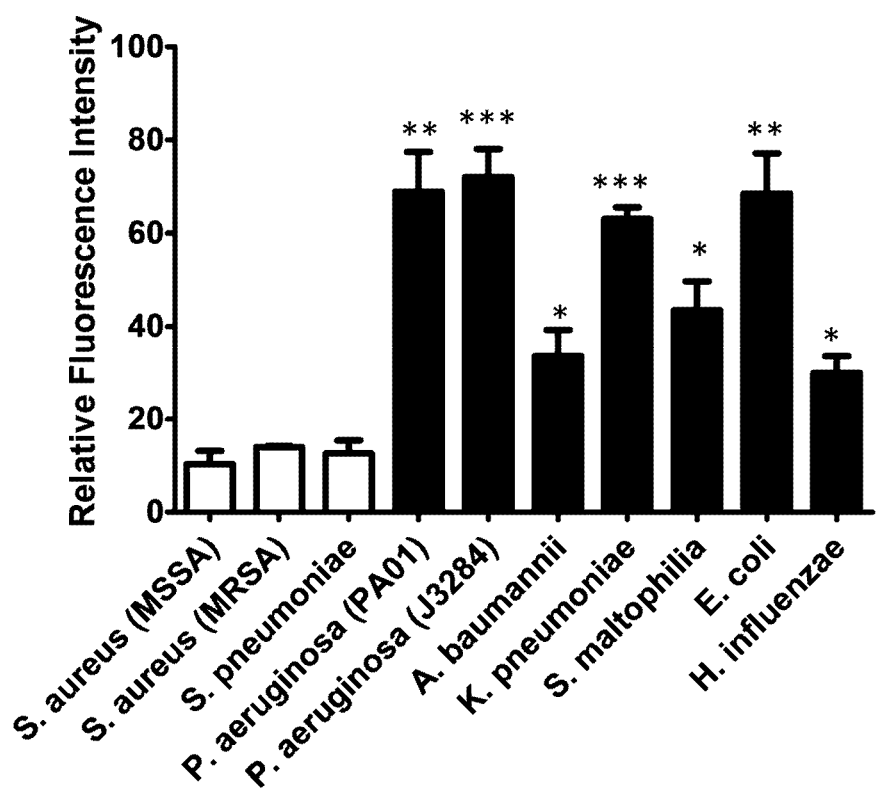
Figure 5:
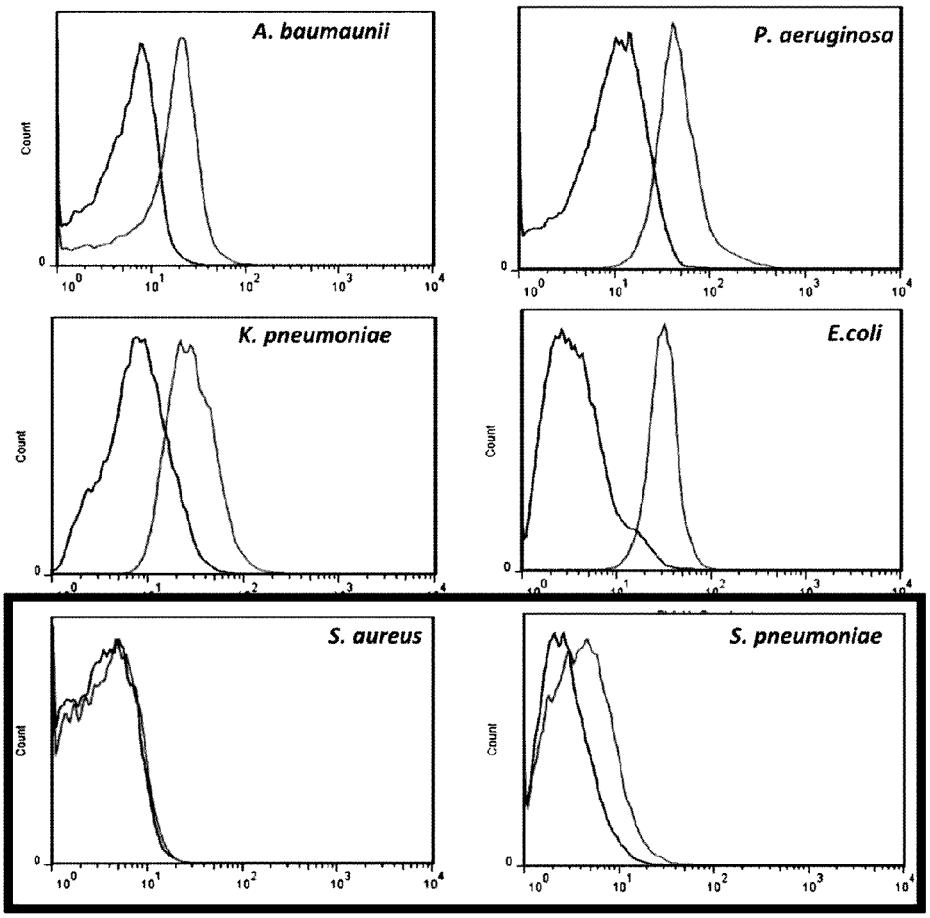
Figure 5:
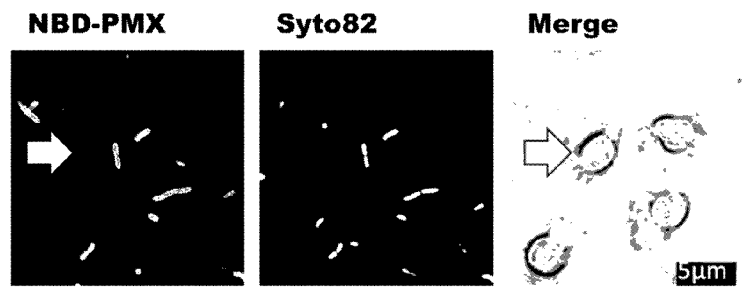
Figure 5:
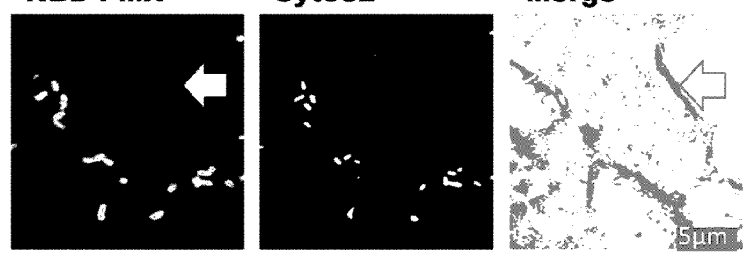

NBD-PMX incubated with bacteria, demonstrated significantly higher fluorescence on Gram-negative bacteria (*P. aeruginosa, A. baumannii, S. maltophilia, K. pneumoniae, E. coli* and *H. influenzae*) than Gram-positive bacteria (MRSA, MSSA and *S. pneumoniae*) ($p<0.05$) on confocal analysis (FIGS. 5A and B), which was confirmed by flow cytometry (FIG. 5C). Furthermore, there was no labelling of human neutrophils or A549 cells. (FIGS. 5D and E).

Figure 6:
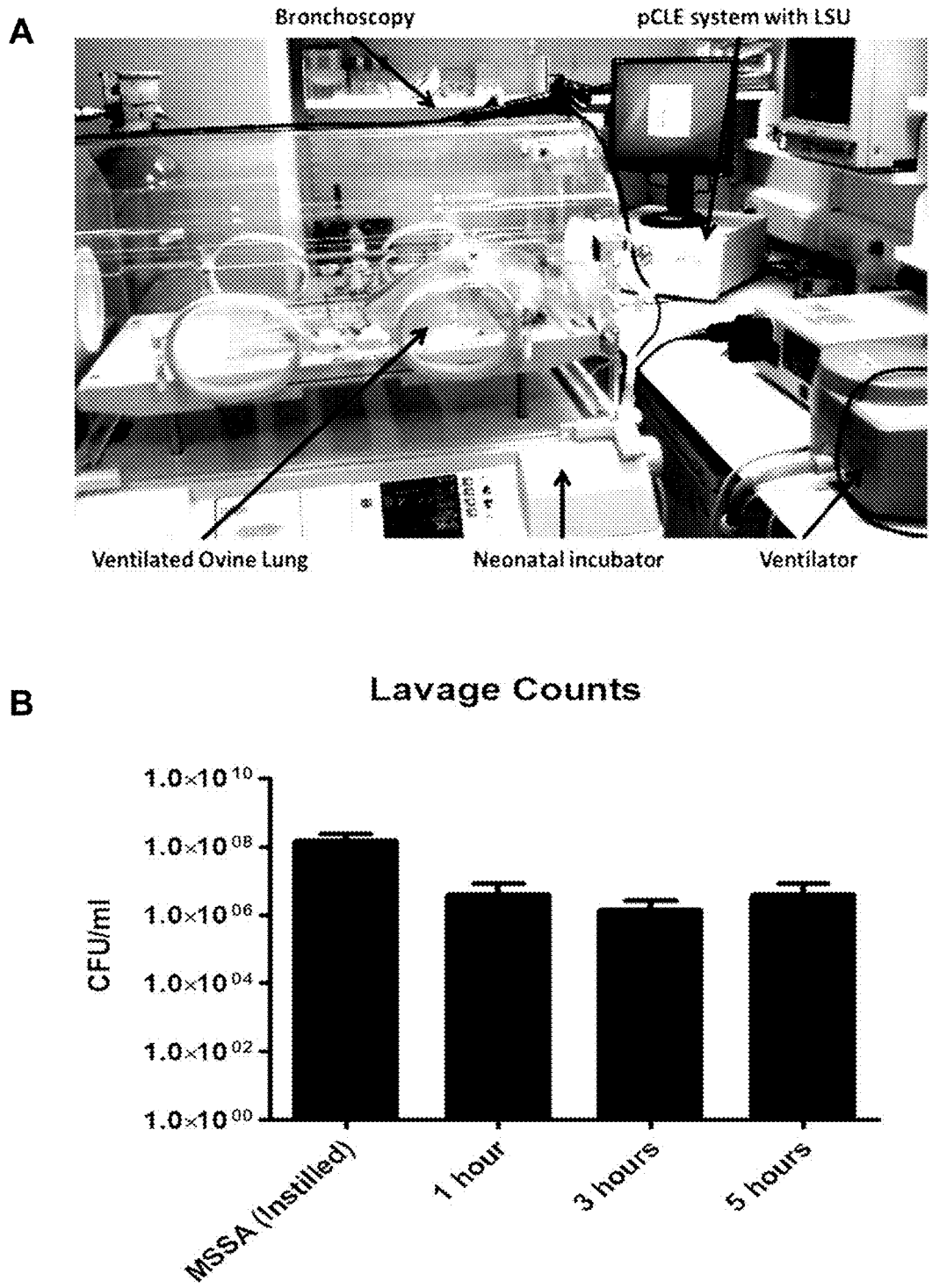
FIG. 6: Ex vivo model of bacterial infection. A) Ovine lungs were harvested, ventilated and placed in a neonatal incubator with ambient temperature of 37° C. Pulmonary segments were instilled with PBS (control) or bacteria via bronchoscopy. Probes were then instilled and segments imaged with fibered confocal fluorescence microscopy (FCFM) using 488 nm Laser Scanning Unit (LSU), B) Ex vivo ovine model demonstrates viable bacteria 5 hours following instillation. Bacteria (MSSA) instilled into segments of ovine lung and lavaged at 1, 3 and 5 hours (n=3), plated for CFU/ml and counted following 16 hour incubation.

NBD-UBI$_{dend}$ and NBD-PMX were assessed for in situ specificity and sensitivity in an ex vivo ovine model of bacterial infection (FIG. 6). In this model, the instillation of PKH fluorescent dye-labelled bacteria into the distal ovine lung and imaged with FCFM reveals a characteristic and distinctive pattern of punctate fluorescence in each field of view (FIG. 8). We observed identical patterns with Calcein-labelled bacteria and Green Fluorescent Protein-expressing *S. aureus* which were instilled into the lung and imaged with FCFM (FIG. 8). This pattern is reproduced identically by instilling bacteria "pre-labelled" with NBD-UBI$_{dend}$ and NBD-PMX into lung segments.

Figure 7:
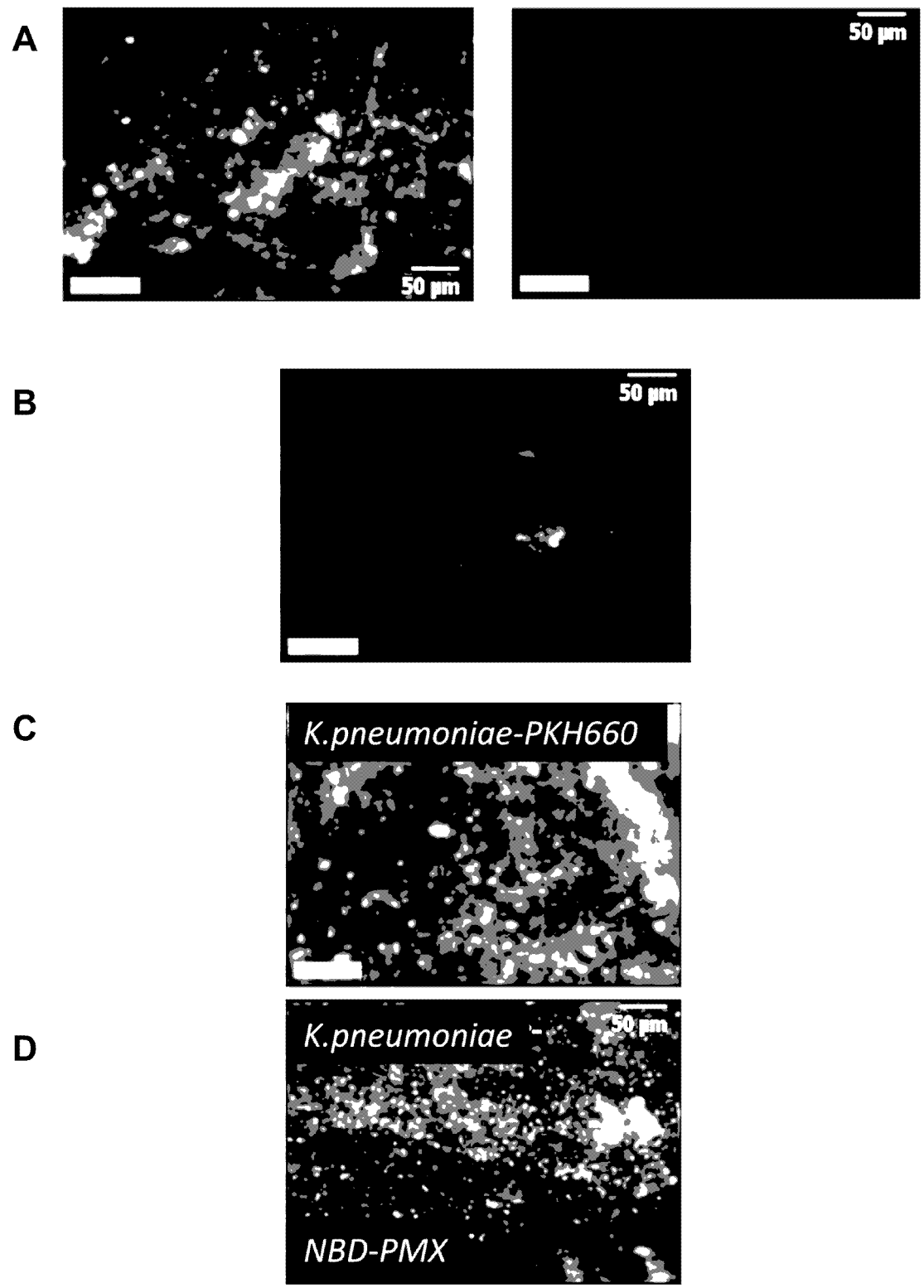
FIG. 7: NBD-UBINle fails to label bacteria in the ovine lunge There was no consistent labelling of bacteria in the ovine lung confirmed by counterstaining bacterial and imaging on a spectrally distinct imaging system. A: Lung segment with PKH660 labelled MSSA at 1 hour post-instillation, B: Control segment (instilled with PBS and no bacteria) imaged at 660 nm. C) The same segment imaged at 488 nm following 10 µM NBD-UBI$_{Nle}$ instillation. However, the same experiment with counterstained PKH660 labelled K. pneumoniae (Gram negative) shown in panel ID, with NBD-PMX added demonstrating the same punctate signal.

Following this thorough characterisation of the model and positive controls, we instilled PBS or VAP-relevant bacteria into distinct segments within the ex vivo lung model, followed by the microdosed delivery of probes according to the invention. We demonstrated that the linear NBD-UBI$_{Nle}$ could not label bacteria in situ despite the ability in vitro (FIG. 7). For these experiments the assays were repeated with counterstained gram-negative bacteria (*K. pneumoniae*) which demonstrated labelling with NBD-PMX (FIG. 7). However, In segments instilled with bacteria we demonstrated the same signal as seen with the 'positive controls' when NBD-UBI$_{dend}$ is instilled (*P. aeruginosa, S. aureus, E. coli* and *K. pneumonia*) but minimal/no signal with PBS control, confirming the ability to label bacteria in situ and image using the FCFM system (FIG. 9).

In segments instilled with Gram-negative bacteria, *P. aeruginosa* (laboratory strain PA01 and clinical VAP isolate J3284), *K. pneumoniae* and *E. coli*, we have demonstrated the same signal as in the 'positive controls' when NBD-PMX is instilled but no signal in segments with PBS or Gram-positive bacteria MSSA, MRSA and *S. pneumoniae* (FIG. 10). In these experiments we confirmed the equal density of Gram-positive and Gram-negative bacteria in all of the segments imaged with NBD-UBI$_{dend}$ and NBD-PMX by bronchoalveolar lavage (demonstrating no difference in CFU/ml between segments) and through counterstained bacteria imaged on a LSU at 660 nm.

To further demonstrate in situ bacterial detection and to assess the ability of the probes to image bacterial aggregation, we embedded bacteria in agarose beads which were then instilled into the lung. Microdosed probe instillation and FCFM imaging demonstrated that bacterial beads are clearly and exclusively detected whereas control beads (beads without bacteria) are not (FIGS. 9 and 10).

In the distal lung, there is likely to be significant and rapid dissipation of the probes immediately after delivery. Therefore, it is imperative that probe-bacterial labelling remains persistent under these conditions. NBD-UBI$_{dend}$-labelled bacteria retain labelling upon probe 'wash-off', as is seen for NBD-PMX. When instilled into the ovine lung, bacteria pre-labelled with NBD-UBI$_{Nle}$ are undetectable by FCFM whereas bacteria pre-labelled with NBD-UBI$_{dend}$ or NBD-PMX are readily visualised (FIG. 11). As such, this resistance to 'wash-off' represents a surrogate indicator of probe-bacterial affinity which appears to be an absolute requirement for distal lung in situ labelling. Currently, both NBD-UBI$_{dend}$ and NBD-PMX are resistant to wash-off whilst most of the other structural variants do not. Hence, bacteria labelled with both NBD-UBI$_{dend}$ and NBD-PMX retain sufficient intensity of fluorescence upon probe dissipation that occurs in the distal lung (FIG. 12).

Secondly we assessed stability of the probes in BALF from patients with ALI by FTMS and MALDI-TOF MS analysis. NBD-UBI$_{Nle}$, NBD-UBI$_{dend}$ and NBD-PMX were incubated for 30 minutes with BALF (FIG. 13). NBD-UBI$_{dend}$ and NBD-PMX demonstrate stability with peaks corresponding exactly to the predicted theoretical spectra of the intact probes readily identified in both saline and BALF incubated samples. Predicted spectra of breakdown products were also not seen. By contrast breakdown products of the NBD-UBI$_{Nle}$ were seen indicating instability in lavage fluid. Thus, probe stability and retention of function in the context of the 'inflamed' highly enzymatically-active distal lung environment is a key determinant of in vivo utility. This was confirmed by imagining in the presence of ovine lavage, which demonstrated higher fluorescence intensity of NBD-UBI$_{dend}$ over the linear compound, and no reduction in intensity for NBD-PMX when imaged in ovine lavage (FIG. 14).

In vitro experiments were conducted using lung surfactant constituents to investigate the ability of probes to preferentially detect bacteria in the presence of large amounts of surfactant. The nature of the fluorescent reporter (NBD) incorporated in NBD-UBI$_{dend}$ and NBD-PMX, suggested the possibility of fluorescent activation in the hydrophobic 'rich' surfactant environment. A suspension of surfactant constituents in buffered saline was prepared (20 mg/ml, 65% dipalmitoylphosphatidylcholine, 30% phosphatidylglycerol, 5% palmitic acid with 1 mg/ml tyloxapol as a spreading agent) and incubated with and without A549 epithelial cell monolayer. Particles of surfactant constituents seen to coat the epithelial cell-surface were fluorescent suggesting the NBD fluorescence increases in this hydrophobic solution. We clearly demonstrate that NBD-UBI$_{dend}$ and NBD-PMX both possess selectivity for bacterial labelling over lung surfactant constituents. At equivalent molarity, the NBD-UBI$_{dend}$ has significantly improved bacterial selectivity over linear NBD-UBI$_{Nle}$ in the presence of surfactant constituents (FIG. 15). Despite a mechanism relying on fluorescence increase in hydrophobic environments by NBD, both NBD-UBI$_{dend}$ and NBD-PMX preferentially increase in fluorescence on bacteria over purified surfactant constituents, in keeping with their ability to image bacteria in the distal lung. Although the comparative distribution and relative abundance of surfactant constituents in the lung is unknown it is entirely likely that this contributes to the background fluorescence that is observed upon probe instillation and that retention of labelling in vitro in the presence of surfactant is required for the probe to image successfully, providing it is sufficiently resistant to degradation and retains labelling upon wash-off.

Elastase (HNE) Sensitive Probes

Example 1

A first example of elastase sensitive probes (shown schematically in FIG. 16A) comprises methyl red (acting as a dark quencher) connected via the peptide sequence AAPV (SEQ. ID NO: 9). (acting as the enzyme cleavable peptide sequence of the cleavable linker) to 7-nitrobenz-2-oxa-1,3-diazole (NBD) and the ubiquicidin fragment UBI$_{29-41}$ (together acting as the probe element). Accordingly, the NBD fluorescence is quenched by the methyl red and no fluorescent signal will be observed (i.e. the methyl red and NBD are acting as a FRET pair) and therefore, whether or not the probe is bound to any bacteria that may be present in the target area via UBI$_{29-41}$, no signal is observed using confocal microscopy.

When the probe is in the presence of human neutrophil elastase (HNE), such as in inflamed tissue, HNE cleaves the peptide sequence of the linker, to thereby free the probe element from the methyl red quencher. Accordingly, the NBD fluorophore is no longer quenched and produces a fluorescent signal. In addition, due to the environmental sensitivity of the NBD, the signal produced is greatly amplified if the NBD is in a hydrophobic environment, such as within a cell membrane.

FIG. 16B shows confocal images for a sample comprising the probe incubated with a co-culture of bacteria and neutrophils. These images confirm the ability of the probe to be cleaved by neutrophil derived HNE and to label bacteria. When the elastase inhibitor sivelestat was added to the medium, no labelling was observed as the probe remains uncleaved (and therefore the NBD is quenched by the methyl red).

Example 2

In a second example, the probe comprises carboxytetramethylrhodamine (TAMRA, acting as a fluorescent quencher) connected to NBD and polymyxin (acting as the probe element) via the peptide sequence AAPV (SEQ ID NO: 9) (acting as the enzyme cleavable peptide sequence of the cleavable linker). Accordingly, the NBD fluorescence is quenched by the TAMRA to give rise to a fluorescent signal from TAMRA (i.e. the TAMRA is accepting the energy absorbed by the NBD and is itself fluorescing, TAMRA and NBD are acting as a FRET pair). Accordingly, whether or not the polymyxin has bound to any bacteria that may be present, only a signal from the TAMRA is observed.

Once the probe has been cleaved by elastase, the bacteria are labelled by the probe element due to the fluorescence of NBD (FIG. 17A), whereas the neutrophils, once activated, are labelled by the TAMRA moiety (FIG. 17B). Furthermore, we demonstrate the fluorescence of the cleaved TAMRA compound increases in an elastase dependent manner and are inhibited with an elastase inhibitor such as sivelestat ("S", FIG. 17C).

Data Analysis

We have begun to develop bespoke image analysis/processing strategies to perform rapid real-time objective analysis of the large datasets generated by the probe/FCFM platform. Unequivocal detection of bacteria and the delineation of their Gram status will be achieved by employing these image processing algorithms in real-time. A processing algorithm based upon single frame analysis has been applied to entire video sequences (up to 3500 frames), and even at this early stage we are able to unequivocally delineate bacterial presence and Gram status. These signal and image processing algorithms will be rapidly iterated in readiness for clinical application, and we expect significant components of machine-learning to be incorporated into further optimisation of NBD-UBI$_{dend}$ and NBD-PMX datasets.

Figure 18:
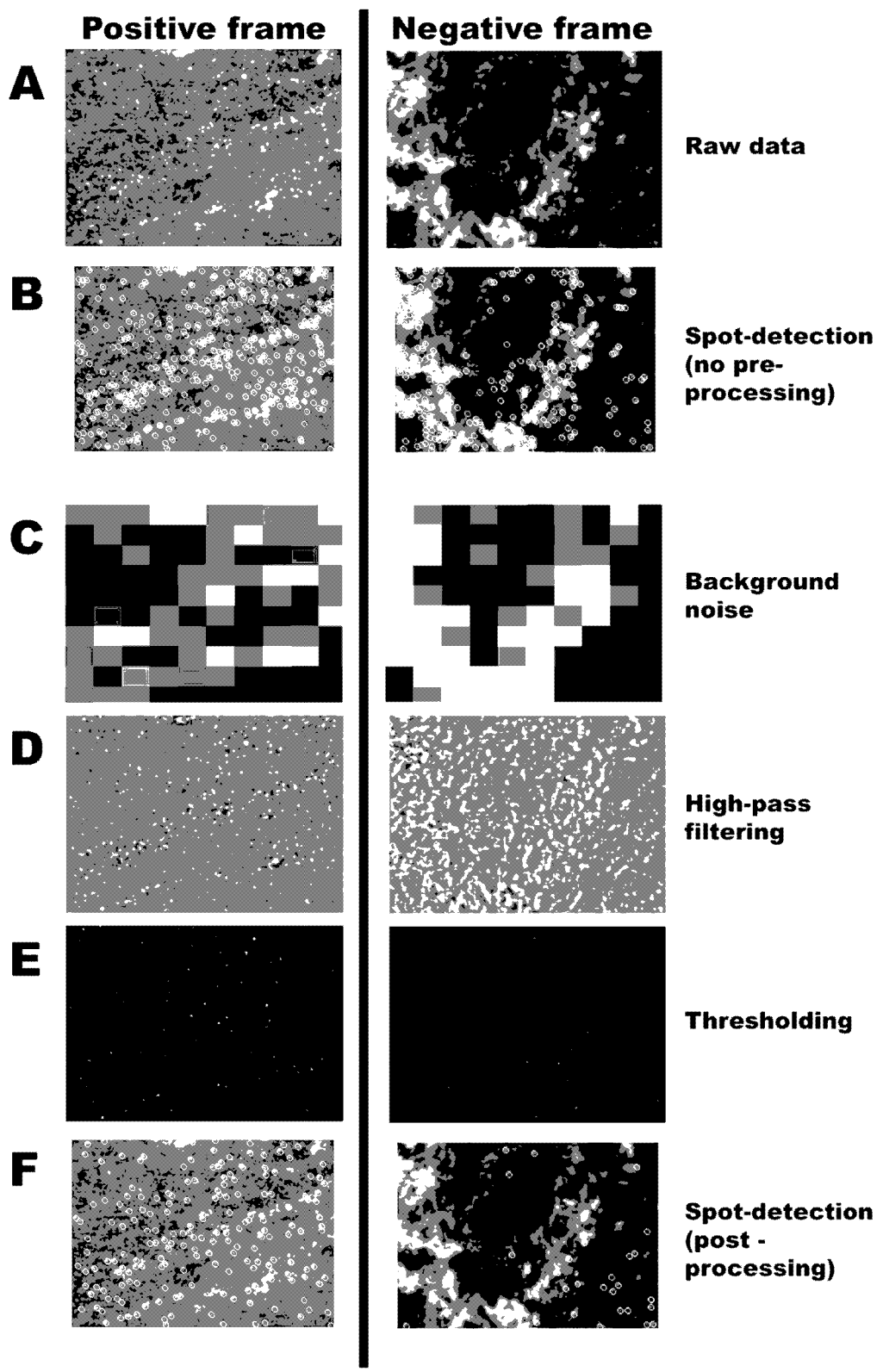

FIG. 18 shows the stepwise processing for single positive and negative frames that were initially chosen to develop the model, based on two image processing algorithms (The Laplacian of Gaussian (LoG) and the Difference of Gaussians (DoG)) commonly used to detect bright spots in fluorescence microscopy images in an objective computational manner. Spots are enhanced in an image by convolving with a LoG or DoG filter. Pre-processing is necessary to improve the accuracy by removing the influence of noise in the image. First, background noise is estimated by dividing an image into small windows (100 per frame) and then calculating the standard deviation of the pixel intensities. High-pass filtering is used to decrease low frequency noise. Thresholding the resulting image at 3× standard deviation removes background noise and keeps only the higher pixel intensity values. Finally, spots are detected with LoG or DoG.

We have employed the method described above to analyse entire FCFM image videos (up to 3500 frames). With an initial thresholding limit of 80 spots per frame to indicate a positive frame, we determined the percentage positive frames per video and set an arbitrary 'cut-off' of 20% as the threshold for a binary outcome of YES/NO. This shows unequivocal detection of bacteria and Gram status using NBD-UBI$_{dend}$ and NBD-PMX respectively (FIG. 19).

To ensure the compounds can label bacteria above the normal human lung autofluorescence, bacteria were incubated with human lung tissue and imaged using FCFM and on benchtop confocal (FIG. 20) demonstrating that bacteria can be detected, once labelled, above the level of autofluorescence.

We have identified a number of determinants of distal lung in situ labelling with probes. These explain why the promising in vitro data for the linear NBD-UBI$_{Nle}$ probe did not translate to reproducible in situ labelling in the ovine lung. Structural variants were synthesised and assessed, exploring the structure-activity-relationship. The initial aims were to improve resistance to degradation and improve signal-to-noise. Certain modifications which greatly improved a single functional aspect such as stability (such as insertion of D-amino acids/N-methyl or variants including exclusive D-amino acid variants) or labelling intensity did not permit reproducible visualisation of bacteria in the distal lung. We comprehensively assessed the UBI analogues for stability in ALI BALF, in vitro labelling of bacteria using live benchtop confocal imaging at 37° C. and in situ labelling in the ovine lung.

A number of structural modifications have been undertaken which are broadly divided into two groups:
(a) Increase the signal-to-noise ratio by examining different environmentally-sensitive fluorophores or increasing the NBD-UBI$_{Nle}$ payload.

We have assessed the utility of including two NBD fluorophores for each UBI fragment and have also assessed this with an N-methylated amino acid variant designed to enhance stability. We have assessed a series of alternative environmentally-sensitive fluorophores, including malachite green and styryl-based dyes, with the aim of producing a higher signal-to-noise ratio, which may enable lower levels of bacterial detection or detection at lower effective probe concentrations.
(b) Improve the resistance to proteolytic degradation.

We have assessed a number of compounds including variants incorporating D-amino acids and N-methylated amino acids at selected positions identified by MALDI analysis of the parent NBD-UBI compound as sites susceptible to proteolytic degradation. To reduce degradation without altering the amino acid constituents we have synthesised variants including PEG units at the amino and/or carboxy termini in order to block degradation from the ends of the peptide sequence. We have also synthesised and assessed variants consisting entirely of D-amino acids and D-amino adds with inversion of sequence with or without blocking PEG units. Furthermore, a cyclic variant of NBD UBI$_{Nle}$ has also been assessed as well as further variants of this compound incorporating IN-methylated amino adds at selected positions identified by MALDI analysis of the cyclic variant of NBD-UBI$_{Nle}$ as remaining susceptible to proteolytic cleavage

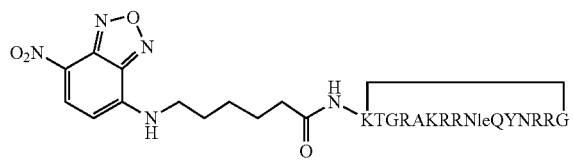

Cyclic variant of NBD-UBI$_{Nle}$ (SEQ ID NO: 19)

All compounds have undergone biological assessment. For stability we have assessed each compound in the presence of 0.9% NaCl (Saline) or pooled lavage fluid from patients with acute lung injury and analysed by matrix-assisted laser desorption/ionization (MALDI) or fourier transform mass spectrometry (FTMS). In vitro labelling was assessed on benchtop confocal in the presence of compound with bacteria and labelling was compared to NBD-UBI$_{Nle}$ which served as a reference control for bacterial labelling. Where appropriate we have also assessed labelling of the compound on isolated human neutrophils and primary human cell lines (A549 human lung adenocarcinoma cell line). For the ex vivo and in vivo ovine lung experiments each compound was assessed in a control lung segment (instilled with 2 ml PBS) or a bacterial segment (instilled with 2 ml of 2 optical density of bacteria). Following bacterial instillation, the compound was administered to the segment of interest and this was imaged by probe based FCFM.

Assessment of the different NBD-UBI$_{Nle}$ variants has given us a clearer understanding of different mechanistic factors affecting the function of the probe in the lung environment, and specifically clarified the reasons why, out of all the UBI variants, only the NBD-UBI$_{dend}$ is able to image bacteria in the lung.

The alternative fluorophores were inferior to NBD for this application. A Malachite Green variant gave a much lower labelling intensity on the bacteria and although the Styryl-dye compounds exhibited an increased intensity of labelling on bacteria these compounds had a decrease in selectivity over mammalian cells, most likely due to the propensity of the dyes themselves to enter lipophilic membranes overcoming the targeting of the ubiquicidin moiety. Consequently, the styryl-dye variants exhibited greatly increased off-target labelling in the ex vivo lung and no bacterial signal was observed.

The D-amino acid variants as well as the variants with PEG blocking groups at the ends of the peptide sequence exhibited reduced labelling in vitro and no labelling ex vivo. Despite improved stability, of the linear UBI variants which retained function in vitro none of these were able to image bacteria in the lung. We have obtained evidence that the wash-off properties of the probes, most likely related to affinity and/or the nature of subsequent insertion into the bacterial membrane, impact on whether or not they can be used to successfully image in the lung. The retention of labelling upon removal of probe solution was investigated in vitro by confocal. With all of the linear UBI variants labelling was lost completely upon wash-off. This suggests that, in the lung, labelling would be rapidly lost once the probe concentration around the bacteria decreased as a consequence of fluid dissipation. Bacteria were pre-labelled with these linear NBD-UBI$_{Nle}$ compounds and successful labelling was confirmed by imaging the bacterial suspension pre-instillation. These suspensions were instilled into the ex vivo lung and when the segment was subsequently imaged by FCFM no bacterial signal was detected (there is an inherent time-delay in change-over from the instillation catheter to passage of the FCFM fibre into the same segment). However when bacteria pre-labelled with NBD-PMX, which didn't lose labelling upon wash-off when assessed by in vitro confocal, were instilled a bacterial signal was detected. The NBD-UBI$_{dend}$ construct, as well as giving an increased bacterial signal at equimolar concentrations, retained labelling upon wash-off. As predicted, when bacteria pre-labelled with these compounds were instilled into the ex vivo lung the bacteria were successfully imaged.

We tested the compounds ability to label non-bacterial pulmonary pathogens, including fungi. Within immunocompetent patients the development of VAP secondary to eukaryotic fungi is uncommon, and accounts for <2% of VAP cases. The most commonly isolated pathogens are *Candida albicans* (*C. albicans*) and *Aspergillus fumigatus* (*A. fumigatus*). *C. albicans* colonises up to 50% patients in the ICU and colonisation increases with antibiotic use. However, the development of invasive candidiasis as a cause of VAP is rare and remains contentious. Indeed some large clinical trials have excluded *candida* isolation in their diagnostic algorithms for VAP and post-mortem studies have demonstrated growth of *candida* from BAL is not a reliable marker of *candida* infection in the immunocompetent patient. *A fumigatus* is also occasionally isolated in 1-2% of respiratory samples in critically ill patients. However, of this 1-2% only 20% are believed to be pathogenic and the remaining 80% are believed to colonisation.

NBD-UBI$_{dend}$ demonstrated no labelling of *C. albicans*, however, there was variable labelling of *A. fumigatus* hyphae upon imaging (FIG. 21). Furthermore, imaging demonstrated the fungal hyphae are significantly larger than bacteria and show a distinct morphological appearance. NBD-PMX demonstrated an identical pattern to NBD-UBI$_{dend}$ when imaged on confocal with the retention of labelling of Gram-negative bacteria, variable labelling of *A. fumigatus* hyphae and no labelling of *C. albicans* (FIG. 22).

Finally, to detect if this pattern would be identified in lung tissue, *A. fumigatus* was co-cultured with ovine lung and the probes and imaged with FCFM. This again demonstrated the size and pattern of the fungal hyphae to be distinct from a bacterial signal (FIG. 24). Similar experiments were conducted with suspensions of *A. fumigatus* and demonstrate a distinct characteristic, linear pattern of fluorescence which differs to a bacterial signal (FIG. 25).

NBD-PMX and NBD-UBI$_{dend}$ were assessed for direct red cell toxicity by a haemolysis assay and demonstrated no red cell haemolysis up to 100 µM (FIG. 26). The compounds were assessed for toxicity in a rodent single dose, intratracheal toxicity assessment. Mice received a single intratracheal administration of 100 µg/25 g mouse (3000 fold human dose assuming 100 µg delivered to a 75 kg man) of NBD-UBI$_{dend}$ or NBD-PMX, or PBS control. Mice were then euthanized at 48 hours and 14 days (n=3 per group). The data shows no toxicity for NBD-PMX (Table 2 and FIG. 27A) or NBD-UBI$_{dend}$ (Table 1 and FIG. 27B).

TABLE 1

| | NBD-UBI$_{dend}$ | | | | | |
|---|---|---|---|---|---|---|
| | 48 hours | | | 14 days | | |
| | PBS Control | NBD-UBI$_{dend}$ | | PBS Control | NBD-UBI$_{dend}$ | |
| Cytospin (% of Mononuclear cells/ Neutrophils/Red Blood Cells) | 96.5/0.7/0 ± 0.7/0.67/0 | 96.4/3.6/0 ± 2.0/2.0/0 | ns | 100/0/0 ± 0/0/0 | 100/0/0 ± 0/0/0 | ns |
| BALF (Cells/ul) | 354.9 ± 66.6 | 477.1 ± 150.6 | ns | 361.1 ± 38.6 | 342.7 ± 6.5 | ns |
| PenH value | 0.5 ± 0.04 | 0.5 ± 0.06 | ns | 0.38 ± 0.03 | 0.5 ± 0.04 | ns |
| Creatinine (u/l) | 8.0 ± 0.6 | 8.3 ± 0.7 | ns | 12.7 ± 1.7 | 9.0 ± 1.5 | ns |
| Bilirubin (u/l) | 2 ± 0 | 2 ± 0 | n/a* | 2 ± 0 | 2 ± 0 | n/a* |
| ALT (u/l) | 33.3 ± 3.9 | 24.0 ± 1.2 | ns | 39.3 ± 10.8 | 28.3 ± 1.9 | ns |
| ALP (u/l) | 120.0 ± 6.2 | 222.3 ± 80.3 | ns | 178.3 ± 27.4 | 227.0 ± 27.1 | ns |
| Albumin (u/l) | 21.0 ± 1.0 | 22.3 ± 1.8 | ns | 24.3 ± 0.7 | 25.0 ± 1.2 | ns | ns = not significant.
*Bilirubin for these time points was below 2 for all animals.

TABLE 2

| | NBD-PMX | | | | | |
|---|---|---|---|---|---|---|
| | 48 hours | | | 14 days | | |
| | PBS Control | NBD-PMX | | PBS Control | NBD-PMX | |
| Cytospin (% of Mononuclear cells/ Neutrophils/Red Blood Cells) | 97.1/0.3/2.6 ± 2.9/0.3/2.6 | 96.1/0/3.9 ± 3.9/0/3.9 | ns | 100/0/0 ± 0/0/0 | 93.0/0/2.3 ± 2.3/0/2.3 | ns |
| BALF (Cells/ul) | 243.1 ± 80.5 | 509.0 ± 270.2 | ns | 478.4 ± 88.4 | 542.0 ± 84.7 | ns |
| PenH value | 0.7 ± 0.1 | 0.5 ± 0.05 | ns | 0.4 ± 0.03 | 0.5 ± 0.07 | ns |
| Creatinine (u/l) | 35.3 ± 28.9 | 16.3 ± 8.8 | ns | 8.7 ± 1.8 | 9.7 ± 0.3 | ns |
| Bilirubin (u/l) | 2.4 ± 0.4 | 1.2 ± 0.4 | ns | 2.4 ± 0.3 | 1.2 ± 0.4 | ns |
| ALT (u/l) | 43.0 ± 14.0 | 36.0 ± 9.0 | ns | 32.3 ± 7.9 | 40.3 ± 4.8 | ns |
| ALP (u/l) | 100.0 ± 18.7 | 107.7 ± 17.3 | ns | 89.0 ± 8.1 | 126.3 ± 8.5 | ns |
| Albumin (u/l) | 24.7 ± 0.3 | 23.7 ± 0.3 | ns | 24.0 ± 0.6 | 25.3 ± 0.7 | ns | ns = not significant.

Methods of Synthesis of Probes

Synthesis of Ubiquicidin Based Elastase Probes ("Methyl Red (MR)-AAPV-NBD-UBI$_{29-41}$" and "TAMRA-AAPV-NBD-UBI$_{29-41}$") (SEQ ID NO: 9)

MR-AAPV-K(NBD)-PEG-OH (SEQ ID NO: 20) (AL3-74) fragment was synthesised on solid-phase employing Fmoc-strategy, with standard amino acid coupling cycles (2×30 min at rt) with DIC and oxyma in peptide grade DMF at ~0.1 mM reagent concentration. Fmoc deprotection steps were done in 20% piperidine in DMF (2×30 min). Between each step, the resin was washed with DMF, DCM and MeOH.

2 g of chlorotrityl polystyrene resin (loading ~0.3 mmol/g) was treated with Fmoc PEG-OH (3 eq) and DIPEA (6 eq) in anhyd. DCM (2 mL) for 3 h. After washing and Fmoc deprotection, the Fmoc-AAPVK(Dde) sequence (SEQ ID NO: 20) was synthesised as described above using, Fmoc-Lys(Dde)-OH, Fmoc-Val-OH, Fmoc-Pro-OH, and Fmoc-Ala-OH, After the sequence was completed, the synthesis was continued with half of the resin (0.3 mmol scale) and Ode protecting group was orthogonally removed with NH$_2$OH/imidazole in NMP/DCM (2×90 min). The resin was treated with NOB-Cl (3 eq) and DIPEA (6 eq) in DMF (2×45 min). After Fmoc deprotection, the synthesis was continued in 0.15 mmol scale and Methyl Red was coupled to the N-terminus as described above, After washing, the fragment was cleaved off the resin with TFA-TIS-H$_2$O (95:2.5:2.5) (30 min) and precipitated with cold ether to give AL3-74 (ESI-MS 1044.4 and 1066.4).

Scheme 1 Synthesis of Methyl Red-AAPV-NBD-UBI$_{29-41}$ (SEQ ID NO: 9)
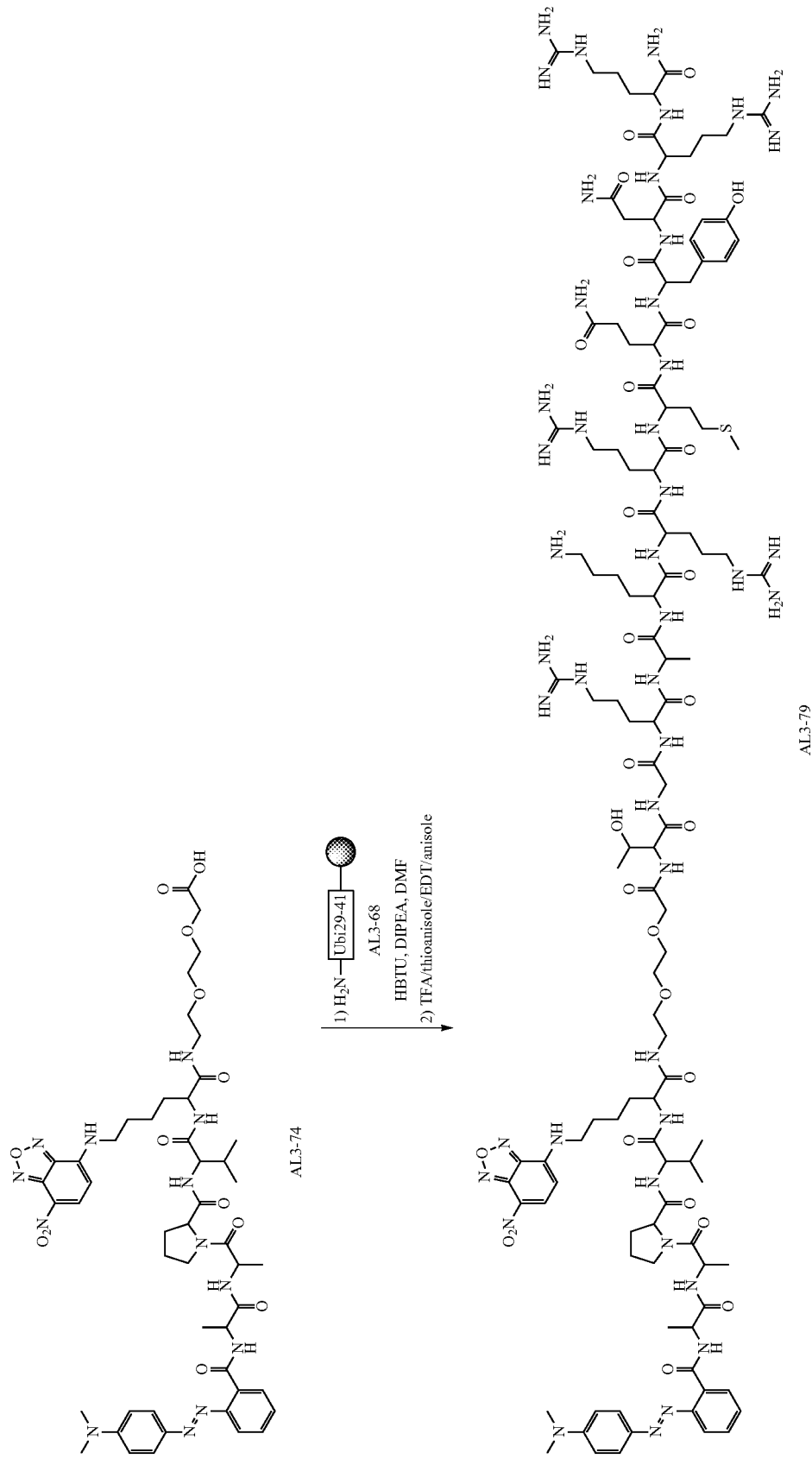

UBI$_{29-41}$ sequence was synthesised on Rink-amide ChemMatrix resin (loading 1 mmol/g) as described below. Next, AL3-74 (0.055 mmol) in anhyd. DMF (0.6 mL) was added to Ubi$_{29-41}$ on a ChemMatrix resin AL3-68 (0.03 mmol), followed by addition of HBTU (0.055 mmol) and DIPEA (0.22 mmol). The reaction mixture was shaken overnight covered from light. After filtration, the resin was washed with DMF, DCM and MeOH. The resin was swollen with DCM and the probe was deprotected and cleaved off the resin with TFA/thioanisole/EDT/anisole (90:5:3:2) (3 h). The crude precipitated with cold ether and collected by centrifugation. The product AL3-79 was purified by preparative HPLC with detection at 490 nm and gradient of H$_2$O-ACN with 0.1% formic acid as an eluent. MALDI-TOF MS 2719.4, >95% HPLC purity.

TAMRA-AAPV-NBD-UBI29-41 (SEQ ID NO: 9) AL3-88 (Maldi-TOF MS 281.5, >95% HPLC purity) was synthesised in similar manner expect fragment TAMRA-AAPV K(NBD)-PEG-OH (SEQ ID NO: 20) (AL3-75) was coupled to the N-terminus of UBI-based peptide on resin AL3-68.

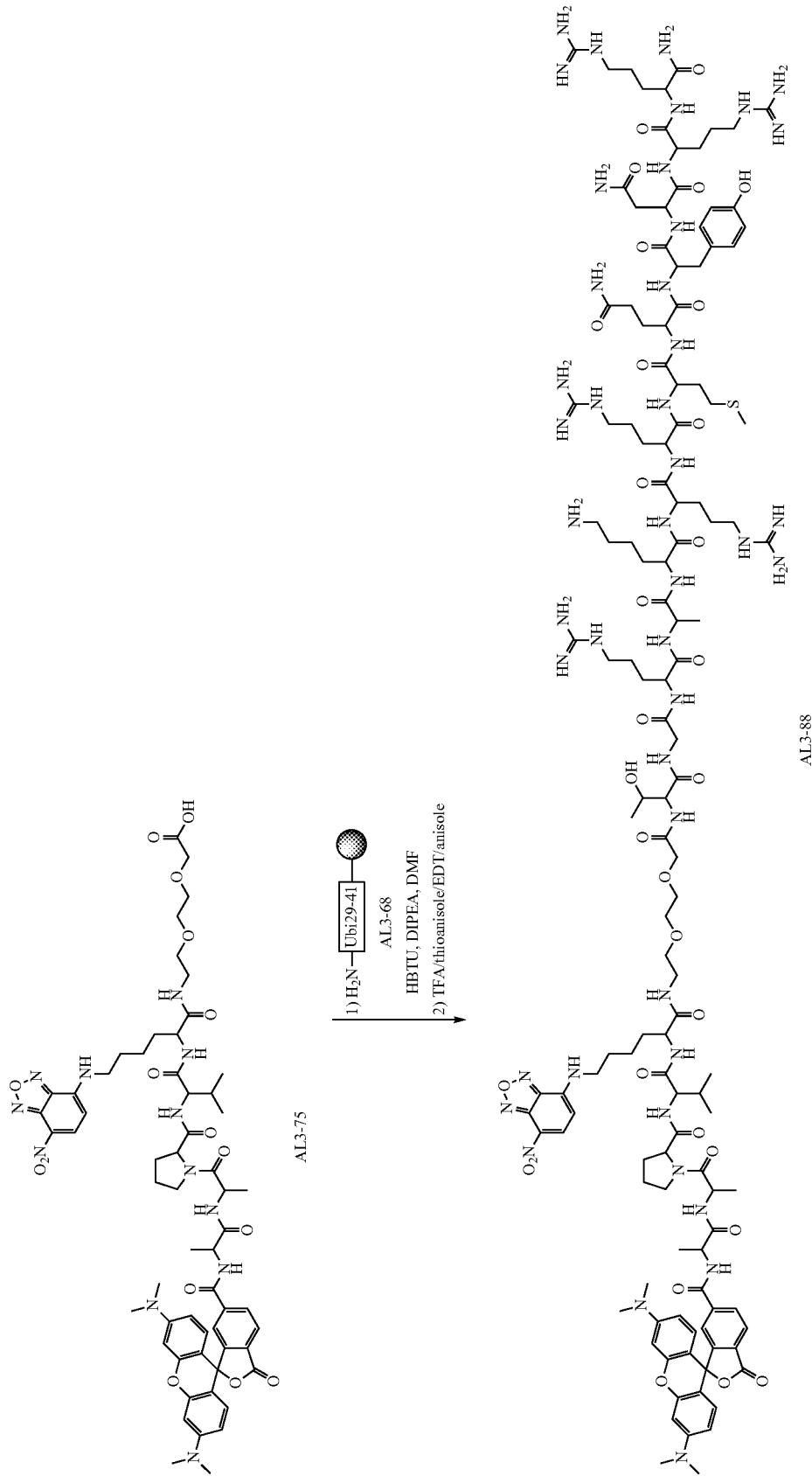
Scheme 2 Synthesis of TAMRA-AAPV-NBD-UBI29-41 (SEQ ID NO: 9)

Synthesis of Polymyxin-Based NeBac-Probe

Scheme 3 Synthesis of TAMRA-AAPV-NBD-PMX (SEQ ID NO: 9)
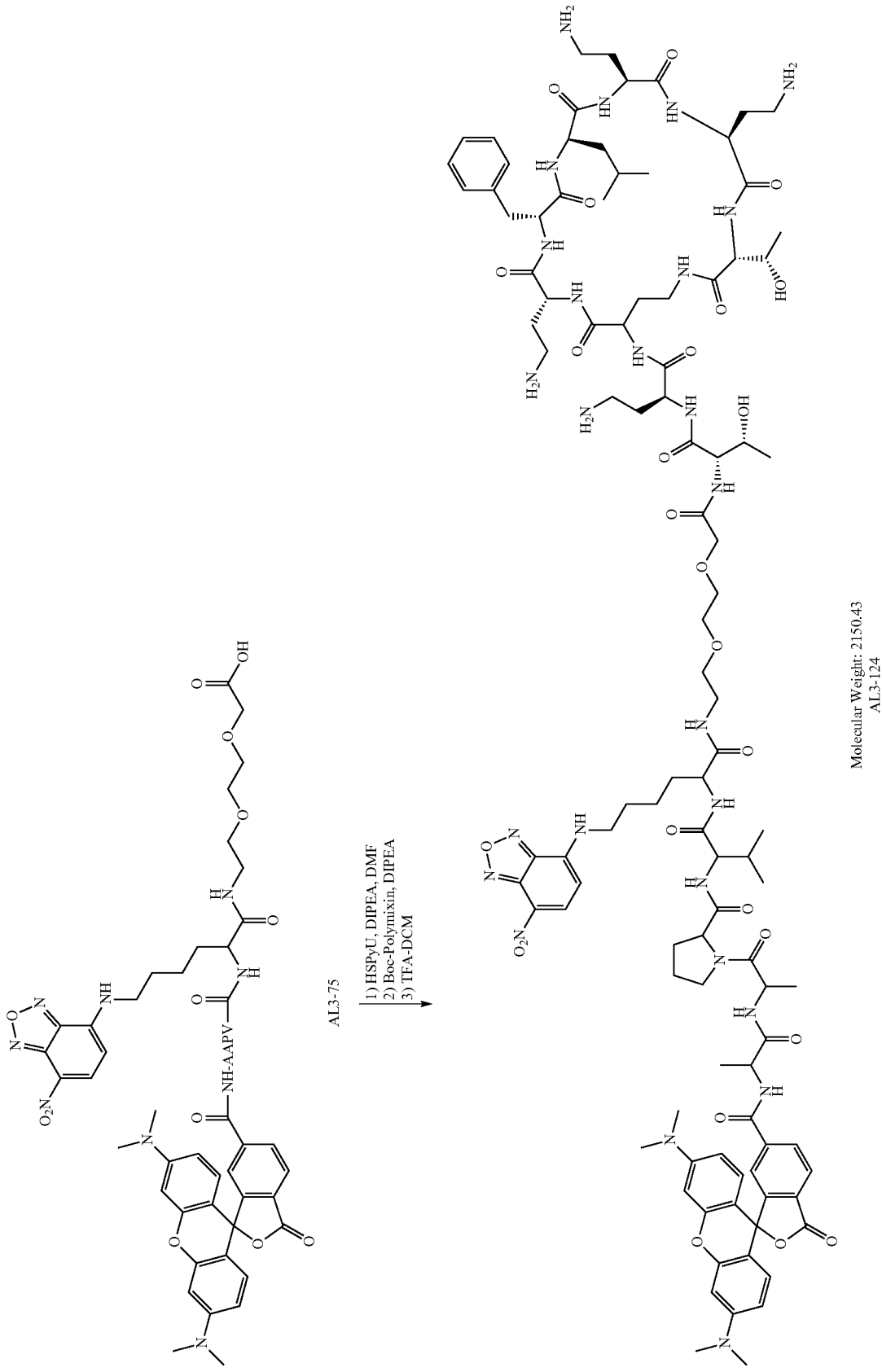
Molecular Weight: 2150.43

TAMRA-AAPV-K(NBD)-PEG-OH (SEQ ID NO: 20) fragment 3A was synthesised on solid-phase employing Fmoc-strategy, with standard amino acid coupling cycles (2×30 min at rt) with DC and oxyma in peptide grade DMF at ~0.1 mM reagent concentration. Fmoc deprotection steps were done in 20% piperidine in DMF (2×30 min). Between each step, the resin was washed with DMF, DC M and MeOH.

500 mg of chlorotrityl polystyrene resin (loading ~0.3 mmol/g) was treated with Fmoc-PEG-OH (3 eq) and DIPEA (6 eq) in anhyd. DCM (2 mL) for 3 h, After washing and Fmoc deprotection, the Fmoc-AAPVK(Dde)-(SEQ ID NO: 20) sequence was synthesised as described above using, Fmoc-Lys(Dde)-OH, Fmoc-Val-OH, Fmoc-Pro-OH, and Fmoc-Ala-OH. After the sequence was completed, Dde protecting group was orthogonally removed with $NH_2OH/$ imidazole in NMP/DCM (2×90 min). The resin was treated with NDB-Cl (3 eq) and DIPEA (6 eq) in DMF (2×45 min). After Fmoc deprotection, 5(6) carboxyTAMRA was coupled to the N-terminus as described above. After washing, the fragment was cleaved off the resin with TFA-TIS-$H_2O$ (96:2.5:2.5) (30 min) and precipitated with ether. 3A ESI-MS1044.4, and 1066.4.

Next, to 3A (0.011 mmol) in anhyd. DMF (0.5 mL), HSPyU (0.011 mmol) and DIPEA (0.033 mmol) were added, and the reaction was stirred at rt for 1 h. Boc-protected Polymyxin (15 mg, 0.012 mmol in 0.5 mL DMF) and DIPEA (0.033 mmol) were added, and the reaction mixture was stirred overnight covered from light. DMF was evaporated, the crude dissolved into 1 mL TFA-DCM (1:1), and stirred for 90 min. TFA-DCM was evaporated, the crude precipitated with cold ether, and collected by centrifugation. The product was purified by preparative HPLC with detection at 490 nm and gradient of $H_2O$-ACN with 0.1% formic acid as an eluent. Maldi-TOF MS 2151.6 and 2173.6, 100% HPLC purity.

Synthesis of NBD-UBI$_{dend}$

Synthesis of Monomer (5)

Synthesis required the preparation of the monomer (5) which was synthesised in six steps[1] as shown in Scheme 1. Monomer (5) was prepared by the 1,4 addition of the hydroxy groups of 1,1,1-tris(hydroxymethyl)amino-methane onto acrylonitrile, followed by amino group protection (Boc). Hydrogenolysis of the nitrile groups with $PtO_2/H_2$ gave (3) which was treated with DdeOH to give the tris-Dde protected amine (4). Following removal of the Boc protecting group, the isocyanate (5) was prepared following the procedure of Knölker.[2]

Scheme 4 Synthesis of monomer (5)

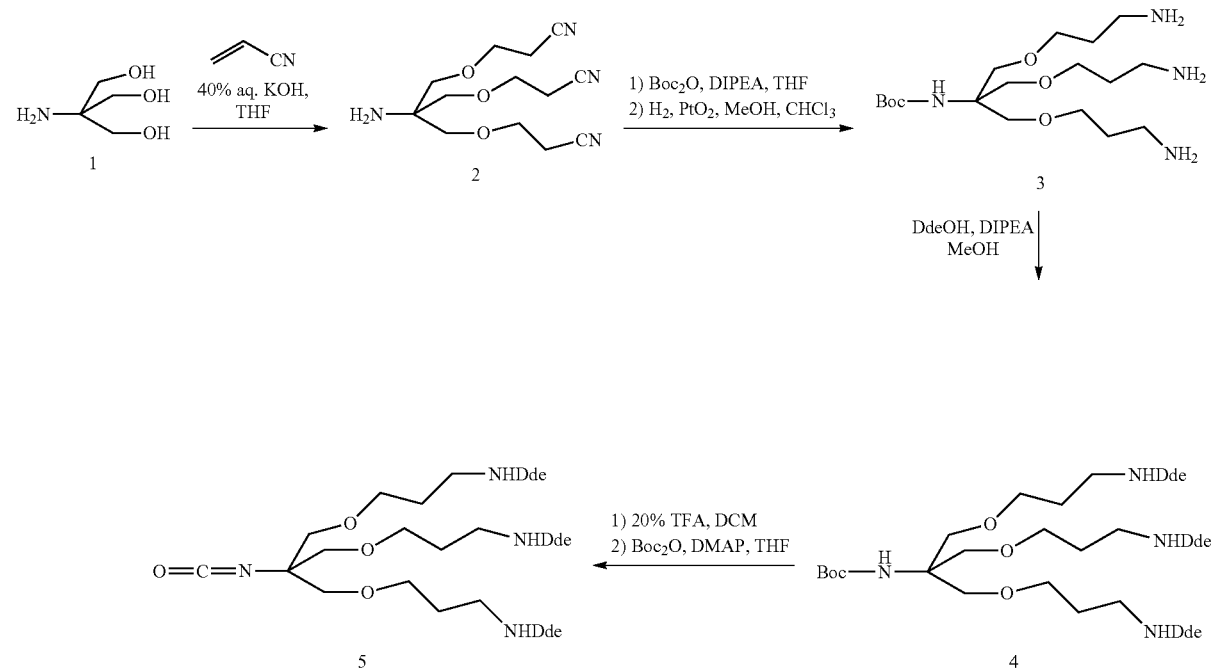

Fmoc-Rink Amide ChemMatrix Resin (6)

4-[(2,4-Dimethoxyphenyl)-(Fmoc-amino)methyl]phenoxyacetic acid (Rink amide linker) was attached to Chem-Matrix resin (LV=1 mmol/g). Thus the Fmoc-Rink-amide linker (0.2 mmol, 1 eq) was dissolved in DMF (4 mL) and ethyl oximinocyanoacetate (Oxyma) (0.2 mmol, 1 eq) was added and the mixture was stirred for 5 min. N,N'-Diisopropylcarbodiimide (DIC) (0.2 mmol 1 eq) was then added and the resulting mixture was stirred for a further 2 min. The solution was added to ChemMatrix resin (0.1 mmol, 1.0 mmol/g, 1 eq) and shaken for 0.5 hour. The resulting resin was washed with DMF (3×5 mL), DCM (3×5 mL) and MeOH (3×5 mL). The coupling reaction was monitored by a quantitative ninhydrin test[3].

Scheme 5 Synthesis of NBD-UBI$_{dend}$

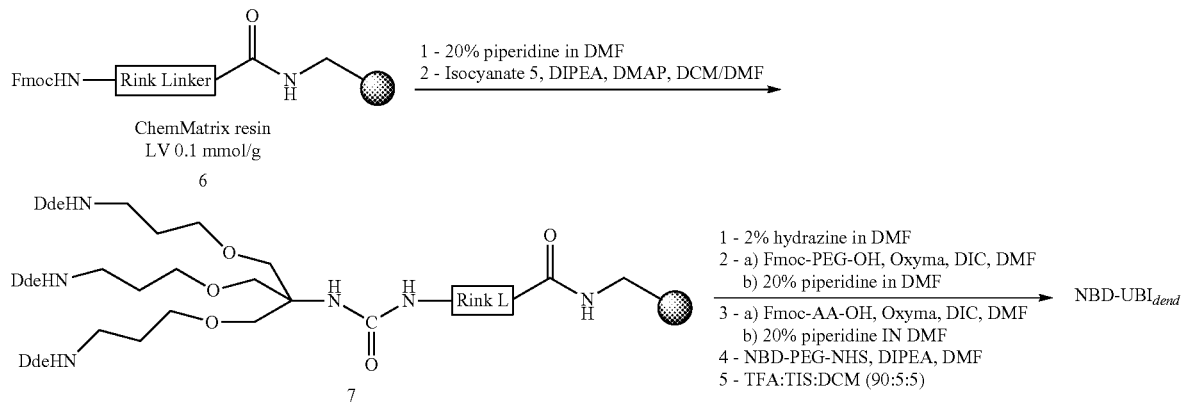

Peptide Synthesis

Peptide Sequence: Thr-Gly-Arg-Ala-Lys-Arg-Arg-Nle-Gln-Tyr-Asn-Arg-Arg (SEQ ID NO: 3) A solution of the appropriate Fmoc-amino acid (3.0 mmol, 10 eq) (Fmoc-Arg(Boc)-OH, Fmoc-Asn(Trt)-OH, Fmoc-Tyr(tBu)-OH, Fmoc-Gln(Trt)-OH, Fmoc-Nle-OH, Fmoc-Lys(Boc)-OH, Fmoc-Ala-OH, Fmoc-Gly-OH, Fmoc-Thr(tBu)-OH) and Oxyma (3.0 mmol, 10eq) was added and the mixture was stirred for 5 min, DIC (3.0 mmol, 10 eq) was then added and the resulting mixture was stirred for a further 2 min. The solution was added to pre-swollen resin in DCM and the reaction mixture was shaken for 0.5 h. The solution was drained and the resin washed DMF (3×20 L), DCM (3×20 mL) and MeOH (3×20 mL). The coupling reactions were monitored by a quantitative ninhydrin test[3].

The probe was synthesised on a ChemMatrix resin derivatized with an Fmoc-Rink Amide type linker (Scheme 2). The linker (6) was loaded with monomer (5) to give the tri-branched scaffold (7). Following the removal of the Dde groups (2% hydrazine in DMF) the appropriate Fmoc-Amino acids were coupled sequentially followed by the attachment of 4-PEG-7-nitrobenzofurazan N-hydroxysuccinimide ester (NBD-PEG-NHS) and cleaved from the resin using TFA/TIS/DCM (90/5/5).

General Procedure for the Fmoc Deprotection

To the resin (pre-swollen in DCM) was added 20% piperidine in DMF (5 mL) and the reaction mixture was shaken for 10 min. The solution was drained and the resin was washed with DMF (3×10 mL), DCM (3×10 mL) and MeOH (3×10 mL). This procedure was repeated twice. The coupling reaction was monitored by a quantitative ninhydrin test[3].

Isocyanate Coupling to Give (7)

To resin (0.30 mmol), pre-swollen in DCM (10 mL), was added a solution of isocyanate (6) (920 g, 0.93 mmol), DIPEA (0.2 mL, 0.93 mmol) and DMAP (22 mg, 0.17 mmol) in a mixture of DCM/DMF (1:1, 5 mL) and the mixture was shaken overnight and the reaction monitored by a quantitative ninhydrin test. The solution was drained and the resin was washed with DMF (3×20 mL), DCM (3×20 mL) and MeOH (3×20 mL) and ether (3×20 mL). (3×20 mL). The coupling reaction was monitored by a quantitative ninhydrin test[3].

PEG Coupling—8-(9-Fluorenylmethyloxycarbonyl-amino)-3,6-dioxaoctanoic Acid (Fmoc-PEG-OH) Coupling A solution of Fmoc-PEG-OH (3.0 mmol, 10 eq) in DMF (3 mL) and Oxyma (3.0 mmol, 10 eq) was added and the mixture was stirred for 5 min. DIC (3.0 mmol, 10 eq) was then added and the resulting mixture was stirred for a further 2 min. The solution was added to pre-swollen resin (7) in DCM and the reaction mixture was shaken for 0.5 h. The solution was drained and the resin was washed with DMF (3×10 mL), DCM (3×10 mL) and MeOH (3×10 mL). The coupling reaction was monitored by a quantitative ninhydrin test[3].

7-Nitrobenzofurazan (NBD) Coupling

To a solution of NBD-PEG-NHS (3.0 mmol, 10 eq) in DMF (3 mL) was added DIPEA (3.0 mmol, 10 eq). The resulting solution was added to resin (1 eq), pre-swollen in DCM, and the reaction mixture was shaken for 0.5 h. The solution was drained and the resin washed with DMF (×3), DCM (×3) and MeOH (×3). The coupling reaction was monitored by a quantitative ninhydrin test[3].

TFA Cleavage and Purification of Reporter NBD-UBI$_{dend}$

The resin (45 mg), pre-swollen in DCM, was treated with a cleavage cocktail of TFA/TIS/DCM (90/5/5, 300 μL) for 2.5 h. The solution was drained and the resin was washed with the cleavage cocktail and the solution was removed in vacuo. The crude material was dissolved in a minimum amount of cleavage cocktail (50 μL) and added to ice-cold ether (7.5 mL). The precipitated solid (22 mg) was collected by centrifugation and the solvent removed by decantation and the precipitate was washed with cold ether (3×5 mL). The precipitate was then purified by preparative reverse phase HPLC and the required fractions were pooled and lyophilized to afford NBD-UBI$_{dend}$.

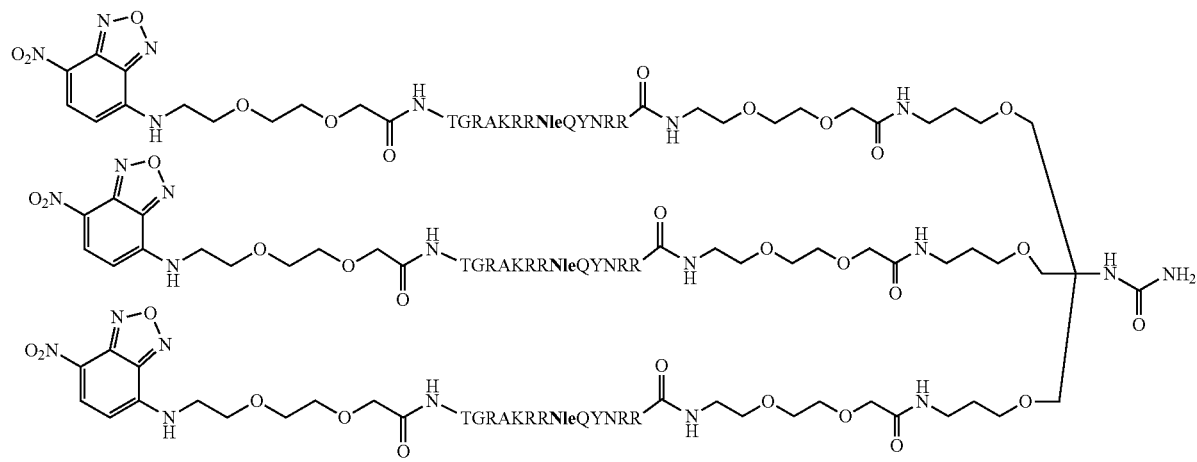

NBD-UBI$_{dend}$

Synthesis of NBD-PMX

The NBD-PMX probe was synthesised from its precursor Polymyxin B sulfate in four steps (Scheme 6). The probe and its intermediates were synthesised using reported methods[1] with moderate modifications. The fluorophore is incorporated as an amide coupling between the NHS ester of the NBD-PEG and the tetra-Boc polymyxin C. NBD-PMX probe is obtained after the TFA cleavage and HPLC purification.

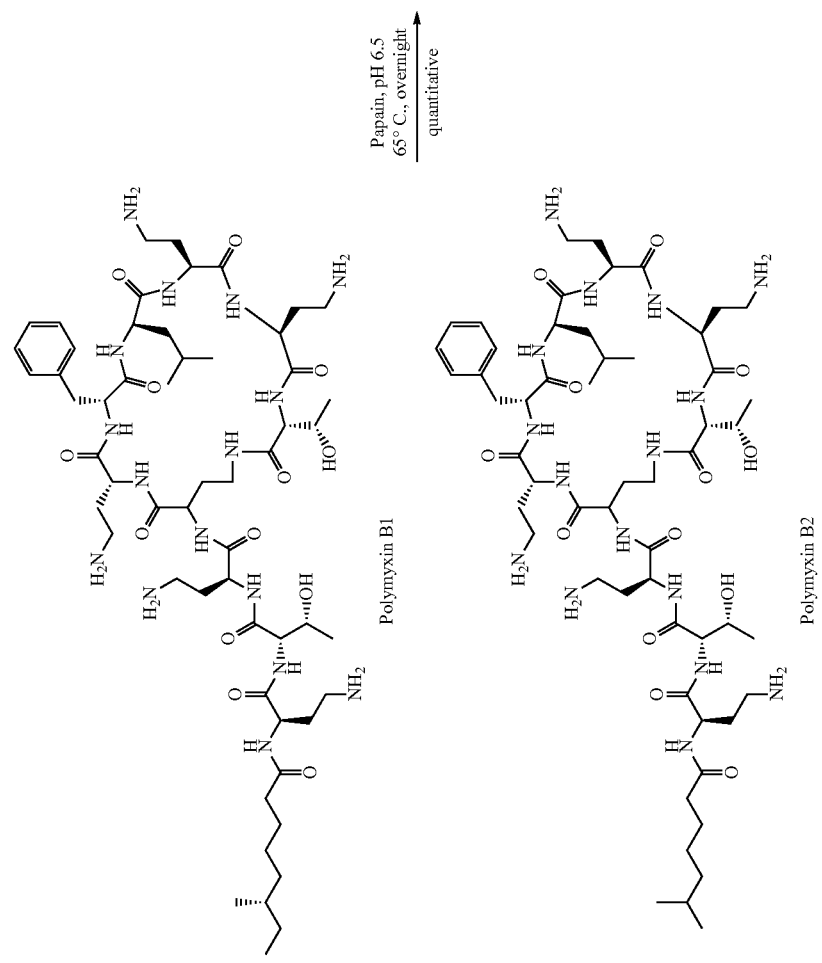
Scheme 6. Synthetic route of NBD-PMX probe.

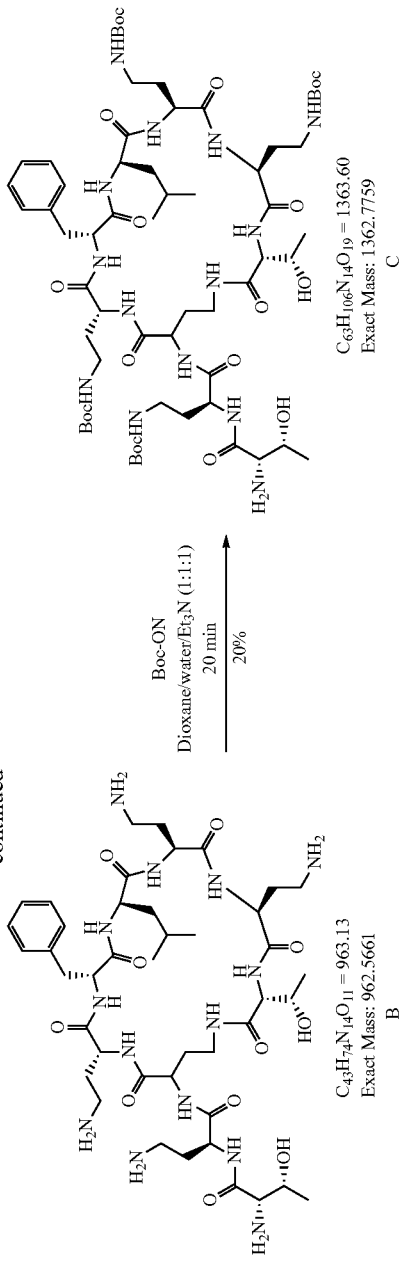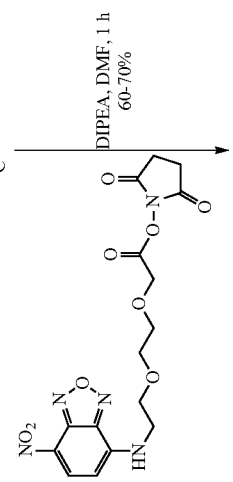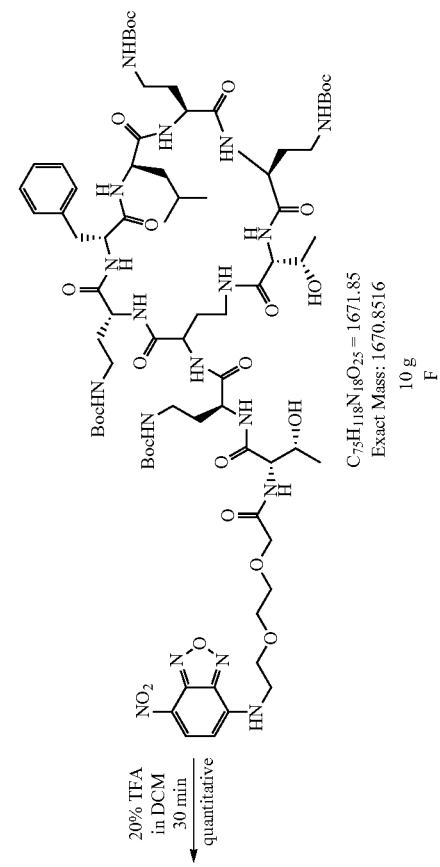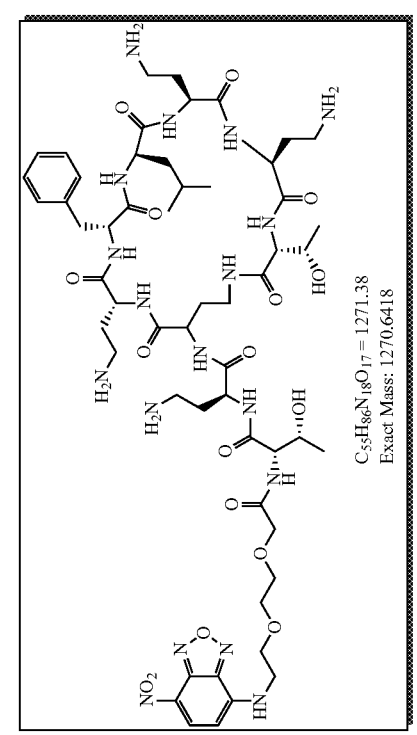

Preparation of Compound B

Polymyxin B sulfate (10 g, 7.7 mmol, 1 eq) was dissolved in deionized water (200 mL) at a pH of 6.5 (use HCl aq solution to adjust the pH). Papain (1.5 g) was dissolved in water (25 mL) (same pH). The solutions were combined and toluene (0.5 mL) was added, and the mixture was gently stirred at 65° C. overnight. The mixture was then stirred in boiling water for 5 min and the precipitate formed (denatured papain) was removed by centrifugation and filtration. The filtrate was concentrated in vacuo and freeze dried to give the crude product B in quantitative yield. This step was carried forward to the next step without any further purification. MS m/z 963.2 (100%, [M+H]$^+$).

Preparation of Compound C

Crude B (5.5 g, 5.7 mmol, 1 eq) was dissolved in a mixture of H$_2$O:Dioxane:Et$_3$N (150 mL, 1:1:1) and Boc-ON (4.52 g, 17.1 mmol, 3 eq) was added. The solution was stirred for 20 min at room temperature and then quenched with methanolic ammonia (20 mL, 2M ammonia in MeOH). The reaction was followed up by ELSD. Solvents were evaporated and the resulting mixture was subjected to silica gel chromatography column (MeOH:DCM, 15:85) to afford white solid B (1.7 g, 22%). MS m/z 1363.7 (100%, [M+H]$^+$).

N-(4-Nitrobenz-2-oxa-1,3-diazol-7-yl)amino-3,6-dioxaoctanoic Acid (NBD-PEG-OH):[2]

DIEA (850 µl, 5.00 mmol) and solid 8-Amino-3,6-dioxaoctanoic acid (NH$_2$-PEG-OH) (392 mg, 2.40 mmol, 1 eq) were added slowly, over an hour, to a solution of NBD-Cl (401 mg, 2.01 mmol) in methanol (20 mL) at 0° C. The reaction mixture was stirred overnight at room temperature. The solvent was evaporated and the remaining material was purified by chromatography on silica with DCM/MeOH (8:2) as the eluent to give NBD-PEG-OH (400 mg, 1.23 mmol, 51%) as dark red oil. $^1$H NMR (500 MHz, DMSO): δ 10.9 (s, 1H; COOH), 8.49 (d, J=8.5 Hz, 1H; CH NBD), 7.1 (s, 1H, NH), 6.23 (d, J=8.5 Hz, 1H; CH NBD), 4.25 (s, 2H), 3.93 (t, J=5.3 Hz, 2H; CH$_2$), 3.80 (s, 4H), 3.72 (t, J=6.8 Hz, 2H; CH$_2$) ppm; MS (ESI-): m/z calcd for C$_{12}$H$_{14}$N4O$_7$ [M–H]: 325.1; found: 325.2.

N-(4-Nitrobenz-2-oxa-1,3-diazol-7-yl)amino-3,6-dioxaoctanoic Acid, Succinimidyl Ester (NBD-PEG-NHS)

To a solution of NBD-PEG-OH (2.4 g, 7.4 mmol, 1 eq) in anhydrous DCM (500 mL) was added EDC.HCl (1.56 g, 8.18 mmol, 1.1 eq) and DIPEA (1.36 mL, 10 mmol). After stirring the mixture for 10 min, N-hydroxysuccinimide (0.94 g, 8.18 mmol) was added and allowed to stir for 16 h. The reaction mixture was diluted with DCM (250 mL) and treated with 5% aqueous citric acid (2×200 mL), sat. aqueous NaHCO$_3$ and brine. The organic layer was dried over Na$_2$SO$_4$, filtered and reduced in vacuo to afford product as dark brown solid (1.0 g, quantitative). The crude was used for next step without further purification.

Preparation of F

A solution of NBD-PEG-NHS (466 mg, 1.1 mmol, 1 eq), DIPEA (384 µL, 2.2 mmol, 2 eq) and amine C (1.5 g, 1.1 mmol, 1 eq) in DMF (150 mL) was stirred at room temperature for 1 h and protected from light. After completion of the reaction (TLC), volatiles are removed under vacuum. The crude mixture was purified by flash chromatography (DCM:MeOH, 90:10) to afford dark orange/brown solid (1.2 g, 65%). HPLC (254 nm & 495 nm) Rt=7.80 min; m/z 1671.7 (25%, [M+H]$^+$); 1693.9 (65%, [M+Na]$^+$).

Preparation of NBD-PMX Probe

A solution of Boc-protected polymyxin F (150 mg, 0.09 mmol) in 20% TFA in DCM (2 mL) was vigorously stirred for 45 min at room temperature and protected from light. The reaction mixture was evaporated in vacuo and the resultant was dissolved in ether. Ether layer was decanted after centrifugation (3×2 mL). The resultant yellow/brown solid (40 mg, quantitative) was dried under vacuum. The crude product was purified by preparative HPLC in MeOH/H$_2$O as gradient solvent system with 0.1% formic acid as an additive. The fractions collected from prep-HPLC were freeze dried to afford red/orange solid (30 mg, 26% recovery from HPLC).

Characterisation:

For analytical HPLC, a Poroshell 120 SB-C18, 2.7 µm, 4.6×50 mm column was used with a diode array detector. For prep-HPLC method: Discovery C18 reverse-phase column (5 cm×4.6 mm, 5 µm) with a flow rate of 1 mL/min and eluting with H2O/MeOH/HCOOH (95/5/0.05) to H2O/MeOH/HCOOH (5/95/0.05), over 6 min, holding at 95% MeOH for 4 min, with detection at 254 and 495 nm and by ELSD. HPLC (495 nm): Rt=4.1 min; MS m/z 1271.7 (95%, [M+H]$^+$); 1293.7 (100%, [M+Na]$^+$); FTMS calc. 636.3282 ([M+2H]/2)$^+$, found 636.3344.

Absorption/Emission: 467 nm/539 nm.

Solubility: Fully soluble in water.

Stability: stable at room temperature for > than 1 week.

Storage: Stored at −20° C. under inert atmosphere. Protect from light.

Biological Methods

Bacterial Growth:

Bacteria used in assays include *Pseudomonas aeruginosa* (PA01-reference strain and J3284-clinical isolate from VAP patient), *Acinetobacter baumannii, Stenotrophomonas maltophilia, Staphylococcus aureus* (Inc. methicillin-resistant *S. aureus* (MRSA), methicillin-sensitive *S. aureus* (MSSA)), *Klebsiella pneumoniae, Escherichia coli, Haemophilus influenzae* and *Streptococcus pneumoniae*.

TABLE 3

Bacteria, strain reference and original source used in experiments.

| | Bacteria | Strain | Original Source |
|---|---|---|---|
| Gram-negative bacteria | *P. aeruginosa* | ATCC 47085 (PA01) | ATCC |
| | *P. aeruginosa* | J3284 | Clinical Isolate* |
| | *A. baumannii* | J3433 | Clinical Isolate* |
| | *S. maltophilia* | J3270 | Clinical Isolate* |
| | *K. pneumoniae* | ATCC BAA1706 | ATCC |
| | *E. coli* | ATCC 25922 | ATCC |
| | *H. influenzae* | Clinical Isolate | Clinical Isolate* |
| Gram-positive bacteria | Methicillin Resistant *S. aureus* (MRSA) | ATCC25923 | ATCC |
| | Methicillin Sensitive *S. aureus* (MSSA) | ATCC 252 | ATCC |

TABLE 3-continued

Bacteria, strain reference and original source used in experiments.

| Bacteria | Strain | Original Source |
|---|---|---|
| S. pneumoniae | D39 NCTC 7466 | Health protection agency culture collection |
| GFP fluorescent S aureus | RN6390-Gfp-EryR | Nottingham University (Gift from Professor Phil Hill) |

*Gifts from Professor John Govan, University of Edinburgh.

All bacteria were grown on agar broth, chocolate agar or blood agar plates, stored at 4° C. For assays, a single colony of bacteria was taken using an inoculating loop and added to 10 ml liquid broth in a 50 ml Falcon Tube. This was transferred to an incubator at 37° C. for 16 hours (for Streptococcus pneumoniae supplemented with 5% $CO_2$). Cultures were either used as overnight cultures (stationary phase) or from these cultures a sub-culture was taken (1:100) and the sample was grown until they entered mid log phase (reads of 0.5-0.6 optical density (OD) on spectrophotometer at 595 nm). The culture was then centrifuged at 4000 rpm for 5 minutes and pellet resuspended in phosphate buffered saline (PBS). Following three washes this was reconstituted to 0.5 $OD_{595}$nm for confocal assays, 0.1 $OD_{595}$ nm for flow cytometry or 2 $OD_{595}$nm for ovine ex vivo lung experiments (unless otherwise stated).

Bacterial Counting:

Samples (prepared bacteria or lavage from ovine lung segments) were vortexed briefly then serial dilutions (1:10) were performed to dilutions to the 8th dilution. The broth/blood agar plate was divided into quadrants with 5×20 ul drops in each quadrant. These were incubated at 37° C. for 16 hours (for Streptococcus pneumoniae supplemented with 5% $CO_2$) and plates were counted with data reported as colony forming units per millilitre (CFU/ml).

Surfactant Constituent Synthesis:

Surfactant 5 µg 1,2-Dipalmitoyl-sn-glycero-3-phosphocholine (DPPC) and 2.5 µg L-α-Phosphatidyl-DL-glycerol sodium salt (from egg yolk lecithin; PG) were dissolved in 500 µl chloroform and evaporated under nitrogen to a thin lipid film in a round bottom flask. The lipid film was rehydrated with PBS at 48° C. for 1 hour with agitation (750 rpm) to generate multilammelar vesicles (MLV). These were diluted 1:4 for use in confocal experiments.

Agarose Bacterial Beads:

Bacteria were grown to midlog phase in 400 ml TSB, pelleted by centrifugation and resuspended in 2 ml PBS. This was mixed with 18 ml molten tryptic-soy agar (50° C.) and injected rapidly into vortexing mineral oil+0.01% Span 80, pre-warmed to 50° C. This was then rapidly cooled to 4° C. whilst continuing to vortex to allow the beads to set. Bacterial agar beads were pelleted by centrifugation (20 minutes, 3000 g) and washed in 0.5% sodium deoxycholate (SDC) in PBS (20 minutes, 3000 g), followed by 0.25% SDC (20 minutes, 3000 g) in PBS, washed in PBS (10 minutes, 3000 g) and 3×PBS (5 minutes, 200 g). Beads were resuspended at 50% v/v in PBS for instillation.

Neutrophil Extraction:

Neutrophils were isolated from the peripheral blood of healthy human volunteers by dextran sedimentation followed by centrifugation through discontinuous plasma-Percoll gradients.

A549 Cultures:

A549 cells were grown in Dulbecco's modified Eagle's medium (DMEM) supplemented with 10% fetal bovine serum (FBS), 2 mM L-glutamine, 100 units/mL penicillin G and 100 µg/mL streptomycin to 80% confluence. Cells were dispersed with Trypsin-EDTA and seeded onto glass coverslips or 8 well confocal imaging chambers and grown to confluence in the presence of DMEM.

Confocal Analysis:

Bacteria were prepared and counterstained with Syto 82 nucleic acid stain (Invitrogen, Calif., USA) in a shaking heat block at 37° C. and 350 rpm for 20 minutes. They were co-incubated with the probe at required concentration in a sealed POC mini chamber, or 8 well confocal chamber. When required the glass coverslip for the POC chamber was coated in fibronectin (for neutrophil experiments) or poly-d-lysine (for bacteria and cell lines) and incubated with cells with one hour at 37° C. to allow adherence prior to bacterial innoculation. Analysis was with ImageJ. Briefly, the Syto channel was automatically thresholded (Huang) and an ROI generated from this. The mean fluorescence intensity on the probe channel within this ROI was quantified. Data presented represents the mean of three separate fields of view.

Flow Cytometry:

Bacteria were prepared and counterstained with Syto 82 nucleic acid stain (Invitrogen, Calif., USA) in a shaking heat block at 37° C. and 350 rpm for 20 minutes. Bacteria were washed in PBS×3, and probe (50 µl) added in 50 ul $OD_{595}$ 1 od bacteria. This was diluted to 500 uL and analysed using BD FACS Calibur using FL-1 and FL-2 channels, with 10,000 events. Analysis was with FlowJo software following gating on the FL-2 channel.

Lung Harvesting and pCLE procedure:

From a cohort of surplus stock ewes which were destined for cull, one ewe was identified and terminally euthanized with an overdose of anaesthetic. Death was confirmed and the trachea was identified and clamped in situ. The thoracic cavity was then accessed and the lungs were freed from surrounding tissues and organs and the heart/lung was removed en block. The right pulmonary artery was identified, cannulated and perfused with 1000 ml 0.9% NaCl. Once filling of the left ventricle was confirmed an incision was made to allow free drainage and perfusion continued until the drainage from the left atrium was clear. The trachea was intubated with an 8.0 endotracheal tube immediately following clamp release. The lungs were placed in a neonatal incubator with an ambient temperature of 37° C. and humidity of 65% and ventilated using a Pressure Controlled Ventilator (Breas Vivo PV 403). Ventilator setting was adjusted to aid maximal parenchymal recruitment and aiming to achieve tidal volume>1 litre. Following 1 hour of optimal ventilation, bronchoscopy was undertaken and individual segments were identified and instilled with 2 ml of bacteria or PBS control. Following instillation a separate sheath (ERBE) was introduced and the probe was instilled. Then the probe-based Confocal Laser Endomicroscopy (pCLE) fibre was passed down the working channel and the segment was imaged. For BALF, the bronchoscope was wedged and 20 ml of 0.9% NaCl instilled and carefully withdrawn with lavage yields of 40-50%. Control segments were anatomically distinct and/or in the contralateral lung. The bronchoscope was decontaminated between each segment imaged.

Haemolysis Assay:

Erythrocytes were isolated from freshly drawn, anticoagulated human blood and resuspended to 20 vol % in PBS (pH 7.4). In a 96-well microtiter plate, 100 µl of erythrocyte suspension was added to 100 µl of NLLP solution in PBS (prepared by 1:2 serial dilutions) or 100 µl of PBS in the case of negative controls. One-hundred percent haemolysis wells contained 100 µl of red cell suspension with 100 µl of 0.2 vol % Triton X-100. The plate was incubated for 1 h at 37° C., and then each well was diluted with 150 µl of PBS. The plate was then centrifuged at 1,200 g for 15 min, 100 µl of the supernatant from each well was transferred to a fresh microtiter plate, and A350 was measured. Percentage of haemolysis was determined as (A−A0)/(Atotal−A0)×100, where A is the absorbance of the test well, A0 the absorbance of the negative controls, and Atotal the absorbance of 100% haemolysis wells, all at 350 nm on a Biotek plate reader.

MALDI-TOF:

Probe was added to saline or pooled BALF from patients with ALI incubated for 30 minutes. A ZipTip (C-18, 0.2 µL) with 5 µL MeCN (with 0.1% TFA as an additive) followed by 20 µL of H2O was washed. The ZipTip was loaded with the sample, washed and eluted into 5 µL of 80% aq. MeCN (with 0.1% TFA as an additive). The sample was analysed by MALDI-TOF (PerSeptive Biosystems Voyager DE™STR MALDI-TOF mass spectrometer (Applied Biosystems, Foster City, Calif.)).

Statistical Analysis:

All experiments were performed at least three times unless otherwise stated and results expressed as mean±SEM. Data was analysed by unpaired t-test or ANOVA, significance was determined as p<0.05 (GraphPad Prism).

REFERENCES

1. M. Ternon, J. J. Diaz-Mochon, A. Belsom, M. Bradley, *Tetrahedron*, 2004, 60, 8721
2. H. J. Knölker, T. Braxmeier, G. Schlechtingen, *Angew. Chem. Int. Ed.*, 1995, 34, 2497
3. E. Kaiser, R. L. Colescott, C. D. Bossinger and P. I. Cook, *Analytical Biochemistry*, 1970, 34, 595-598.

LISTING OF RELEVANT SEQUENCES

```
Ubiquicidin (full)
                                                             SEQ ID NO. 1
KVHGSLARAG KVRGQTPKVA KQEKKKKKTG RAKRRMQYNR RFVNVVPTFG KKKGPNANS Ubiquicidin (UBI29-41)
                                                             SEQ ID NO. 2
TGRAKRRMQY NRR Ubiquicidin (UBI_Nle)
                                                             SEQ ID NO. 3
TGRAKRRNleQY NRR Polymyxin
                                                             SEQ ID NO. 4
```

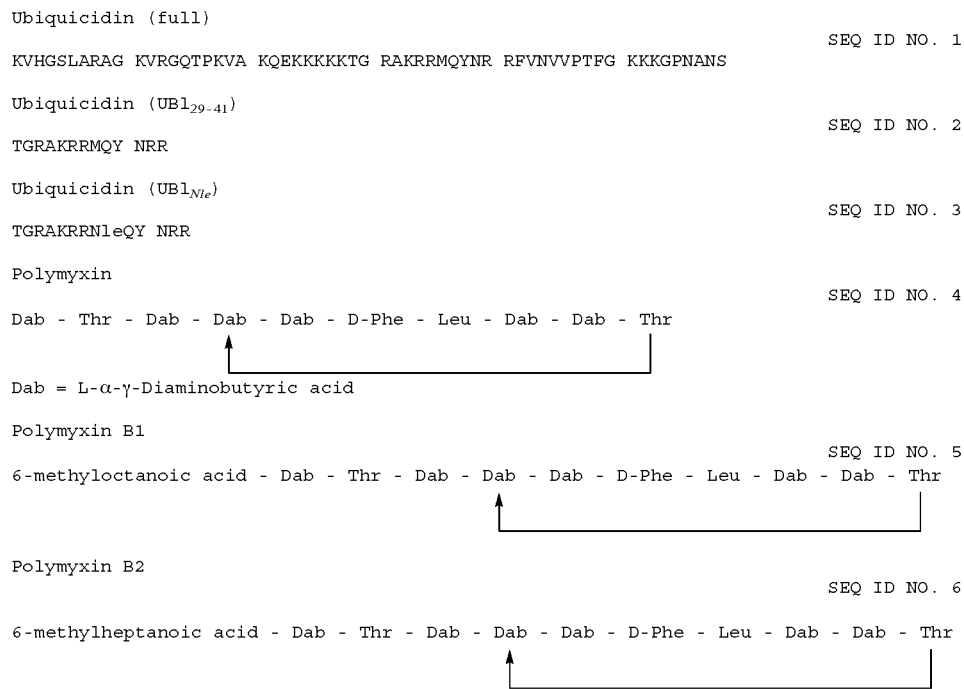

```
Dab = L-α-γ-Diaminobutyric acid

Polymyxin B1
                                                             SEQ ID NO. 5
6-methyloctanoic acid - Dab - Thr - Dab - Dab - Dab - D-Phe - Leu - Dab - Dab - Thr Polymyxin B2
                                                             SEQ ID NO. 6
6-methylheptanoic acid - Dab - Thr - Dab - Dab - Dab - D-Phe - Leu - Dab - Dab - Thr
```

SEQ ID NO 7
Mass spectrometry fragment of (UBI$_{29-41}$)
YNRR
SEQ ID NO 8
Mass spectrometry fragment of (UBI$_{29-41}$)
Nle-QYNRR

The invention claimed is:

1. A probe comprising a core and a plurality of probe elements, each probe element within the plurality of probe elements extending from the core and comprising a fluorophore and a binding moiety, wherein the binding moiety is a bacteria binding moiety and selectively binds to at least some bacteria, and does not bind to animal cells, or wherein the binding moiety is a fungi binding moiety, or wherein the binding moiety selectively binds to at least some bacteria and to at least some fungi, and not bind to animal cells, wherein the probe has one of the following structures:

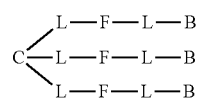

1

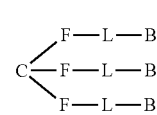

2

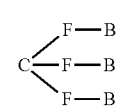

3

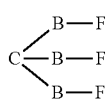

4

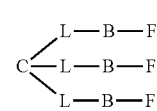

5

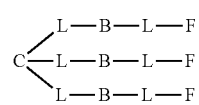

6

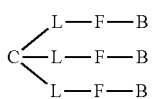

7

-continued

```
     B—L—F
   /
C———B—L—F
   \
     B—L—F
```
8

```
   /F—B
C
   \F—B
```
9

```
   /L—F—B
C
   \L—F—B
```
10

```
   /F—L—B
C
   \F—L—B
```
11 where
L=spacer group
F=fluorophore
B=binding moiety
C=core.

2. The probe according to claim 1, wherein the probe comprises three probe elements connected to a core each probe element comprising NBD-$(CH_2)_5$CO-UBI$_{Nle}$.

3. The probe according to claim 1, wherein the probe comprises three probe elements connected to a core each of the three probe elements comprising NBD-$(CH_2)_2$O$(CH_2)_2$OCH$_2$-PMX.

4. The probe according to claim 1, wherein the probe has the structure:

[Chemical structure showing three NBD-linked TGRAKRRNleQYNRR peptide branches connected to a urea core]

wherein the binding moiety is SEQ ID NO 3.

5. A method of detecting bacteria and/or fungi in a target area, the method comprising the steps:
(1) providing a first probe according to claim 1;
(2) delivering the first probe to the target area;
(3) illuminating the target area with an appropriate wavelength of light to excite the fluorophores of the first probe; and
(4) determining whether the first probe has labelled bacteria and/or fungi within the target area.

6. The method according to claim 5, wherein the method comprises the further steps of: providing a second probe delivering the second probe to the target area; and illuminating the target area with an appropriate wavelength of light to excite the or each fluorophore of the second probe;
wherein the second probe comprises a core and a plurality of probe elements, each probe element within the plurality of probe elements extending from the core and comprising a fluorophore and a binding moiety, wherein the binding moiety is a bacteria binding moiety that specifically binds to a subpopulation of bacteria, and does not bind to animal cells, and wherein the probe has one of the following structures:

-continued

```
   /L—F—L—B
C
   \L—F—L—B
```
12

```
   /B—F
C
   \B—F
```
13

```
   /L—B—F
C
   \L—B—F
```
14

```
   /B—L—F
C
   \B—L—F
```
15

```
   /L—B—L—F
C
   \L—B—L—F
```
16

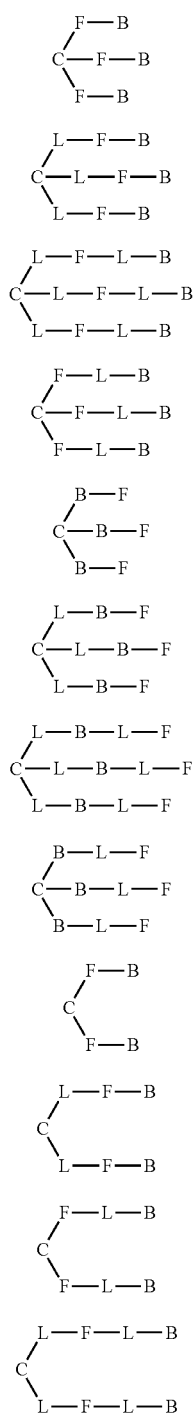

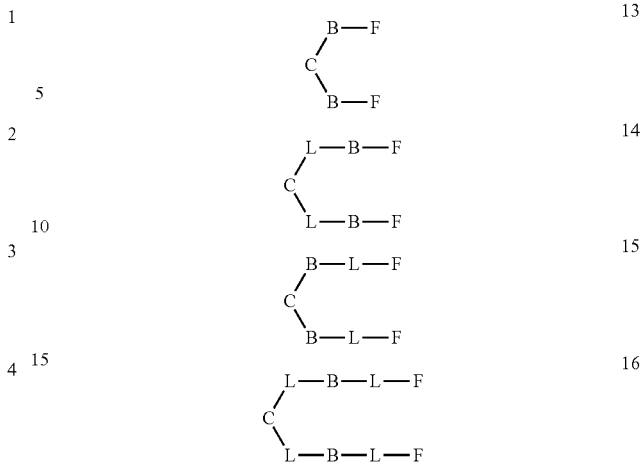

where
L=spacer group
F=fluorophore
B=binding moiety
C=core.

7. The method according to claim 6, wherein the first probe comprises a ubiquicidin moiety, including full length ubiquicidin, or a fragment thereof as the binding moiety.

8. The method according to claim 6, wherein the second probe comprises a polymyxin moiety, including full length polymyxin or a fragment thereof, as the binding moiety, and the second probe may selectively bind to gram negative bacteria.

9. The method according to claim 8, wherein the first probe comprises a ubiquicidin moiety and the method allows the identification of sterile inflammation, bacterial and/or fungal inflammation, and gram-negative bacterial infection and by inference, gram-positive bacterial infection.

10. A kit of parts comprising a first probe according to claim 1 comprising at least one binding moiety that specifically binds to bacteria and/or fungi, and a second probe according to claim 1 comprising at least one binding moiety that specifically binds to gram-negative or gram-positive bacteria and a suitable buffer within which the probe may be dispersed.

11. The kit of parts according to claim 10, wherein the first probe comprises at least one ubiquicidin moiety, and the second probe comprises at least one polymyxin moiety.

12. The probe according to claim 1, wherein L is $C_3$-$C_{10}$ alkyl, or $((CH_2)_2O)_x$ where x=1-6.

13. The probe of claim 1, wherein F is NBD or fluorescein.

14. The probe of claim 1, wherein B is a ubiquicidin moiety or a polymyxin moiety.

15. The probe of claim 1, wherein C is carbon, —$C(CH_2O(CH_2)_3)_3$, or $NH_2CONHC(CH_2O(CH_2)_3)_3$.

* * * * *